US011872235B1

(12) United States Patent
Patel et al.

(10) Patent No.: US 11,872,235 B1
(45) Date of Patent: *Jan. 16, 2024

(54) BIOAVAILABLE SOLID STATE (17-β)-HYDROXY-4-ANDROSTEN-3-ONE ESTERS

(71) Applicant: Lipocine Inc., Salt Lake City, UT (US)

(72) Inventors: Mahesh V. Patel, Salt Lake City, UT (US); Nachiappan Chidambaram, Salt Lake City, UT (US); Satish Kumar Nachaegari, Salt Lake City, UT (US); Srinivasan Venkateshwaran, Salt Lake City, UT (US); Joel Frank, Salt Lake City, UT (US)

(*) Notice: Subject to any disclaimer, the term of this patent is extended or adjusted under 35 U.S.C. 154(b) by 20 days.

This patent is subject to a terminal disclaimer.

(21) Appl. No.: 17/694,827

(22) Filed: Mar. 15, 2022

Related U.S. Application Data

(63) Continuation of application No. 16/849,957, filed on Apr. 15, 2020, now Pat. No. 11,298,365, which is a continuation of application No. 16/273,911, filed on Feb. 12, 2019, now abandoned, which is a continuation of application No. 15/672,185, filed on Aug. 8, 2017, now abandoned, which is a continuation of application No. 15/276,389, filed on Sep. 26, 2016, now Pat. No. 9,757,389, which is a continuation of application No. 14/839,820, filed on Aug. 28, 2015, now Pat. No. 9,498,485.

(60) Provisional application No. 62/043,337, filed on Aug. 28, 2014.

(51) Int. Cl.
*A61K 31/568* (2006.01)
*A61K 39/00* (2006.01)
*A61K 9/00* (2006.01)
*A61K 9/16* (2006.01)

(52) U.S. Cl.
CPC .......... *A61K 31/568* (2013.01); *A61K 9/0053* (2013.01); *A61K 9/16* (2013.01); *A61K 39/00* (2013.01)

(58) Field of Classification Search
CPC .................................................. A61K 31/568
See application file for complete search history.

(56) References Cited

U.S. PATENT DOCUMENTS

| | | |
|---|---|---|
| 2,680,749 A | 6/1954 | Cawley et al. |
| 2,742,487 A | 4/1956 | Robledano |
| 3,097,139 A | 7/1963 | Thorp |
| 3,097,144 A | 7/1963 | Banker |
| 3,164,520 A | 1/1965 | Huber |
| 3,266,991 A | 8/1966 | Wettstein et al. |
| 3,510,561 A | 5/1970 | Koh |
| 4,098,802 A | 7/1978 | Van der Vies |
| 4,147,782 A | 4/1979 | Klein et al. |
| 4,147,783 A | 4/1979 | Van der Vies |
| 4,156,719 A | 5/1979 | Sezaki et al. |
| 4,177,188 A | 12/1979 | Hansen et al. |
| 4,196,188 A | 4/1980 | Besins |
| 4,220,599 A | 9/1980 | Van der Vies |
| 4,239,754 A | 12/1980 | Sache et al. |
| 4,388,307 A | 6/1983 | Cavanak |
| 4,439,432 A | 3/1984 | Peat |
| 4,572,915 A | 2/1986 | Crooks |
| 4,579,730 A | 4/1986 | Kidron et al. |
| 4,628,052 A | 12/1986 | Peat |
| 4,628,098 A | 12/1986 | Nohara et al. |
| 4,654,327 A | 3/1987 | Teng |
| 4,656,161 A | 4/1987 | Herr |
| 4,689,333 A | 8/1987 | Nohara et al. |
| 4,695,450 A | 9/1987 | Bauer |
| 4,703,042 A | 10/1987 | Boder |
| 4,713,246 A | 12/1987 | Begum et al. |
| 4,717,569 A | 1/1988 | Harrison et al. |
| 4,717,596 A | 1/1988 | Barbee et al. |
| 4,719,239 A | 1/1988 | Muller et al. |
| 4,727,109 A | 2/1988 | Schmidt et al. |
| 4,731,384 A | 3/1988 | Dell |
| 4,795,327 A | 1/1989 | Gaylord et al. |
| 4,832,952 A | 5/1989 | Hersh et al. |
| 4,834,965 A | 5/1989 | Martani et al. |
| 4,849,227 A | 7/1989 | Cho |
| 4,867,984 A | 9/1989 | Patel |
| 4,874,795 A | 10/1989 | Yesair |

(Continued)

FOREIGN PATENT DOCUMENTS

| | | |
|---|---|---|
| CA | 2295028 | 10/1999 |
| CA | 2302735 | 1/2000 |

(Continued)

OTHER PUBLICATIONS

Addo et al.; "Non Polar Extracts of Serum From Males Contain Covert Radioimimmoassayable Testosterone;" Steroids; (Sep. 1989), pp. 25-269; vol. 54(3).
Alvarez et al.; "The Role of Calcium Jons and Bile Salts on the Pancreatic Lipase-Catalyzed Hydrolysis of Triglyceride Emulsions Stabilized with Lecithin;" Pharmaceutical Research; (1989); pp. 449-457; vol. 6(6).
Andriol® Testocaps™; Consumer Medicine Information; (Sep. 2003).
Andriolo® Testocaps®; Product Information; (Oct. 28, 2015); 8 pages,.
Androderm® Product Label and Medication Guide; (1995); Labeler—Watson Pharma, Inc.; Revised Nov. 2013; 23 pages.
Androgel® Product Label and Medication Guide; (May 2013); Labeler—AbbVie Inc.; Revised Oct. 2013; 28 pages.

(Continued)

*Primary Examiner* — James D. Anderson
(74) *Attorney, Agent, or Firm* — Michael R. Schramm

(57) ABSTRACT

Disclosed are bioavailable solid state (17-β)-Hydroxy-4-Androsten-3-one esters suitable for pharmaceutical uses and administration to mammals in need of (17-β)-Hydroxy-4-Androsten-3-one. Pharmaceutical compositions and the dosage forms of the bioavailable solid state (17-β)-Hydroxy-4-Androsten-3-one esters can be used to treat any condition associated with testosterone deficiency, including complete absence of endogenous testosterone in male or female subjects.

20 Claims, 8 Drawing Sheets

(56) References Cited

U.S. PATENT DOCUMENTS

| | | |
|---|---|---|
| 4,880,634 A | 11/1989 | Speiser |
| 4,895,726 A | 1/1990 | Curtet et al. |
| 4,897,269 A | 1/1990 | Mezei |
| 4,900,734 A | 2/1990 | Maxson et al. |
| 4,925,672 A | 5/1990 | Gremm |
| 4,944,949 A | 7/1990 | Story |
| 4,961,890 A | 10/1990 | Boyer |
| 4,963,540 A | 10/1990 | Maxson et al. |
| 4,994,439 A | 2/1991 | Longenecker et al. |
| 5,023,108 A | 6/1991 | Bageria et al. |
| 5,026,560 A | 6/1991 | Makino et al. |
| 5,035,891 A | 7/1991 | Runkel et al. |
| 5,045,321 A | 9/1991 | Makino et al. |
| 5,057,319 A | 10/1991 | Gottwald et al. |
| 5,071,643 A | 12/1991 | Yu et al. |
| 5,091,187 A | 2/1992 | Haynes |
| 5,091,188 A | 2/1992 | Haynes |
| 5,093,132 A | 3/1992 | Makino et al. |
| 5,104,656 A | 4/1992 | Seth et al. |
| 5,120,710 A | 6/1992 | Liedtke |
| 5,140,021 A | 8/1992 | Maxson et al. |
| 5,145,684 A | 9/1992 | Liversidge |
| 5,152,997 A | 10/1992 | Ebert et al. |
| 5,206,219 A | 4/1993 | Desai |
| 5,244,925 A | 9/1993 | Wretlind |
| 5,252,339 A | 10/1993 | Cristofori et al. |
| 5,270,005 A | 12/1993 | Raible |
| 5,270,055 A | 12/1993 | Moest |
| 5,300,529 A | 4/1994 | Narayanan |
| 5,340,589 A | 8/1994 | Stetsko et al. |
| 5,342,625 A | 8/1994 | Hauer et al. |
| 5,350,741 A | 9/1994 | Takada |
| 5,364,632 A | 11/1994 | Benita et al. |
| 5,374,446 A | 12/1994 | Ferenz et al. |
| 5,376,688 A | 12/1994 | Morton et al. |
| 5,380,535 A | 1/1995 | Gever et al. |
| 5,384,133 A | 1/1995 | Boyes et al. |
| 5,389,382 A | 2/1995 | List |
| 5,403,593 A | 4/1995 | Royce |
| 5,433,959 A | 7/1995 | Makino et al. |
| 5,444,041 A | 8/1995 | Owen |
| 5,500,224 A | 3/1996 | Vranckx et al. |
| 5,532,002 A | 7/1996 | Story |
| 5,539,000 A | 7/1996 | Leonard |
| 5,543,393 A | 8/1996 | Kim et al. |
| 5,545,628 A | 8/1996 | DeBoeck et al. |
| 5,560,931 A | 10/1996 | Elckhoff et al. |
| 5,571,533 A | 11/1996 | Santus et al. |
| 5,571,536 A | 11/1996 | Eickhoff et al. |
| 5,573,783 A | 11/1996 | Desieno et al. |
| 5,589,455 A | 12/1996 | Woo |
| 5,589,513 A | 12/1996 | Magyar et al. |
| 5,593,971 A | 1/1997 | Tschollar et al. |
| 5,614,491 A | 3/1997 | Walch et al. |
| 5,616,330 A | 4/1997 | Kaufman et al. |
| 5,622,721 A | 4/1997 | Dansereau et al. |
| 5,624,687 A | 4/1997 | Yano et al. |
| 5,626,869 A | 5/1997 | Nyqvist et al. |
| 5,629,021 A | 5/1997 | Wright |
| 5,633,015 A | 5/1997 | Gillis et al. |
| 5,633,226 A | 5/1997 | Owen |
| 5,635,520 A | 6/1997 | Uda |
| 5,639,474 A | 6/1997 | Woo |
| 5,639,478 A | 6/1997 | Makino et al. |
| 5,639,724 A | 6/1997 | Cavanak |
| 5,645,856 A | 7/1997 | Lacy et al. |
| 5,646,109 A | 7/1997 | Owen et al. |
| 5,653,987 A | 8/1997 | Modi et al. |
| 5,656,277 A | 8/1997 | Berlati et al. |
| 5,656,289 A | 8/1997 | Cho et al. |
| 5,665,379 A | 9/1997 | Herslof et al. |
| 5,681,584 A | 10/1997 | Savatano et al. |
| 5,686,105 A | 11/1997 | Kelm et al. |
| 5,688,761 A | 11/1997 | Owen et al. |
| 5,698,155 A | 12/1997 | Grosswald et al. |
| 5,707,648 A | 1/1998 | Yiv |
| 5,714,477 A | 2/1998 | Einarsson |
| 5,726,181 A | 3/1998 | Hausheer et al. |
| 5,731,355 A | 3/1998 | Jones et al. |
| 5,736,161 A | 4/1998 | Garces et al. |
| 5,741,512 A | 4/1998 | Hauer et al. |
| 5,741,822 A | 4/1998 | Yesair |
| 5,747,066 A | 5/1998 | Pittrof et al. |
| 5,756,450 A | 5/1998 | Hahn et al. |
| 5,759,997 A | 6/1998 | Cavanak |
| 5,766,629 A | 6/1998 | Cho et al. |
| 5,767,069 A | 6/1998 | Ko et al. |
| 5,776,495 A | 7/1998 | Duclos et al. |
| 5,795,883 A | 8/1998 | Hesch et al. |
| 5,798,333 A | 8/1998 | Sherman |
| 5,811,120 A | 9/1998 | Gibson et al. |
| 5,817,320 A | 10/1998 | Stone |
| 5,827,536 A | 10/1998 | Laruelle |
| 5,846,971 A | 12/1998 | Sangekar et al. |
| 5,853,748 A | 12/1998 | New |
| 5,855,905 A | 1/1999 | Oettel et al. |
| 5,858,398 A | 1/1999 | Cho |
| 5,858,401 A | 1/1999 | Bhalani et al. |
| 5,866,159 A | 2/1999 | Hauer et al. |
| 5,874,418 A | 2/1999 | Stella et al. |
| 5,880,148 A | 3/1999 | Edgar et al. |
| 5,883,109 A | 3/1999 | Gregg et al. |
| 5,891,469 A | 4/1999 | Amselem |
| 5,891,845 A | 4/1999 | Myers |
| 5,916,589 A | 6/1999 | Hauer et al. |
| 5,922,355 A | 7/1999 | Parikh et al. |
| 5,948,773 A | 9/1999 | Akiyama et al. |
| 5,948,825 A | 9/1999 | Takahshi et al. |
| 5,962,014 A | 10/1999 | Hauer et al. |
| 5,962,017 A | 10/1999 | Hauer et al. |
| 5,965,161 A | 10/1999 | Oshlack |
| 5,976,574 A | 11/1999 | Gordon |
| 5,981,479 A | 11/1999 | Ko et al. |
| 5,981,586 A | 11/1999 | Pershadsingh |
| 5,989,583 A | 11/1999 | Amselem |
| 5,993,880 A | 11/1999 | Frost et al. |
| 6,007,840 A | 12/1999 | Hauer et al. |
| 6,008,192 A | 12/1999 | Al-Razzak et al. |
| 6,013,665 A | 1/2000 | DeMichele et al. |
| 6,017,560 A | 1/2000 | Makino et al. |
| 6,022,852 A | 2/2000 | Klokkers et al. |
| 6,024,978 A | 2/2000 | Hauer et al. |
| 6,027,747 A | 2/2000 | Terracol et al. |
| 6,042,847 A | 3/2000 | Kere et al. |
| 6,046,177 A | 4/2000 | Stella et al. |
| 6,057,339 A | 5/2000 | Gregg |
| 6,066,653 A | 5/2000 | Gregg et al. |
| 6,074,670 A | 6/2000 | Stamm et al. |
| 6,086,376 A | 7/2000 | Moussa et al. |
| 6,096,338 A | 8/2000 | Lacy et al. |
| 6,123,962 A | 9/2000 | Makino et al. |
| 6,160,007 A | 12/2000 | DeMichele et al. |
| 6,174,547 B1 | 1/2001 | Dong et al. |
| 6,180,138 B1 | 1/2001 | Engh et al. |
| 6,189,486 B1 | 2/2001 | Lindholm |
| 6,193,985 B1 | 2/2001 | Sonne |
| 6,221,395 B1 | 4/2001 | Maggi et al. |
| 6,224,840 B1 | 5/2001 | Kim et al. |
| 6,228,399 B1 | 5/2001 | Parikh et al. |
| 6,228,400 B1 | 5/2001 | Lee et al. |
| 6,248,363 B1 | 6/2001 | Patel et al. |
| 6,255,100 B1 | 7/2001 | Ko et al. |
| 6,267,985 B1 | 7/2001 | Chen et al. |
| 6,287,594 B1 | 9/2001 | Wilson |
| 6,294,192 B1 | 9/2001 | Patel et al. |
| 6,296,876 B1 | 10/2001 | Odidi et al. |
| 6,299,904 B1 | 10/2001 | Shimizu et al. |
| 6,303,662 B1 | 10/2001 | Nagahama et al. |
| 6,306,825 B1 | 10/2001 | Cavanak |
| 6,309,663 B1 | 10/2001 | Patel et al. |
| 6,328,993 B1 | 12/2001 | Linder et al. |
| 6,328,994 B1 | 12/2001 | Shimizu et al. |
| 6,340,471 B1 | 1/2002 | Kershman et al. |
| 6,342,246 B2 | 1/2002 | Johnson et al. |

(56) References Cited

U.S. PATENT DOCUMENTS

| | | |
|---|---|---|
| 6,361,796 B1 | 3/2002 | Rudnic et al. |
| 6,368,634 B1 | 4/2002 | Remon |
| 6,379,705 B1 | 4/2002 | Mendes et al. |
| 6,383,471 B1 | 5/2002 | Chen et al. |
| 6,383,510 B1 | 5/2002 | Linder et al. |
| 6,383,517 B1 | 5/2002 | Qiu et al. |
| 6,391,342 B1 | 5/2002 | Henriksen et al. |
| 6,432,445 B1 | 8/2002 | Ambhul et al. |
| 6,444,225 B1 | 9/2002 | Sherman |
| 6,447,806 B1 | 9/2002 | Gassmann et al. |
| 6,451,339 B2 | 9/2002 | Patel et al. |
| 6,455,518 B2 | 9/2002 | Zenke et al. |
| 6,458,373 B1 | 10/2002 | Lambert et al. |
| 6,458,383 B2 | 10/2002 | Chen et al. |
| 6,465,016 B2 | 10/2002 | Parikh et al. |
| 6,468,559 B1 | 10/2002 | Chen et al. |
| 6,475,519 B1 | 11/2002 | Minzer et al. |
| 6,503,894 B1 | 1/2003 | Dudley et al. |
| 6,531,139 B1 | 3/2003 | Gao et al. |
| 6,569,463 B2 | 5/2003 | Patel et al. |
| 6,589,552 B2 | 7/2003 | Stamm et al. |
| 6,589,562 B1 | 7/2003 | Shefer et al. |
| 6,623,755 B2 | 9/2003 | Chen et al. |
| 6,630,134 B1 | 10/2003 | Klein |
| 6,652,880 B1 | 11/2003 | Aylwin et al. |
| 6,660,286 B1 | 12/2003 | Lambert et al. |
| 6,665,880 B2 | 12/2003 | Pope |
| 6,667,048 B1 | 12/2003 | Lambert et al. |
| 6,692,766 B1 | 2/2004 | Rubinstein et al. |
| 6,696,482 B2 | 2/2004 | Shemoy et al. |
| 6,720,001 B2 | 4/2004 | Chen et al. |
| 6,737,082 B1 | 5/2004 | Dander |
| 6,761,903 B2 | 7/2004 | Chen et al. |
| 6,881,745 B2 | 4/2005 | Hayes et al. |
| 6,887,493 B2 | 5/2005 | Shefer et al. |
| 6,913,244 B1 | 7/2005 | Atkinson et al. |
| 6,923,988 B2 | 8/2005 | Patel et al. |
| 6,977,083 B1 | 12/2005 | Huebler et al. |
| 6,982,281 B1 | 1/2006 | Chen et al. |
| 7,025,979 B2 | 4/2006 | Neischlag et al. |
| 7,138,389 B2 | 11/2006 | Amory et al. |
| 7,374,779 B2 | 5/2008 | Chen et al. |
| 7,658,944 B2 | 2/2010 | Holm et al. |
| 7,718,640 B2 | 5/2010 | Hubler et al. |
| 8,241,664 B2 | 8/2012 | Dudley et al. |
| 8,338,395 B2 | 12/2012 | Hubler et al. |
| 8,492,369 B2 | 7/2013 | Dudley et al. |
| 8,778,922 B2 | 7/2014 | Giliyar et al. |
| 8,828,428 B1 | 9/2014 | Dudley et al. |
| 9,034,858 B2 | 5/2015 | Giliyar et al. |
| 9,205,057 B2 | 12/2015 | Giliyar et al. |
| 9,498,485 B2 | 11/2016 | Patel et al. |
| 9,757,389 B2 | 9/2017 | Patel et al. |
| 11,298,365 B2 * | 4/2022 | Patel ................. A61K 9/16 |
| 2001/0018069 A1 | 8/2001 | Johnson et al. |
| 2002/0006443 A1 | 1/2002 | Curatolo et al. |
| 2002/0013304 A1 | 1/2002 | Wilson et al. |
| 2002/0058066 A1 | 5/2002 | Tomohira et al. |
| 2002/0068693 A1 | 6/2002 | Jeng et al. |
| 2002/0102301 A1 | 8/2002 | Schwarz |
| 2002/0103139 A1 | 8/2002 | Weisspapir et al. |
| 2002/0115648 A1 | 8/2002 | Carruthers |
| 2002/0183296 A1 | 12/2002 | Dudley |
| 2003/0022875 A1 | 1/2003 | Wilson et al. |
| 2003/0072798 A1 | 4/2003 | Schwarz et al. |
| 2003/0077297 A1 | 4/2003 | Chen et al. |
| 2003/0082215 A1 | 5/2003 | Lemut et al. |
| 2003/0104048 A1 | 6/2003 | Patel et al. |
| 2003/0180352 A1 | 9/2003 | Patel et al. |
| 2003/0181431 A1 | 9/2003 | Hodgen |
| 2003/0186892 A1 | 10/2003 | Taneja |
| 2003/0228358 A1 | 12/2003 | Perlman et al. |
| 2003/0235595 A1 | 12/2003 | Chen et al. |
| 2003/0236236 A1 | 12/2003 | Chen et al. |
| 2004/0002445 A1 | 1/2004 | Taneja |
| 2004/0002482 A1 | 1/2004 | Dudley et al. |
| 2004/0048896 A1 | 3/2004 | Phillips |
| 2004/0072810 A1 | 4/2004 | Masini-Eteve et al. |
| 2004/0127476 A1 | 7/2004 | Kershman et al. |
| 2005/0031693 A1 | 2/2005 | Babcock et al. |
| 2005/0032762 A1 | 2/2005 | Hubler et al. |
| 2005/0070516 A1 | 3/2005 | Wilson |
| 2005/0080075 A1 | 4/2005 | Nichols et al. |
| 2005/0096296 A1 | 5/2005 | Fikstad et al. |
| 2005/0096365 A1 | 5/2005 | Fikstad et al. |
| 2005/0100608 A1 | 5/2005 | Ebert |
| 2005/0101517 A1 | 5/2005 | De Nijs et al. |
| 2005/0171193 A1 | 8/2005 | Chen et al. |
| 2005/0176692 A1 | 8/2005 | Amory et al. |
| 2005/0209345 A1 | 9/2005 | Charman |
| 2005/0220825 A1 | 10/2005 | Funke et al. |
| 2005/0269251 A1 | 12/2005 | Cork |
| 2005/0287203 A1 | 12/2005 | De Nijs et al. |
| 2005/0287212 A1 | 12/2005 | Dong et al. |
| 2006/0003002 A1 | 1/2006 | Fikstad et al. |
| 2006/0034937 A1 | 2/2006 | Patel |
| 2006/0051406 A1 | 3/2006 | Parmar |
| 2006/0106004 A1 | 5/2006 | Brody et al. |
| 2006/0142257 A1 | 6/2006 | Nieschlag |
| 2007/0110777 A1 | 5/2007 | Joabsson et al. |
| 2007/0134336 A1 | 6/2007 | Worle et al. |
| 2007/0154533 A1 | 7/2007 | Dudley |
| 2007/0232548 A1 | 10/2007 | Taneja |
| 2008/0020053 A1 | 1/2008 | Persson et al. |
| 2008/0217692 A1 | 9/2008 | Anderson et al. |
| 2008/0317844 A1 | 12/2008 | Dudley et al. |
| 2008/0317850 A1 | 12/2008 | Hewitt et al. |
| 2009/0074859 A1 | 3/2009 | Patel |
| 2010/0036084 A1 | 2/2010 | Langer et al. |
| 2010/0136105 A1 | 6/2010 | Chen et al. |
| 2010/0137271 A1 | 6/2010 | Chen et al. |
| 2010/0148675 A1 | 6/2010 | Meijer et al. |
| 2010/0173882 A1 | 7/2010 | Giliyar et al. |
| 2011/0039814 A1 | 2/2011 | Huatan et al. |
| 2011/0142945 A1 | 6/2011 | Chen et al. |
| 2011/0244048 A1 | 10/2011 | Amiji et al. |
| 2011/0251167 A1 | 10/2011 | Dudley et al. |
| 2011/0263552 A1 | 10/2011 | Dhingra et al. |
| 2012/0135074 A1 | 5/2012 | Giliyar et al. |
| 2012/0148675 A1 | 6/2012 | Chickmath et al. |
| 2012/0244215 A1 | 9/2012 | Giliyar et al. |
| 2012/0322780 A1 | 12/2012 | Giliyar et al. |
| 2013/0022674 A1 | 1/2013 | Dudley et al. |
| 2013/0052263 A1 | 2/2013 | Fikstad et al. |
| 2013/0225544 A1 | 8/2013 | Nacheagari et al. |
| 2013/0243689 A1 | 9/2013 | Amiji et al. |
| 2014/0249124 A1 | 9/2014 | Dudley et al. |
| 2014/0303130 A1 | 10/2014 | Giliyar et al. |
| 2014/0357586 A1 | 12/2014 | Patel |
| 2015/0038475 A1 | 2/2015 | Chickmath et al. |
| 2015/0224059 A1 | 8/2015 | Giliyar |
| 2015/0273067 A1 | 10/2015 | Patel |

FOREIGN PATENT DOCUMENTS

| | | |
|---|---|---|
| CN | 101217963 | 7/2008 |
| DE | 10108614 | 9/2002 |
| EP | 0036145 | 5/1985 |
| EP | 0184942 | 6/1986 |
| EP | 0537070 | 4/1993 |
| EP | 0981328 | 3/2000 |
| EP | 0988858 | 3/2000 |
| EP | 0724877 | 6/2000 |
| EP | 1103252 | 5/2001 |
| EP | 0904064 | 10/2001 |
| EP | 1624855 | 2/2006 |
| EP | 1879456 | 1/2008 |
| EP | 2000130 | 12/2008 |
| EP | 2558073 | 10/2011 |
| EP | 2985026 | 2/2016 |
| FR | 2647346 | 11/1990 |
| FR | 2758459 | 7/1998 |
| GB | 1264677 | 2/1973 |
| GB | 2098865 | 12/1982 |

(56) References Cited

FOREIGN PATENT DOCUMENTS

| | | |
|---|---|---|
| GB | 2228198 | 8/1990 |
| JP | S52-66616 | 6/1977 |
| JP | S57-70824 | 5/1982 |
| JP | 01139526 | 6/1989 |
| JP | 5194209 | 8/1993 |
| JP | 07041422 | 2/1995 |
| JP | H07-508724 | 9/1995 |
| JP | 09241152 | 9/1997 |
| JP | 11049664 | 2/1999 |
| JP | 11152227 | 6/1999 |
| JP | 2001508445 | 6/2001 |
| JP | 2001514626 | 9/2001 |
| JP | 2002510311 | 4/2002 |
| JP | 2002520377 | 7/2002 |
| JP | 2003500368 | 1/2003 |
| JP | 2008540451 | 11/2008 |
| RU | 2354381 C2 | 10/2009 |
| WO | WO 82/01649 | 5/1982 |
| WO | WO 84/02076 | 6/1984 |
| WO | WO 88/00059 | 1/1988 |
| WO | WO 92/18147 | 10/1992 |
| WO | WO 93/02664 | 2/1993 |
| WO | WO 93/06921 | 4/1993 |
| WO | WO 93/25192 | 12/1993 |
| WO | WO 94/08610 | 4/1994 |
| WO | WO 94/25068 | 11/1994 |
| WO | WO 95/01785 | 1/1995 |
| WO | WO 95/01786 | 1/1995 |
| WO | WO 95/24893 | 9/1995 |
| WO | WO 95/34287 | 12/1995 |
| WO | WO 96/17597 | 6/1996 |
| WO | WO 97/04749 | 2/1997 |
| WO | WO 97/40823 | 11/1997 |
| WO | WO 97/48382 | 12/1997 |
| WO | WO 98/00116 | 1/1998 |
| WO | WO 98/30205 | 7/1998 |
| WO | WO 98/33512 | 8/1998 |
| WO | WO 98/38984 | 9/1998 |
| WO | WO 98/50077 | 11/1998 |
| WO | WO 98/56357 | 12/1998 |
| WO | WO 99/00111 | 1/1999 |
| WO | WO 99/29300 | 6/1999 |
| WO | WO 99/40904 | 8/1999 |
| WO | WO 99/44584 | 9/1999 |
| WO | WO 99/48498 | 9/1999 |
| WO | WO 2000/003753 | 1/2000 |
| WO | WO 2000/016749 | 3/2000 |
| WO | WO 2000/025772 | 5/2000 |
| WO | WO 2000/037057 | 6/2000 |
| WO | WO 2000/050007 | 8/2000 |
| WO | WO 2000/057859 | 10/2000 |
| WO | WO 2000/057918 | 10/2000 |
| WO | WO 2000/059482 | 10/2000 |
| WO | WO 2000/059512 | 10/2000 |
| WO | WO 2000/071163 | 11/2000 |
| WO | WO 2000/072825 | 12/2000 |
| WO | WO 2000/076482 | 12/2000 |
| WO | WO 01/01960 | 1/2001 |
| WO | WO 01/12155 | 2/2001 |
| WO | WO 2001/021154 | 3/2001 |
| WO | WO 01/28555 | 4/2001 |
| WO | WO 01/37808 | 5/2001 |
| WO | WO 2001/049262 | 7/2001 |
| WO | WO 02/39983 | 5/2002 |
| WO | WO 03/068186 | 8/2003 |
| WO | WO 2004/087052 | 10/2004 |
| WO | WO 2004/105694 | 12/2004 |
| WO | WO 2005/041929 | 5/2005 |
| WO | WO 2006/013369 | 2/2006 |
| WO | WO 2006/113505 | 10/2006 |
| WO | WO 2006113505 A2 | 10/2006 |
| WO | WO 2006/119498 | 11/2006 |
| WO | WO 2007/018943 | 2/2007 |
| WO | WO 2007/100614 | 9/2007 |
| WO | WO 2010/081032 | 7/2010 |
| WO | WO 2010/102737 | 9/2010 |
| WO | WO 2011/082384 | 7/2011 |
| WO | WO 2011/129812 | 10/2011 |
| WO | WO 2012/075081 | 7/2012 |

OTHER PUBLICATIONS

Atkinson et al.; "Long Term Experience with Testosterone Replacement Through Scrotal Skin; In: Nieschlag et al. (eds) Testosterone: Action, Deficiency and Substitution;" (1998); pp. 365-388; Ch. 13; < doi: https://doi.org/10.1007/978-3-642-72185-4_13 >.

Aungst; "Intestinal Permeation Enhancers;" Journal of Pharmaceutical Sciences; (2000); pp. 429-442; vol. 89(4).

Baert et al.; "Analytical, Biopharmaceutical and Regulatory Evaluation of Topical Testosterone Preparations;" European Journal of Pharmaceutics and Biopharmaceutics; (2009); pp. 275-281; vol. 72; <doi: 10.1016/j.ejpb.2008.10.014 >.

Bagchus et al.; "Important Effect of Food on the Bioavailability of Oral Testosterone Undecanoate;" Pharmacotherapy: (2003); pp. 319-325; vol. 23(3).

Baluom et al.: "The Importance of Intestinal Residence Time of Absorption Enhancer on Drug Implication on Formulative Considerations;" International Journal of Pharmaceutics; (1998), pp. 21-30; vol. 176.

Bates et al.; "Bioavailability of Micronized Griseofulvin from Corn Oil-in-Water Emulsion, Aqueous Suspension, and Commercial Tablet Dosage Forms in Humans;" Journal of Pharmaceutical Sciences; (1975); pp. 793-797; vol. 64(5).

Beatch et al.; "Ventricular Fibrillation, an Uncontrolled Arrhythmia Seeking New Targets;" Drug Development Research Journal; (2002); pp. 45-52; vol. 55.

Bernkop-Schnurch; "The Use of Inhibitory Agents to Overcome the Enzymatic Barrier to Orally Administered Therapeutic Peptides and Proteins;" Journal of Controlled Release; (Apr. 1998); pp. 1-16; vol. 52(1-2).

Bhargava et al.; "Using Microemulsions for Drug Delivery;" Pharmaceutical Technology; (Mar. 1987); pp. 46-53.

Brittain, ed.; "Polymorphism is Pharmaceutical Solids;" Drugs and Pharmaceutical Sciences; Second Edition: (2009); 229 pages; vol. 192.

Burbello et al.; Sovremennye Lekarstvennyesredstava S-Pb Neva; (2004); p. 567.

Cantrill; "Which Testosterone Replacement Therapy;" Clinical Endocrinology Journal; (1984); pp. 97-107; vol. 21.

Charman et al.; "Physicochemical and Physiological Mechanisms for the Effects of Food on Drug Absorption: The Role of Lipids and pH;" Journal of Pharmaceutical Sciences; (1997): pp. 269-282; vol. 86(3).

Constantidides; "Lipid Microemulsion for Improving Drug Dissolution and Oral Absorption: Physical and Biopharmaceutical Aspect;" Pharmaceutical Research; (1995); pp. 1561-1572; vol. 12(11).

Depo-Testosterone® Product Label and Medication Guide: (Sep. 2006); Labeler—Pharmacia & Upjohn Company; Revised Aug. 2013; 12 pages.

Emulsion; IUPAC Compendium of Chemical Terminology; 2nd Ed.; (1997).

Frey et al.; "Bioavailability of Oral Testosterone in Males;" European Journal of Pharmacology; (1979); pp. 345-349; vol. 16.

GENNARO; "Surfactant Properties in Solution and Micelle Formation, Colloidal Dispersions;" Remington's Pharmaceutical Sciences; (1985); pp. 293-300; Chapter 20.

Goncharova et al.; "Preparation of Testosterone Esters:" Pharmaceutical Chemistry Journal; (Jul. 1973); pp. 427-428; vol. 7(7).

Gooren; "A Ten-year Safety Study of the Oral Androgen Testosterone Undecanoate;" Journal of Andrology: (1994); pp. 212-215; vol. 15(3).

Grahame-Smith et al; The Oxford Textbook of Clinical Pharmacology and Drug Therapy: (1992); pp. 25, 136-137; $2^{nd}$ Edition; M. Meditsina Publishers; (English version included pp. 9-12, 122-124).

Healthline; "What are the symptoms of Hypogonadism?"; 1 page; [Internet]; [Retrieved on Apr. 1, 2014] [Retrieved from <URL: http://www.healthline.com/health/hypogonadism#Overview1 >].

(56) References Cited

OTHER PUBLICATIONS

Hong, B.S., et al.; "Recent trends in the treatment of testosterone deficiency syndrome;" International Journal of Urology; (2007); pp. 981-985; vol. 14: The Japanese Urological Association; <doi:10.1111/j.1442-2042.2007.01882.x >.

Hörter et al.; "Influence of Physiochemical Properties on Dissolution of Drugs in the Gastrointestinal Tract;" Advanced Drug Delivery Reviews; (1997); pp. 3-14; vol. 25.

Houwing et al.; "Pharmacokinetic Study in Women of Three Different Doses of a New Formulation of Oral Testosterone Undecanoate, Andriol® Testocaps™;" Pharmacotherapy; (2003); pp. 1257-1265; vol. 23(10).

Humberstone et al.; "Lipid-based Vehicles for the Oral Delivery of Poorly Water Soluble Drugs:" Advanced Drug Delivery Reviews: (1997) pp. 103-128.

Hutchison; "Digestible Emulsions and Microemulsions for Optimum Oral Delivery of Hydrophobic Drugs;" Bulletin Technique Gattefosse; (1994); pp. 67-74: vol. 87.

Javanbakht et al; "Pharmacokinetics of a Novel Testosterone Matrix Transdermal System In Health, Premenopausal Women and Women Infected with the Human Immunodeficiency Virus 1;" Journal of Clinical Endocrinology & Metabolism; (2000); pp. 2395-2401; vol. 85(7).

Johnson; "Gastrointestinal Physiology;" Department of Physiology; University of Texas Medical School; (1997); pp. 25-26, 93-106, 133-134, 136-137; Houston, Texas.

Julien; "A Concise Nontechnical Guide to the Actions, Uses, and Side3 Effects of Psychoactive Drugs;" A Primer of Drug Action; (2001); pp. 5-6; $9^{th}$ Edition.

Kalinchenko; "Testosterone—King Hormones, hormones kings:" The Journal; Sex and Life; (2004); pp. 12-22: [Retrieved on Mar. 26, 2010]; [Retrieved from <URL: http://www.laz.med.ru/interesting/publications/testosterone.html >].

Köhn et al.; "A New Oral Testosterone Undecanoate Formulation;" World Journal of Urology: (Nov. 2003); pp. 311-315; vol. 21(5); <doi: 10.1007/s00345-003-0372-x>.

LANGER; "New Methods of Drug Delivery;" Science: (Sep. 1990); pp. 1527-1533; vol. 249(4976).

Lecluyse et al.; "In Vitro Models for Selection of Development Candidates. Permeability Studies to Define Mechanisms of Absorption Enhancement;" Advanced Drug Delivery Reviews; (1997); pp. 163-183; vol. 23.

Leichtnam et al.; "Testosterone Hormone Replacement Therapy: State-of-the-Art and Emerging Technology;" Pharmaceutical Research; (2006); pp. 1117-1132; vol. 23(6).

LGC; Reference Standard Testosterone Undecanoate; Certificate of Analysis; (Jul. 5, 2015); 6 pages; LGC GmBH; Germany.

Lopez-Berestein et al. (Eds.); Liposomes in the Therapy of Infectious Disease and Cancer; (1989); pp. 353-365; Liss; New York.

MacGregor et al.; "Influence of Lipolysis on Drug Absorption From the Gastro-Intestinal Tract;" Advanced Drug Delivery Reviews; (1997); pp. 33-46; vol. 25.

Maisey et al.; "Clinical Efficacy of Testosterone Undecanoate in Male Hypogonadism;" Clinical Endocrinology; (1981); pp. 625-629; vol. 14.

McAuley et al; "Oral Administration of Micronized Progesterone: A Review and More Experience;" Pharmacotherapy; (May 1996); pp. 453-457; vol. 16(3).

Meinert et al.; Clinical Trials: Design, Conduct and Analysis (Monographs in Epidemiology and Biostatistics; (1986); vol. 8.

Merck Index, "Alpha Tocopherol;" Monograph 09571; (2001-2004); Merck & Co. Inc.

Merck Index; "Amiodarone;" Monograph 504; (1996); p. 84; $12^{th}$ Edition; Merck & Co., Inc.

Merck Index; "Carvedilol"; Monograph 01888; (2001-2004); Merck & Co., Inc.

Merck Index; "Fenofibrate;" Monograph 3978; (2006); pp. 679-680; $14^{th}$ Edition, Merck & Co., Inc.

Merck Index; "Risperidone;" Monograph 08316; (2001-2004); Merck & Co., Inc.

Merck Index; "Shellac:" Monograph 8623: (1996); p. 8526; $12^{th}$ Edition.

Merck Index; "Testosterone;" Monograph 9322; (1996): p. 9326; $12^{th}$ Edition; Merck & Co., Inc.

Merck Index; "Vitamin E;" Monograph 10021; (2006); p. 1726; $14^{th}$ Edition; Merck & Co., Inc.

Merck Index: "Vitamin E" and "Vitamin E Acetate;" Monographs 9931 and 9932; (1989): pp. 1579-1580; $11^{th}$ Edition; Merck & Co., Inc.

Merck Index; "Ziprasidone;" Monograph 10224;(2001-2004); Merck & Co., Inc.

Merriam-Webster Dictionary; "Granule;" [Retrieved Dec. 17, 2009] [Retrieved from <URL: http://www.mw.com/dictionary/granule >].

Mittal et al.; "The Wide World of Micelles;" In: International Symposium on Micellization, Solubilization, and Microemulsions, $7^{th}$ Northeastern Regional Meeting of the American Society; Albany, New York; (1976); pp. 1-21; vol. I <ISBN: 0-306-31023-6(v.1) >.

Moellering; "Vancomycin: A 50-Year Reassessment;" Clinical Infectious Diseases; (2006); pp. S3-S4; vol. 42.

Muranishi; "Absorption Enhancers;" Critical Reviews in Therapeutic Drug Carrier Systems, (1990): pp. 1-33; vol. 7(1).

Muranishi; "Potential Absorption of Heparin from the Small Intestine and the Large Intestine in the Presence of Monoolein Mixed Micelles;" Chemical and Pharmaceutical Bulletin Journal: (1977); pp. 1159-1161; vol. 24(5).

Nieschlag et al.; "Plasma Androgen Levels in Men after Oral Administration of Testosterone or Testosterone Undecanoate;" Acta Endocrinologica: (1975); pp. 366-374; vol. 79(2); (Abstract).

Noguchi et al; "The Effect of Drug Lipophilicity and Lipid Vehicles on the Lymphatic Absorption of Various Testosterone Esters;" International Journal of Pharmaceutics; (May 1985); pp. 173-184; vol. 24(2-3).

Osol (Ed.): "Emulsions:" Remington's Pharmaceutical Sciences; (1975); pp. 327-339. 1452-1456; $15^{th}$ Edition.

Perchersky et al. "Androgen Administration in Middle-Aged and Aging Men: Effects of Oral Testosterone Undecanoate on Dihydrotestosterone, Oestradiol and Prostate Volume;" International Journal of Andrology; (2002): pp. 119-125: vol. 25.

Peterson et al.; "Iterative High-Throughput Polymorphism Studies on Acetaminophen and Experimentally Derived Structure Form III:" Journal of American Chemical Society: JACS Communications: (2002); pp. 10958-10959; vol. 124.

Pfeil et al.; "Current and Future Testosterone Delivery Systems for Treatment of the Hypogonadal Male;" Expert Opinion on Drug Delivery; (Apr. 2008): pp. 471-481; vol. 5, No. 4; <doi: 10.1517/17425247.5343471 >.

Pouton; "Formulation of Self-Emulsifying Drug Delivery Systems:" Advanced Drug Delivery Reviews; (1997); pp. 47-58; vol. 25.

Reymond et al.; "In Vivo Model for Ciclosporin Intestinal Absorption in Lipid Vehicles;" Pharmaceutical Research: (1988); pp. 677-679; vol. 5(10).

S1 SEC Filing (Securities and Exchange Commission) for Clarus Therapeutics, Inc .; Filed May 23, 2014, with the Securities and Exchange Commission; 207 pages.

Saudek et al.; "A Preliminary Trial of the Programmable Implantable Medication System for Insulin Delivery;" The New England Journal of Medicine; (Aug. 31, 1989); pp. 574-579; vol. 321.

Schnabel et al.; "The Effect of Food Composition on Serum Testosterone Levels after Oral Administration of Adriol® Testocaps™;" Clinical Endocrinology: (2007); pp. 579-585; vol. 66(4).

Schott; "Comments on Hydrophile-Lipophile Balance Systems;" Journal of Pharmaceutical Sciences; (Jan. 1990); pp. 87-88; vol. 79(1); American Pharmaceutical Association.

sciencelab.com: "MSDS: Glyceryl Monooleate;" Material Safety Data Sheet; (Oct. 2005); 5 pages; <URL: www.sciencelab.com >.

Sefton; "Implantable Pumps;" Critical Reviews in Biomedical Engineering; (1987); pp. 201-240; vol. 14. No. 3; (Abstract); [Sourcelink] <URL: http://www.ncbi.nlm.nih.gov/pubmed/3297487 >.

Seidman et al.; "Testosterone Replacement Therapy for Hypogonadal Men with SSRI-Refractory Depression;" Journal of Affective Disorders; (1998); pp. 157-161; vol. 48.

(56) References Cited

OTHER PUBLICATIONS

Shackleford et al., "Contribution of Lymphatically Transported Testosterone Undecanoate to the Systemic Exposure of Testosterone after Oral Administration of two Andriol Formulations in Conscious Lymph Duct-Cannulated Dogs;" The Journal of Pharmacology and Experimental Therapeutics; (2003); pp. 925-933; vol. 306(3).
Shanghai Pi Chemicals Ltd.; "MSDS: Testosterone Undecanoate;" Material Safety Data Sheet; (2007); [Retrieved on Jun. 3, 2009] [retrieved from <URL: http://www.pipharm.com/product/msds-13457.pdf >].
Stedman's Medical Dictionary; "Dehydro-E-Epiandrosterone;" "Dehydroisoandroteron;" and "Steriod;" (1972); pp. 329, 1195-1197; $22^{nd}$ Edition; Williams & Wilkins Co.
Stedman's Medical Dictionary; "Hydroxy-Acid and Vitamin E;" (1973); pp. 595, 14000; $22^{nd}$ Edition; Williams & Wilkins Co.
Stedman's Medical Dictionary; "Surfactants;" (1972); p. 1225; $22^{nd}$ Edition; Williams & Wilkins Co.
Stedman's Medical Dictionary; "Surfactants:" (2006); $28^{th}$ Edition; Williams & Wilkins Co.
Swerdloff, et al; "Long Term Pharmaccokinetics of Transdermal Testosterone Gel in Hypogonadal Men;" Journal of Clinical Endocrinology & Metabolism; (2000); pp. 4500-4510; vol. 85.
Tarr et al.; "Enhanced Intestinal Absorption of Cyclosporine in Rats Through the Reduction of Emulsion Droplet Size;" Pharmaceutical Research; (1989); pp. 40-43; vol. 6(1).
Tauber et al.; "Absolute Bioavailability of Testosterone after Oral Administration of Testosterone-Undecanoate and Testosterone;" European Journal of Drug Metabolism and Pharmacokinetics: (1986); pp. 145-149; vol. 11(2). [Sourcelink] <URL: http://www.ncbi.nlm.nih.gov/pubmed/3770015>; [Abstract].
Temina et al.; "Diversity of the Fatty Acids of the *Nostoc* Species and their Statistical Analysis;" Microbiological Research: (2007); pp. 308-321; vol. 162; <doi: 10.1016/j.micres.2006.01.010 >.
Tenover; "The Androgen-Deficient Aging Male: Current Treatment Options;" Reviews in Urology; (2003): pp. S22-S28; vol. 5, Suppl. 1.

Testim® Product Label and Medication Guide: (Sep. 2009); Labeler—A-S Medications Solutions LLC, Revised Jun. 2013; 17 pages.
Torpac® Inc.; "Capsule Size Chart, Metric Table and English Table;" (2000); 3 pages; Torpac Inc., Fairfield, New Jersey: [Internet] [retrieved on Sep. 2014] [retrieved from <URL: www.torpac.com >].
Treat et al.; "Liposome Encapsulated Doxorubicin Preliminary Result of Phase I and Phase II Trials;" Liposomes in the Therapy of Infectious Diseases and Cancer; Lopez-Berestein and Fidler (Eds.); (1989); pp. 353-365; Liss, New York.
Tso, et al; "Intestinal Absorption and Lymphatic Transport of a High γ-Linolenic Acid Canola Oil in Lymph Fistula Sprague-Dawley Rats;" The Journal of Nutrition; (2002); pp. 218-221; American Society for Nutritional Sciences.
Wang, et al; "Long-term testosterone gel (AndroGel®) Treatment Maintains Beneficial Effects on Sexual Function and Mood, Lean and Fat Mass and Bone Mineral Density in Hypogonadal Men;" Journal of Clinical Endocrinology & Metabolism; (2004); pp. 2085-2098; vol. 89.
Wilson et al.; "The Behaviour of Fats and Oils in the Upper G.I. Tract;" Bulletin Technique Gattefosse; (1997); pp. 13-18; vol. 90.
Winne; "Dependence of Intestinal Absorption in Vivo on the Unstirred Layer;" Archives of Pharmacology; (1978); pp. 175-181; vol. 304.
Yassin et al.; "Long-Acting Testosterone Undecanoate for Parenteral Testosterone Therapy;" Therapy, Future Drugs; (2006); pp. 709-721; vol. 3(6).
Yin et al., "Dietary Fat Modulates the Testosterone Pharmacokinetics of a New Self-Emulsifying Formulation of Oral Testosterone Undecanoate in Hypogonadal Men;" Journal of Andrology; (Nov./Dec. 2012); pp. 1282-1290; vol. 33(6).
Yin et al.; "Reexamination of Pharmacokinetics of Oral Testosterone Undecanoate in Hypogonadal Men with a New Self-Emulsifying Formulation;" Journal of Andrology; (2012); pp. 190-201; vol. 33(2).
Zhi et al.; "Effects of Dietary Fat on Drug Absorption;" Clinical Pharmacology & Therapeutics; (Nov. 1995); pp. 487-491; vol. 58(5).

\* cited by examiner

BIOAVAILABLE SOLID STATE (17-β)-HYDROXY-4-ANDROSTEN-3-ONE ESTERS

CROSS REFERENCE TO RELATED APPLICATIONS

This nonprovisional utility patent application is a continuation of and claims the benefit under 35 USC § 120 to allowed co-pending U.S. application Ser. No. 16/849,957 filed Apr. 15, 2020, which is a continuation of and claims the benefit under 35 USC § 120 to co-pending U.S. application Ser. No. 16/273,911 filed Feb. 12, 2019, which is a continuation of and claims the benefit under 35 USC § 120 to co-pending U.S. application Ser. No. 15/672,185 filed Aug. 8, 2017, which is a continuation of and claims the benefit under 35 USC § 120 to co-pending U.S. application Ser. No. 15/276,389 filed Sep. 26, 2016 and since issued as U.S. Pat. No. 9,757,389 on Sep. 12, 2017, which is a continuation of and claims the benefit under 35 USC § 120 to co-pending U.S. application Ser. No. 14/839,820 filed Aug. 28, 2015 and since issued as U.S. Pat. No. 9,498,485 on Nov. 22, 2016, which claims the benefit under 35 USC § 119(e) of U.S. provisional application No. 62/043,337 filed Aug. 28, 2014, all of which are expressly incorporated herein in their entirety by this reference.

FIELD OF THE DISCLOSURE

Disclosed herein are solid state (17-β)-Hydroxy-4-Androsten-3-one esters suitable for pharmaceutical uses and administration to mammals (e.g., humans) in need of (17-β)-Hydroxy-4-Androsten-3-one.

BACKGROUND OF THE INVENTION

Different solid state forms of an ester of an active pharmaceutical ingredient (API) or esterified active pharmaceutical ingredient (EAPI) may possess different properties that can provide a formulation, in which the EAPI is included, with specific advantages, for example, by facilitating better processing or handling characteristics, changing the dissolution profile in a favorable direction, or improving stability (polymorph as well as chemical stability) and shelf-life. These variations in the properties of different solid state forms may also translate to benefits to a final dosage form, for instance, by providing or contributing to improved bioavailability. Different solid state forms of an EAPI may also give rise to a variety of polymorphs or crystalline forms, which may in turn provide additional opportunities to assess variations in the properties and characteristics of a solid EAPI.

An important characteristic of EAPI is that it's dissolution or release rate does not change substantially over time. Changes in dissolution or release rate of EAPI over time can result in otherwise identical products except for the solid state form (e.g., having the same EAPI, formulations components and amounts thereof), but different pharmacokinetic properties which can change or alter the efficacy or safety of a drug product.

The stability of EAPI in pharmaceutical preparations (e.g., compositions and unit dosage forms) is also important. For example, if the EAPI changes physical form (e.g., crystal form or amount thereof) in a pharmaceutical composition or unit dosage form, this can also affect pharmacokinetic properties and therefore related safety and efficacy parameters.

To be useful, the solid state has to be stable. A number of examples of bulk drug substance and pharmaceutical compositions/dosage forms that have changed physical form are known in the literature and have resulted in substantial problems to patients receiving these drugs. A well-known example is ritonavir which underwent a change in crystal form resulting in the product failing dissolution tests and being pulled off the market for a period of time (see Morissette et al. *Proc Natl Acad Sci USA*. 2003 Mar. 4; 100(5):2180-4). Other high profile cases include the recall of batches of Neupro (rotigotine) due to the appearance of a new polymorph in 2008, recall of 1.5 million tablets of warfarin in 2010 due to concerns over 2-propanol levels, which potentially could affect API crystallinity, and in 2010 the recall of 60 million tablets of Avalide over concerns in variability in the amounts of the less soluble polymorph of irbesartan in 2010. See Lee et al. *Annu. Rev. Chem. Biomol. Eng.* 2011, 2, 259-280.

Absorption of any prodrug such as an ester derivative of an API (EAPI) needs to be managed to provide adequate and sustained levels of the API derived from EAPI in vivo without adding any safety issues associated with the ester or its metabolite. Solubility, release, dissolution and partitioning of EAPI in a particular solvent is a function of lipophilicity and is related to solid state characteristics e.g., the physical form of the drug substance such as crystal form, solvation, whether or not amorphous material is present, etc. Therefore, the solid state physical form is one of the key properties with respect to ease of manufacturing, storage, and performance of the EAPI for enabling safe and effective levels of API.

Esters of (17-β)-Hydroxy-4-Androsten-3-one, which themselves are not thought to be biological active, are known to be transformed to the biologically active molecule ((17-β)-Hydroxy-4-Androsten-3-one in vivo (and other related metabolites like (17-β)-hydroxy-5α-androstan-3-one) and therefore can be used for treating patients in need of (17-β)-Hydroxy-4-Androsten-3-one treatment. However, inadequate solubility and/or release or dissolution or partitioning and/or physical stability of the solid state of the EAPI can result in poor bioavailability of (17-β)-Hydroxy-4-Androsten-3-one, a useful hormone for the treatment of several disease states such as male or female hypogonadism.

Several prodrug esters of (17-β)-Hydroxy-4-Androsten-3-one have been reported in the literature (Gooren U *Front Horm Res.* 2009; 37:32-5). However, in addition to overcoming solubility challenges with (17-β)-Hydroxy-4-Androsten-3-one esters, adequate absorption and conversion rate into the parent drug remain an important design element in preparing and identifying solid state esters of (17-β)-Hydroxy-4-Androsten-3-one. Approaches to date have failed to disclose or adequately characterize specific solid state (17-β)-Hydroxy-4-Androsten-3-one esters (i.e., the tridecanoate, tetradecanoate esters, and others), compositions and dosage forms having these esters and methods of their use that would be particularly useful in overcoming poor solubility in biologically relevant media such as aqueous media for adequate release/dissolution of the (17-β)-Hydroxy-4-Androsten-3-one ester or in lipophilic additives such as fatty acids or fatty acid glycerides for adequate lipid/membrane/chylomicron partitioning.

Steroids including steroid esters, testosterone and testosterone esters are known to exhibit different solid state forms that have different properties including dissolution, bioavailability and absorption (See e.g., Ballard BE, Biles J, *Steroids*, 1964; 4: 273; Bouche R, Draguet-Brughmans M, *J Pharm Belg*, 1977; 32: 347; Carless et al. *Journal of*

*Pharmacy and Pharmacology* Volume 20, Issue 8, pages 630-638, August 1968; Borka & Haleblian (1990) *Acta Pharm. Jugosl.* 40:71-94).

There is a need for stable and bioavailable solid state forms of esters (17-β)-Hydroxy-4-Androsten-3-one such as (17-β)-3-Oxoandrost-4-en-17-yl tridecanoate (or the corresponding tetradecanoate) that would be suitable for use in treatment of subjects in need of (17-β)-Hydroxy-4-Androsten-3-one.

SUMMARY OF THE INVENTION

Solid state forms of (17-β)-Hydroxy-4-Androsten-3-one esters are provided herein. In particular, new solid state forms of medium and long chain alkyl esters of (17-β)-Hydroxy-4-Androsten-3-one are provided. In specific aspects, the ester of (17-3)-Hydroxy-4-Androsten-3-one is solid state (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate.

We have found that not all solid state forms of the tridecanoate ester derivative of ((17-1)-Hydroxy-4-Androsten-3-one are alike and suitable for treatment of mammals in need of (17-β)-Hydroxy-4-Androsten-3-one. We have found that specific solid state tridecanoate ester derivatives of (17-β)-Hydroxy-4-Androsten-3-one wherein at least 0.001% (e.g., at least 0.01, 0.1 1.0 or 10%) of the solid state active tridecanoate ester derivative of (17-β)-Hydroxy-4-Androsten-3-one dissolves in 1000 mL 8% Triton X100 containing aqueous solution in 30 minutes in a USP Type 2 apparatus at 37° C. at 100 r.p.m. are more suitable for administering to a human (e.g., treating or preventing a disease, condition or disorder).

Additionally, we have now found that the apparent solubility of only specific solid state forms of ((17-β)-Hydroxy-4-Androsten-3-one esters in lipophilic additives, such as a fatty acid (e.g. oleic acid) or fatty acid glycerides (mono, di or triglyceride or mixtures thereof), of at least about 5 mg/g or at least about 100 mg/g facilitates adequate partitioning into the formulation or physiologically generated chylomicrons, thus enhancing their effective oral bioavailability. Thus, adequate solubility of specific solid state forms (17-β)-Hydroxy-4-Androsten-3-one esters in lipids or lipophilic additives (e.g., at least 5 mg/g or at least 100 mg/g) is desired for effective oral absorption. Without wishing to be bound by theory it is believed that excessive lipid solubility in lipophilic additives such as medium/long chain fatty acids and food glycerides (or chemical modified food glycerides), such as greater than 300 mg/g, may not cause sufficient partitioning of the drug substance out of chylomicrons, and thus not be adequately bioavailable. Therefore, in one embodiment, solid state forms of an ester of (17-β)-Hydroxy-4-Androsten-3-one such as the tridecanoate ester, which has an apparent solubility in a lipid additive of at least about 5 mg/g to at least about 100 mg/g are provided which is useful for treating mammals (e.g., humans) in need of (17-β)-Hydroxy-4-Androsten-3-one treatment.

Moreover, it has been found that therapeutic utility of solid state forms of the ester derivatives of this invention are dissolution/release dependent in aqueous medium; therefore, in one embodiment the solid state tridecanoate ester derivative of (17-β)-Hydroxy-4-Androsten-3-one is provided, wherein at least 20% more (17-β)-3-Oxoandrost-4-en-17-yl tridecanoate is released using a USP type 2 apparatus in about 1000 mL 8% Triton X100 solution in water, at 30 minutes than an equivalent amount of solid state active tridecanoate ester derivative of (17-β)-Hydroxy-4-Androsten-3-one that dissolves less than 0.001% in 8% Triton X100 at 30 minutes.

It was found that compositions of select solid forms described herein are adequately bioavailable. In one embodiment, a composition for administration to a human subject in need of ((17-β)-Hydroxy-4-Androsten-3-one therapy is provided, the composition comprising or made from: a) a solid state of a (17-β)-Hydroxy-4-Androsten-3-one ester and b) a pharmaceutically acceptable carrier, wherein upon oral administration of the solid state of an ester of (17-β)-Hydroxy-4-Androsten-3-one to the human subject, at least about 0.1% 0.5%, 1%, 2%, or 3% of the (17-β)-Hydroxy-4-Androsten-3-one equivalent dose is bioavailable (17-β))-Hydroxy-4-Androsten-3-one to the human subject.

Thus, in one embodiment, a solid state EAPI which is (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate is provided. The solid state EAPI is crystalline, non-crystalline, or a mixture thereof. For example, the solid state EAPI is crystalline (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate. In another example, the solid state EAPI is non-crystalline (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate. In a specific aspect, the solid state EAPI is amorphous (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate. The solid state EAPI is useful for administration to a human e.g., the solid state EAPI is (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate useful for administration to humans.

Solid state EAPI is provided herein which is crystalline (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate. The crystalline solid state EAPI can be a particular crystal form, a solvate of a crystal form, a polymorph, a pseudopolymorph, a pharmaceutically acceptable solvate, or a hydrate of crystalline (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate. In a specific aspect, the crystalline solid state EAPI is a crystal form substantially free of other crystal forms of solid state EAPI. In another specific aspect, the crystalline EAPI is substantially free of amorphous solid state EAPI.

In a related aspect, amorphous solid state EAPI is provided which is substantially free of crystalline EAPI.

Solid state EAPI is provided herein having a particular size characteristic. For example provided herein is solid state EAPI which is not-milled or is milled, micronized or nanosized. Thus, solid state EAPI is provided which is (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate where the EAPI is not-milled or is milled, micronized or nanosized. In specific aspects, the solid state EAPI is (17-β)-3-Oxoandrost-4-en-17-yl undecanoate, (17-

β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate wherein the particle size of the EAPI is less than 200 nm ("nanometer"), from 200 to 500 nm, from 500 to 1000 nm, from 1 to 50 μm ("micrometer"), from 50 to 250 μm, from 250 to 500 μm, from 500 to 1000 μm, or greater than 1000 μm. In another aspect, the solid state EAPI is (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate having a $d_{50}$ of greater than 1000 μm, from 355 to 1000 μm, from 180 to 355 μm, from 125 to 180 μm, 90 to 125 μm 1 to 90 μm, or less than 1 μm. In another related aspect, the solid state EAPI is (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate having a $D_{10}$, $D_{50}$, or $D_{90}$ that is less than 200 nm, from 200 to 500 nm, from 500 to 1000 nm, from 1 to 50 μm, from 50 to 250 μm, from 250 to 500 μm, from 500 to 1000 μm, or greater than 1000 μm. In one particular aspect, the EAPI having a particular size or size characteristics is crystalline EAPI. In another particular aspect, the EAPI having a particular size or size characteristics is a crystal form of the EAPI substantially free of other crystal forms of the EAPI. In yet another, the EAPI having a particular size or size characteristics is amorphous EAPI. In yet another, the EAPI having a particular size or size characteristics is amorphous EAPI substantially free of crystalline EAPI.

Pharmaceutical compositions are provided herein having or prepared from a solid state EAPI as described in the paragraphs above. For example, the pharmaceutical composition is prepared from or has a solid state EAPI chosen from (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, and (17-β)-3-Oxoandrost-4-en-17-yl tetradecanoate and one or more pharmaceutically acceptable excipients or carriers. The pharmaceutical composition described herein can comprise or be prepared from crystalline solid state EAPI, amorphous solid state EAPI, or a combination thereof. The pharmaceutical composition comprises or is prepared from a particular crystal form, a solvate of a crystal form, a polymorph, a pseudopolymorph, a pharmaceutically acceptable solvate, or a hydrate of crystalline (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate. Alternatively, the pharmaceutical composition is prepared from or comprises amorphous solid state (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate. In some aspects, the pharmaceutical composition comprises or is prepared from solid state EAPI which is (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate where the EAPI is not-milled or is milled, micronized or nanosized. Is specific aspects, the pharmaceutical composition comprises or is prepared from solid state EAPI is which is (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate wherein the particle size of the EAPI is less than 200 nm, from 200 to 500 nm, from 500 to 1000 nm, from 1 to 50 μm, from 50 μm to 250 μm, from 250 μm to 500 μm, from 500 μm to 1000 μm, or greater than 1000 μm. In another aspect, the pharmaceutical composition comprises or is prepared from solid state EAPI is which is (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate having a $d_{50}$ of greater than 1000 μm, from 355 to 1000 μm, from 180 to 355 μm, from 125 to 180 μm, from 90 to 125 μm, from 1 to 90 μm, or less than 1 μm. In another related aspect, the pharmaceutical composition comprises or is prepared from solid state EAPI is which is (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate having a $D_{10}$, $D_{50}$, or $D_{90}$ that is less than 200 nm, from 200 to 500 nm, from 500 to 1000 nm, from 1 to 50 μm, from 50 to 250 μm, from 250 to 500 μm, from 500 to 1000 μm, or greater than 1000 μm. In some specific aspects, the pharmaceutical composition of this paragraph is formulated for topical, enteral or parenteral administration. In some aspects, the pharmaceutical composition of this paragraph is formulated for buccal, sublingual, or sublabial administration. In some specific aspects, the pharmaceutical composition of this paragraph is formulated for nasal, rectal or vaginal administration. In some specific aspects, the pharmaceutical composition of this paragraph is formulated for intravenous, subcutaneous, intramuscular, intradermal, intraspinal, intrathecal, or intraarterial administration. In some specific aspects, the pharmaceutical composition of this paragraph is formulated as a liquid, solution, suspension, dispersion, solid, semi-solid, a gel, a lotion, paste, foam, spray, suspension, dispersion, syrup, or ointment. In some specific aspects, the pharmaceutical composition of this paragraph is formulated as a tincture, patch, injectable, or oral dosage form. In some aspects, the pharmaceutical composition of this paragraph comprises solubilized or partially solubilized (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate solid state EAPI. In one aspect, the pharmaceutical composition or unit dosage forms is suitable for oral administration (e.g., capsule or tablet).

Provided herein are unit dosage form comprising or prepared from the solid state EAPI or pharmaceutically compositions as described in the paragraphs above.

Additionally, described herein are methods of making solid state EAPI and methods of using solid state EAPI.

BRIEF DESCRIPTION OF THE DRAWINGS

Features and advantages of invention embodiments will be apparent from the detailed description which follows, taken in conjunction with the accompanying drawings, which together illustrate, by way of example, features of the disclosure; and wherein.

DETAILED DESCRIPTION OF THE INVENTION

Figure 1A:
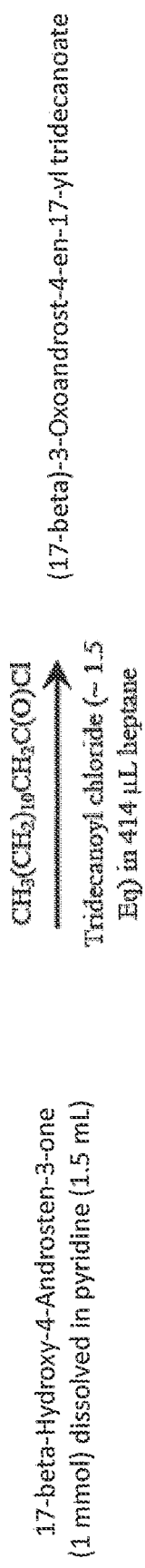
FIG. 1A shows a non-limiting example of a synthetic scheme for making solid state form (17-β)-3-Oxoandrost-4-en-17-yl tridecanoate disclosed in this invention.

The specific solid state forms of (17-β)-Hydroxy-4-Androsten-3-one esters disclosed herein have one or more advantageous properties compared to other forms such as chemical or polymorphic purity, increased crystallinity, flowability, solubility, dissolution rate, bioavailability, morphology or crystal habit, specific surface and pycnometric density, bulk/tap density, stability (e.g., such as chemical stability as well as thermal and mechanical stability with respect to polymorphic conversion), stability towards hydration and/or storage stability, a lower degree of hygroscopicity, low content of residual solvents and advantageous processing and handling characteristics such as compressibility and bulk density. Specific solid state forms of (17-β)-Hydroxy-4-Androsten-3-one esters are provided herein. New solid state forms of medium and long chain alkyl esters of (17-β)-Hydroxy-4-Androsten-3-one are provided, particularly (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate.

It should be noted that, the singular forms "a," "an," and, "the" include plural referents unless the context clearly dictates otherwise. Thus, for example, reference to "an excipient" includes reference to one or more of such excipients, and reference to "a carrier" includes reference to one or more of such carriers.

The term "API" refers to active pharmaceutical ingredient or drug and means (17-β)-Hydroxy-4-Androsten-3-one (also known as testosterone) which is considered the biologically active agent for the purpose of this disclosure. It is noted that (17-β)-Hydroxy-4-Androsten-3-one can be converted in vivo to (17-β)-hydroxy-5α-androstan-3-one (directly or via the corresponding ester) which is also biological activity as well as other metabolites. The term "EAPI" means an ester of (17-β)-Hydroxy-4-Androsten-3-one, a prodrug of the biologically active agent. It is understood that the EAPI can also have biological activity without cleavage of the ester, but for the purpose of this invention the API is considered the pharmacological agent.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

In this specification, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in the specification, like "comprising" or "including," it is understood that direct support should be afforded also to "consisting essentially of" language as well as "consisting of" language as if stated explicitly and vice versa.

The terms "serum testosterone" or "serum (17-β)-Hydroxy-4-Androsten-3-one levels," "serum T levels," "serum testosterone concentration," "plasma testosterone concentration," "testosterone concentration in the blood," and "serum testosterone concentration," are used interchangeably and refer to the "total" testosterone concentration which is the sum of the bioavailable testosterone including free and bound testosterone concentrations. Unless otherwise specified, these values are "observed" testosterone concentrations without adjusting or correcting for the base-line serum testosterone levels in the subject(s). As with any bio-analytical measure, for increased consistency, the method employed to measure initial serum testosterone levels should be consistent with the method used to monitor and re-measure serum testosterone levels during clinical testing and testosterone therapy for a subject. Unless otherwise stated, "testosterone concentration" refers to serum total testosterone concentration.

Average serum testosterone concentrations can be determined using methods and practices known in the art. For example, the average baseline plasma testosterone concentration of a human male is the arithmetic mean of the total plasma testosterone concentration determined on at least two consecutive time points that are reasonably spaced from each other, for example from about 1 hour to about 168 hours apart. In a particular case, the plasma testosterone concentration can be determined on at least two consecutive times that are about 12 hours to about 48 hours apart. In another particular method, the plasma testosterone concentration of the human male can be determined at a time between about 5 o'clock and about 11 o'clock in the morning. Further, the plasma testosterone concentration can be the determined by standard analytical procedures and methods available in the art, such as for example, automated or manual immunoassay methods, liquid chromatography or liquid chromatography-tandem mass spectrometry (LC-MSMS) etc.

As used herein, the term "$AUC_{t1-t2}$" is the area under the curve of a plasma-versus-time graph determined for the analyte from the time "t1 to time t2". Wherein t1 and t2 are times (in hours) post dosing. For Example, t1 could be 1 hour and t2 could be 2 hours.

As used herein, the term "$C_{avg}$," "Cave," or "C-average" are used interchangeably, and is determined as the $AUC_{t1-t2}$ mean AUC divided by the time period (|t1-t2|). For example, $C_{avg\ t0-t8}$ is the average plasma concentration over a period of 8 hours from t1=0 to t2=8 hours) post-dosing determined by dividing the $AUC_{t0-t8}$ value by 8. Similarly, $C_{avg\ t0-t12}$ is the average plasma concentration over a period of 12 hours post-dosing determined by dividing the $AUC_{t0-t12}$ value by 12 (t1=0-t2=12). Similarly, $C_{avg\ t12-t24}$ is the average plasma concentration over a period of 12 hours post-dosing determined by dividing the $AUC_{t12-t24}$ value by 12 (t1=12-t2=24); $C_{avg-t24}$ is the average plasma concentration over a period of 24 hours post-dosing determined by dividing the $AUC_{t0-t24}$ value by 24 (t1=0-t2=24), and soon. Unless otherwise stated, all $C_{avg}$ values are considered to be $C_{avg-t24}$ and unless otherwise stated, all the time values are expressed in hours (h). For example, the term $C_{avg\ t0-t24}$ denotes $C_{avg}$ from time zero (0) to 24 hours post dosing.

As used herein, "$C_t$" refers to the serum concentration of testosterone at time "t" prior to or after administration of the dosage of the current invention. The time "t" is generally in hours, unless otherwise specified. For example, a $C_t$ of "$C_{(-2\ to\ 0)}$" refers to serum testosterone concentration measured in sample collected between the time of about 2 hours before and just immediately prior to dosage administration to the subject tested. Similarly, $C_t$ of "$C_{(2\ to\ 4)}$" refers to serum testosterone concentration measured in sample collected between the time of about 2 hours and 4 hours after administration of a dosage to the subject tested.

As used herein, the term (17-β)-Hydroxy-4-Androsten-3-one refers to a chemical having an IUPAC name of (8R,9S,10R,13S,14S,17S)-17-Hydroxy-10,13-dimethyl-1,2,6,7,8,9,11,12,14,15,16,17-dodecahydrocyclopenta[a]phenanthren-3-one and a CAS number of 58-22-0. (17-β)-Hydroxy-4-Androsten-3-one esters generically refers to compounds having the (17-β)-Hydroxy-4-Androsten-3-one structure but the hydroxyl group is esterified with e.g., an alkanoic acid. For example, (8R,9S,10R,13S,14S,17S)-10,13-dimethyl-3-oxo-1,2,6,7,8,9,11,12,14,15,16,17-dodecahydrocyclopenta[a]phenanthren-17-yl undecanoate is the IUPAC name for (17-β)-Hydroxy-4-Androsten-3-one esterified with a straight chain saturated 11 carbon long alkanoic acid called undecanoic acid. Undecanoic acid is the IUPAC name for the alkanoic acid having CAS number 112-37-8. In a more specific aspect, (17-β)-Hydroxy-4-Androsten-3-one esters refers to those (17-β)-Hydroxy-4-Androsten-3-one esters specifically disclosed herein. In one specific aspect, refers to the tridecanoate (17-β)-Hydroxy-4-Androsten-3-one ester (referred to herein as (17-R)-3-Oxoandrost-4-en-17-yl tridecanoate or the tridecanoic ester of (17-β)-Hydroxy-4-Androsten-3-one and the such (CAS No. 488836-58-4)). Tridecanoic acid has an IUPAC name of Tridecanoic acid (CAS number 638-53-9) and is a 13 carbon straight chain saturated alkanoic acid. (17-β)-Hydroxy-4-Androsten-3-one has the following structure:

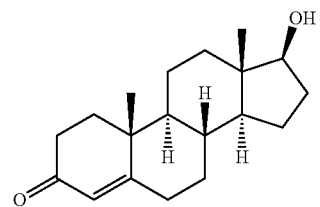

Solid state EAPI, e.g., solid state (17-β)-Hydroxy-4-Androsten-3-one esters described herein, can exist in different crystalline forms as well as in non-crystalline forms. A non-crystalline solid EAPI is referred to herein as an "amorphous form," which is a disordered arrangement of EAPI molecules. Different crystalline forms of the EAPI, e.g., of a specific (17-β)-Hydroxy-4-Androsten-3-one ester, arise from different packing of the EAPI molecules in the solid state, resulting in different crystal symmetries and/or unit cell parameters. Crystalline forms are identified or characterized by any suitable methods e.g., x-ray diffraction (see, e.g., *Remington's Pharmaceutical Sciences*, 18th ed., Mack Publishing, Easton Pa., p 173 (1990); *The United States Pharmacopeia*, 23rd ed., pp. 1843-1844 (1995)). Such different crystalline forms are referred to herein as "polymorphic forms" or "non-solvated forms," which means that they are essentially free of residual solvents e.g., organic solvents. If the substances incorporate stoichiometric or non-stoichiometric amounts of water ("hydrate" as used herein), or any other solvent ("solvate" as used herein), in the crystal structure, these are referred to herein as a "pseudopolymorphic form."

The term "amorphous form" as used herein in connection with solid state EAPI refers to an EAPI that is a non-crystalline solid (i.e., not in a crystalline form), which is a disordered arrangements of EAPI molecules. Typically, solid state amorphous EAPI has no long-range periodic atomic structure as determined by X-ray powder diffraction (XRPD). The XRPD pattern of amorphous EAPI appears as a halo with no distinctive peaks. Amorphous material for some compounds can be obtained by a number of methods known in the art, including, but not limited to, heating, melt cooling, rapid melt cooling, solvent evaporation, rapid solvent evaporation, desolvation, sublimation, grinding, cryo-grinding or freeze-drying.

The term "crystal" as used herein refers to a solid structure, typically formed by a solidification of an EAPI, that generally has a regular atomic structure (characteristic shapes and cleavage planes formed by the arrangement of molecules in a pattern referred to as a "lattice").

The term "seeding" as used herein refers to starting or promoting a crystallization event using a small amount of material.

As used herein, the term "Triton X100" or Triton "X-100" is a non-ionic detergent and refers to a composition as known as polyethylene glycol p-(1,1,3,3-tetramethylbutyl)-phenyl ether, octyl phenol ethoxylate, polyoxyethylene octyl phenyl ether, 4-octylphenol polyethoxylate, Mono 30, TX-100, t-octylphenoxypolyethoxyethanol, or Octoxynol-9 and associated with CAS NO. 9002-93-1.

A "pharmaceutical composition" as used herein refers to a composition comprising or prepared from a solid state form of a (17-β)-hydroxy-4-Androsten-3-one ester and a pharmaceutically acceptable carrier or excipient. A "unit dosage form" as used herein refers to a medicament prepared from or comprising a pharmaceutical composition and includes tablets, capsules, caplets, gelcaps, ampoules, suspensions, solutions, gels, dispersions and other dosage units typically associated with parenteral, enteral, topical or other forms of administration of an EAPI to a subject in need thereof.

A "pharmaceutically acceptable carrier" or "pharmaceutically acceptable excipient" or similar term refers to one or multiple components or ingredients that is acceptable (1) as being compatible with the other ingredients in compositions or formulations comprising an EAPI and (2) are not deleterious or overly deleterious to a subject to whom the composition or formulation is to be administered. Excipients include without limitation, benzyl benzoate, cottonseed oil, N,N-dimethylacetamide, an alcohol such as methanol, ethanol, glycerol, peanut oil, a polyethylene glycol ("PEG") (low molecular weight (200-), vitamin E, castor oil, poppy seed oil, peppermint oil, borage oil, propylene glycol, medium molecular and high molecular weight), safflower oil, sesame oil, soybean oil or other vegetable oil. Excipients can include dissolution aids typically used for EAPIs that are sparingly soluble or insoluble in water such as a cyclodextrin or a cyclodextrin derivative such as β-cyclodextrin, 2-hydroxypropyl-β-cyclodextrin and CAPTISOL™ (sulfobutyl ether-β-cyclodextrin) and a PEG or PEG derivative such as CREMOPHOR™ (a polyethoxylated castor oil). Any solid excipient may be a fine powder or granulated. Excipient, as used herein may optionally exclude one or more excipients, e.g., chloroform, dioxane, vegetable oil, DMSO, other another excipient (e.g., those listed herein or elsewhere) or any combination of these. Excipients include one or more components typically used in the pharmaceutical formulation arts, e.g., in some instances one, two, or more of fillers, binders, disintegrants, dispersants, preservatives, glidants, surfactants, stabilizers (e.g., antioxidants like ester of ascorbic acid (e.g., ascorbyl palmitate)) and lubricants. Exemplary excipients include povidone, crospovidone, corn starch, carboxymethyl cellulose, hydroxypropyl methylcellulose, microcrystalline cellulose, gum arabic, polysorbate 80, butylparaben, propylparaben, methylparaben, BHA, EDTA, sodium lauryl sulfate, sodium chloride, potassium chloride, titanium dioxide, magnesium stearate, castor oil, olive oil, vegetable oil, fatty acid (e.g., C8 to C22 straight or branched chain, saturated or unsaturated fatty acids like oleic acid, stearic acid, or myristic acid), mono-, di-, or tri-glycerides or mixtures thereof (e.g., of C8 to C22 straight or branched chain, saturated or unsaturated fatty acids like oleic acid, stearic acid, myristic acid, linoleic acid, palmitic acid, or a combination thereof) buffering agents such as sodium hydroxide, monobasic sodium phosphate, dibasic sodium phosphate, potassium hydroxide, monobasic potassium phosphate, dibasic potassium phosphate, tribasic potassium phosphate, potassium carbonate, potassium bicarbonate, ammonium hydroxide, ammonium chloride, saccharides such as mannitol, glucose, fructose, sucrose or lactose any of which may be compressible or any of which may be spray dried.

Carriers (e.g., pharmaceutically acceptable excipients or additives) and methods of preparing oral pharmaceutical compositions comprising (17-β)-3-Oxoandrost-4-en-17-yl tridecanoate (or any other of the (17-β)-3-Oxoandrost-4-en-3-one esters) are available to the skilled artisan in view of this application which typical involve a specific solid state form of the EAPI.

Carriers and methods of manufacture of non-oral pharmaceutical compositions comprising (17-β)-3-Oxoandrost-4-en-17-yl tridecanoate (or any other of the (17-β)-3-Oxoandrost-4-en-3-one esters) are available to the skilled artisan in view of this application which typically involve a specific solid state form of the EAPI. In one embodiment, a pharmaceutical composition and unit dosage form for injectable administration (e.g., parenteral administration, intramuscular injection (e.g., depot), subcutaneously) is provided. In one example, the pharmaceutical composition comprises or is prepared from (17-β)-3-Oxoandrost-4-en-17-yl tridecanoate and a vehicle comprising a pharmaceutically acceptable oil. In one aspect, the vehicle further comprises a co-solvent. In one aspect, the pharmaceutically acceptable oil is castor oil. In one aspect, the co-solvent is benzyl benzoate. Other types of co-solvents may be applicable for use in combination with the vehicle (e.g., castor oil), such as ethanol or benzyl alcohol or others. In one aspect, the co-solvents are those which are capable of dissolving the solid state (17-β)-3-Oxoandrost-4-en-17-yl tridecanoate and is miscible with castor oil. In some aspects, the co-solvent(s) is suitable for dissolving about 100-500 mg, such as 250 mg of solid state (17-β)-3-Oxoandrost-4-en-17-yl tridecanoate in 1 mL of the co-solvent within 50 minutes at 40° C. or within 20 minutes at 60° C. In some aspects, the compositions have the co-solvent present in the vehicle at concentrations ranging from 10 to 90 volume % ("v %"). In some aspects, the concentration of the co-solvent in the vehicle ranges between 15 to 90 v %, between 20 to 85 v %, between 45 to 85 v % or 55 to 85 v %. Thus, in some aspects, the vehicle comprises castor oil in a volume concentration ranging between 20 to 85 v %. The concentration of castor oil in the vehicle ranges between 25 to 60 v %, such as between 25 to 55 v %. In a preferred embodiment, the concentration of castor oil in the vehicle ranges between 25 to 50 v %, such as between 25 to 45 v % or 25 to 40 v %. Other formulations are also contemplated including those having (or prepared from) different amounts of a particular form or forms of solid state EAPI, different vehicles, different co-solvents, or a combination thereof. In some aspects, the parenteral formulation is injected as a depot (e.g., intramuscular). In some aspects, the formulation is injected subcutaneously. The amount injected depends on a number of factors, but preferably is in the range of 0.100 ml, to 5 mL and provides sufficient levels of (17-β)-3-Oxoandrost-4-en-17-yl tridecanoate or testosterone to the individual to maintain a hypogonadal male in a eugonadal range for 1 day or more, or more than 2, 3, 4, 5, 6, 7, 8, 9, 10, 15, 20, 30, 40, 50, 60, 70, 80, 90, 100, 120, 140, 160, or 180 or more days per injection.

Reference will now be made in detail to specific embodiments of the invention. While the invention will be described in conjunction with such embodiments, it will be understood that it is not intended to limit the invention to those embodiments. To the contrary, it is intended to cover alternatives, variants, modifications, and equivalents as may be included within the spirit and scope of the invention as defined by the appended claims.

(17-β)-3-Oxoandrost-4-en-17-yl tridecanoate can be prepared by a number of synthetic routes (as well as other corresponding esters in an analogous fashion). In one aspect, (17-β)-3-Oxoandrost-4-en-17-yl tridecanoate is prepared for the corresponding alcohol via an esterification reaction with an activated fatty acid and (17-β)-Hydroxy-4-Androsten-3-one (of n-tridecanoic acid, IUPAC name tridecanoic acid, CAS number 638-53-9) e.g., an acid chloride or anhydride, in a suitable solvent under suitable conditions to produce the product. In one aspect, the (17-β)-Hydroxy-4-Androsten-3-one is prepared from a phytosterol or cholesterol or any other suitable starting material. The product is worked up via any number of techniques. For example, the product is dissolved in a solvent (e.g., organic solvent such as heptanes or any other solvent); washed successively with e.g., cold water (2×), 0.05 N NaOH, saturated NaHCO$_3$ (2×), water, brine, then dried (e.g., over anhydrous Na$_2$SO$_4$ (~50 g), followed by concentration to dryness. Without wishing to be bound by theory, the inventors have unexpectedly found that crystallization or recrystallization of (17-β)-3-Oxoandrost-4-en-17-yl tridecanoate provides solid state EAPI with one or more advantageous properties as described herein.

Thus, according to one embodiment, recrystallized or crystallized solid state EAPI (17-β)-3-Oxoandrost-4-en-17-yl tridecanoate is provided. According to this embodiment (17-β)-3-Oxoandrost-4-en-17-yl tridecanoate is dissolved in a solvent and allowed to crystallize or recrystallize or after a first crystallization is transferred to another solvent and allowed to crystallize or recrystallize. The crystalline mass can be isolated (e.g., filtered by suction), optionally washed (e.g., with water), optionally dried (e.g., over phosphorous pentoxide) and optionally re-crystallized from another solvent e.g., oleic acid, hexane, heptanes, etc. In one aspect, the solvent (for crystallization or recrystallization) is an alcohol (e.g., ethanol, methanol, or propanol), fatty acid (e.g., oleic acid, linoleic acid, or linoleic acid), alkane (e.g., hexane, heptane, pentane, or halogenated alkane), oil (e.g., vegetable oil, castor oil, or hydrogenated oil), or any other suitable solvent (e.g., pyridine, benzene, or toluene). In this context, a solvent refers to a liquid in which (17-β)-3-Oxoandrost-4-en-17-yl tridecanoate is soluble and/or can crystallize from.

Crystalline forms of a substance can be obtained by a number of techniques, as is known in the art. Exemplary techniques for obtaining, producing, or manufacturing crystalline forms of (17-β)-Hydroxy-4-Androsten-3-one esters include e.g., melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding and solvent-drop grinding.

Typically, crystalline forms of specific (17-β)-Hydroxy-4-Androsten-3-one esters can be distinguished from each other by one or more physical or analytical properties such as rate of dissolution, infrared or Raman spectroscopy, x-ray diffraction techniques such as single crystal and powder diffraction techniques, solid state-NMR (SS-NMR), thermal techniques such as melting point, differential thermal analysis (DTA), differential scanning calorimetry (DSC), thermal gravimetric analysis (TGA) and other methods as disclosed elsewhere in the specification or available to the skilled artisan. Other methods to characterize or distinguish a pseudopolymorph from another isostructural polymorph, pseudopolymorph, desolvate or anhydrate include elemental analysis, Karl-Fisher titration, dynamic vapor sorption analysis, thermogravimetric-infrared spectroscopic analysis (TG-IR), residual solvent gas chromatography, 1H-NMR etc.

Thus, in one embodiment, a solid state EAPI which is (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate is provided wherein the solid state EAPI has one or more advantageous properties compared to other forms such as chemical, crystalline, or polymorphic purity, increased crystallinity, flowability, solubility, dissolution rate, bioavailability, morphology or crystal habit, specific surface and pycnometric density, bulk/tap density, stability (e.g., such as chemical stability as well as thermal and mechanical stability with respect to polymorphic conversion), stability towards hydration and/or storage stability, a lower degree of hygroscopicity, low content of residual solvent(s) and advantageous processing and handling characteristics such as compressibility and bulk density. The solid state EAPI is crystalline, non-crystalline, or a mixture thereof. For example, the solid state EAPI is crystalline (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate. In another example, the solid state EAPI is non-crystalline (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate. In a specific aspect, the solid state EAPI is amorphous (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate. The solid state EAPI is useful for administration to a human e.g., the solid state EAPI is (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate useful for administration to humans. In specific aspects of this embodiment, the solid state EAPI has unexpectedly improved dissolution, solubility, bioavailability, bioactivity, fluctuation index, processing, manufacturing, storage, taste, color, aggregates or granules.

In one embodiment, solid state EAPI is provided comprising solid (17-β)-3-Oxoandrost-4-en-17-yl tridecanoate. In one aspect of this embodiment, the solid state EAPI is crystalline or non-crystalline (17-β)-3-Oxoandrost-4-en-17-yl tridecanoate, or a mixture thereof. In a specific aspect, the solid state EAPI is amorphous (17-β)-3-Oxoandrost-4-en-17-yl tridecanoate. The solid state EAPI is particularly suitable for administration to a human. In one aspect, the solid state EAPI is a specific crystalline (17-β)-3-Oxoandrost-4-en-17-yl tridecanoate form (e.g., substantially similar to that characterized in the Examples and figures by XRD and DSC). In a specific aspect, the solid state EAPI is crystalline (17-β)-3-Oxoandrost-4-en-17-yl tridecanoate having 50%, 40%, 30%, 20%, 10%, 5%, 2%, or 1% or less by total weight of EAPI of amorphous (17-β)-3-Oxoandrost-4-en-17-yl tridecanoate. In another aspect, the solid state EAPI is a solvate or a pseudopolymorph of (17-β)-3-Oxoandrost-4-en-17-yl tridecanoate. In another aspect, the solid state EAPI is a polymorph of (17-β)-3-Oxoandrost-4-en-17-yl tridecanoate. In another aspect, the solid state EAPI is a hydrate of (17-β)-3-Oxoandrost-4-en-17-yl tridecanoate. In yet another aspect, the solid state EAPI is crystalline (17-β)-3-Oxoandrost-4-en-17-yl tridecanoate form having 50%, 40%, 30%, 20%, 1%, 50%, 2%, or 1% or less by total weight of EAPI of other crystalline forms of (17-β)-3-Oxoandrost-4-en-17-yl tridecanoate. In one aspect, the solid state EAPI is crystalline (17-β)-3-Oxoandrost-4-en-17-yl tridecanoate having a melting point in the range of 30 to 150° C., 40 to 120° C., 50 to 100° C., 55 to 90° C., 60 to 85° C., 60 to 80° C., or 66 to 77° C. as determined by differential scanning calorimetry. In one aspect, the solid state EAPI is crystalline (17-β)-3-Oxoandrost-4-en-17-yl tridecanoate having a melting point in the range of 60 to 85° C., 62 to 83° C., 64 to 81° C., 64 to 79° C., 66 to 77° C., 68 to 75° C., or 69 to 73° C. as determined by differential scanning calorimetry. In one aspect, the solid state EAPI has a melting point as determined by differential scanning calorimetry characteristic of a single crystal form or non-amorphous (17-β)-3-Oxoandrost-4-en-17-yl tridecanoate. In one aspect, the solid state EAPI is crystalline (17-β)-3-Oxoandrost-4-en-17-yl tridecanoate having 1, 2, 3, 4, 5, 6 or more peaks as determined by XRD corresponding to those in FIG. 6 (at a given count threshold of above 250, 500, 750, 1000, or 1250). In again yet another aspect, the solid state EAPI is amorphous (17-β)-3-Oxoandrost-4-en-17-yl tridecanoate having 50%, 40%, 30%, 20%, 10%, 5%, 2%, or 1% or less by total weight of crystalline (17-β)-3-Oxoandrost-4-en-17-yl tridecanoate. In one aspect, the solid state EAPI is crystalline (17-β)-3-Oxoandrost-4-en-17-yl tridecanoate which is not milled or is milled, micronized, or nanosized. In one aspect, the solid state EAPI is (17-β)-3-Oxoandrost-4-en-17-yl tridecanoate having a $d_{50}$ of greater than 1000 μm, from 355 to 1000 μm, from 180 to 355 μm, from 125 to 180 μm, from 90 to 125 μm, from 1 to 90 μm, or less than 1 μm. In one aspect, the solid state EAPI is (17-β)-3-Oxoandrost-4-en-17-yl tridecanoate having a particle size of less than 200 nm, from 200 to 500 nm, from 500 to 1000 nm, from 1 to 50 μm, from 50 μm to 250 μm, from 250 μm to 500 μm, from 500 μm to 1000 μm, or greater than 1000 μm. In one aspect, the solid state EAPI is (17-β)-3-Oxoandrost-4-en-17-yl tridecanoate having a $D_{10}$, $D_{50}$, or $D_{90}$ that is less than 200 nm, from 200 to 500 nm, from 500 to 1000 nm, from 1 to 50 μm, from 50 to 250 μm, from 250 to 500 μm, from 500 to 1000 μm, or greater than 1000 μm. In one aspect, the solid state (17-β)-3-Oxoandrost-4-en-17-yl tridecanoate is a composition having greater than 1 g, 2 g, 50 g, 500 g, 1 kg, 10 kg, 50 kg, 100 kg, 200 kg, 500 kg, 1000 kg, 2000 kg, 5000 kg, or 10,000 kg solid state (17-β)-3-Oxoandrost-4-en-17-yl tridecanoate. In one aspect, the release profile of the (17-β)-3-Oxoandrost-4-en-17-yl tridecanoate does not change substantially as a function of time.

Production of Amorphous EAPI or Different Crystal Forms of Solid State EAPI

Described herein are different forms of EAPI, particularly (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate. The identification of different forms of EAPI yields new, improved properties related to the use of the EAPI.

A number of different forms, including crystalline forms of (17-β)-3-Oxoandrost-4-en-17-yl tridecanoate may exist. Crystalline (17-β)-3-Oxoandrost-4-en-17-yl tridecanoate may be produced according to the figures and as described herein or by other methods available to the ordinary skilled artisan in view of this disclosure to obtain solid state forms having desirable properties.

Amorphous (17-β)-3-Oxoandrost-4-en-17-yl tridecanoate is another solid state EAPI form. A number of techniques are available for preparing amorphous (17-β)-3-Oxoandrost-4-en-17-yl tridecanoate. For example, flash evaporation, lyophilization, quench cooling of the melt, spray drying, grinding, supercritical fluids are non-limiting techniques that can be used to make amorphous EAPI. In some aspects, the amorphous (17-β)-3-Oxoandrost-4-en-17-yl tridecanoate is metastable.

Experimental Instrumentation and Conditions for Analyzing Solid State EAPI

A variety of techniques may be used to identify or characterize solid state EAPI, particularly solid state (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate.

Fourier Transform-Raman Spectroscopy ("FT-Raman") is useful for characterizing and identify solid state forms of (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate. For example, different solid EAPI forms may be characterized using a Bruker RFS100 instrument, with Nd:YAG 1064 nm excitation, 300 mW laser power, Ge detector, using 64 scans over the range of 25-3500 $cm^{-1}$, and with 2 $cm^{-1}$ resolution. As is understood by the ordinary skilled artisan, the parameters and instrumentation for FT-Raman may be modified depending on the instrument, the solid state EAPI and goal(s) of the analysis.

Figure 6:
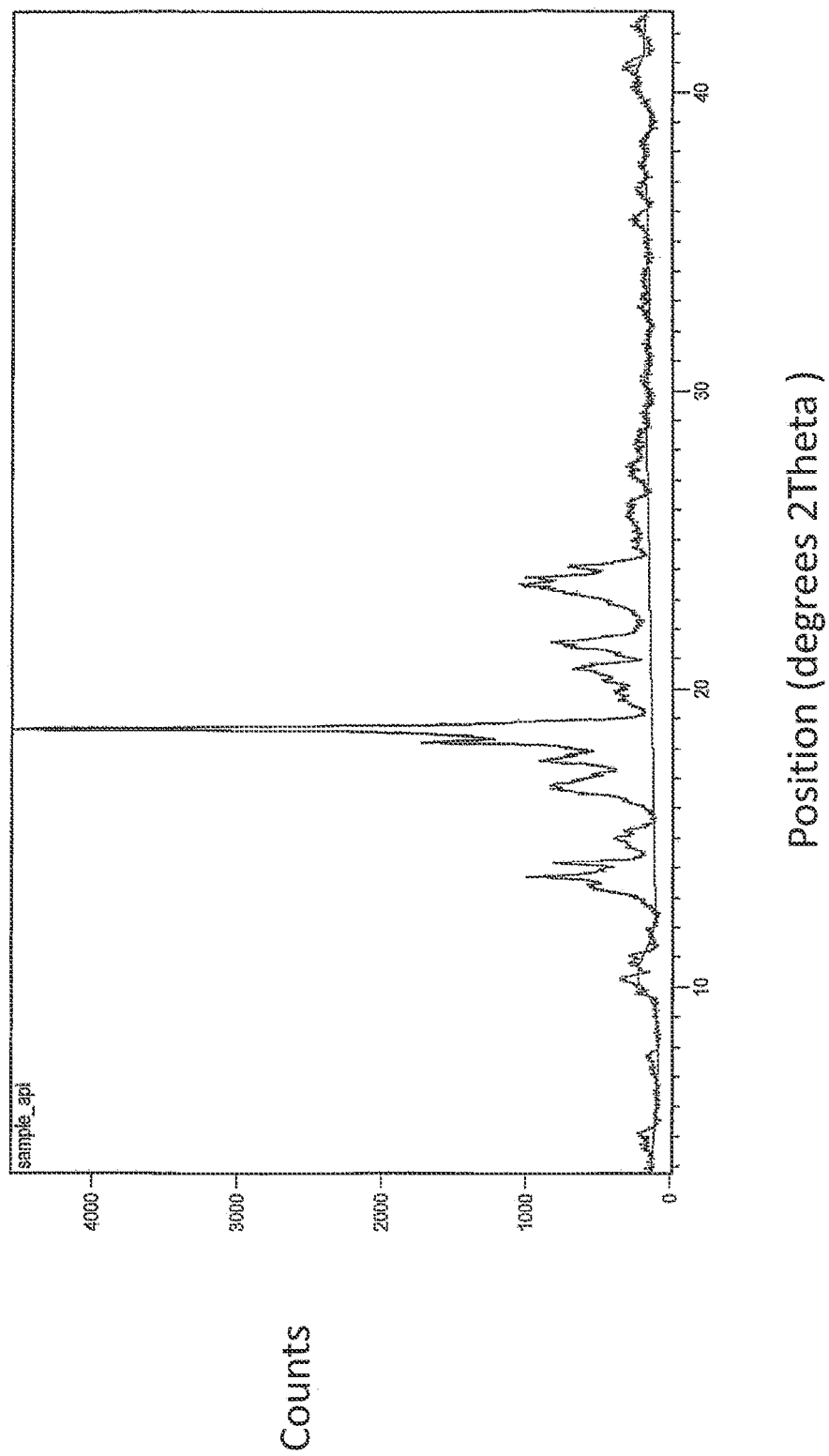
FIG. 6 shows a plot of a powder x-ray diffraction analysis of a solid state form of (17-β)-3-Oxoandrost-4-en-17-yl tridecanoate as disclosed herein.

Another useful technique for characterization is Power X-ray Diffraction ("XRD"). XRD can be performed with a Bruker $D_8$ Advance X-ray diffractometer with CuKα-radiation. The standard measuring conditions are e.g., tube power 35 kV/45 mA; step size 0.017° (2θ); step time 105±5 sec; scanning range 2°-50° (2θ); divergence slit equal to variable V12; sample rotation; a Vantec1 detector; the opening angle 3°; channel number 360±10; the y-axis shows the value intensity/number of active detector channels/sec; silicon single crystal sample holders; and the sample dimensions depth/diameter was 0.1 mm/~12 mm. As is understood by the ordinary skilled artisan, the parameters and instrumentation for powder XRD may be modified depending on the instrument, the solid state EAPI and goal(s) of the analysis. In one embodiment, the solid state (17-β)-3-Oxoandrost-4-en-17-yl tridecanoate EAPI is crystalline or substantially crystalline as indicated by XRD. An example of an XRD spectra is shown in FIG. 6 for crystalline or substantially crystalline (17-β)-3-Oxoandrost-4-en-17-yl tridecanoate. FIG. 6 shows well defined peaks corresponding to crystalline or substantially crystalline (17-β)-3-Oxoandrost-4-en-17-yl tridecanoate with little or no amorphous EAPI (as indicated by the absence of an "amorphous halo" in the spectra in the 20-40 degree 2θ range). In one aspect, the solid state EAPI described herein has 1, 2, 3, 4, 5, 6, 7, 8, 9, 10, 11, or 12 or more of the peaks that corresponds to those in FIG. 6 that have above 100, 200, 300, 400, 500, 600, 700, 800, 900, 1000 or 1200 counts.

Thermogravimetric-Fourier transform Infrared Spectroscopy ("TG-FTIR") can also be used to characterize or analyze solid state EAPI. For example, TG-FTIR can be performed with a Netzsch Thermo-Microbalance TG 209 coupled with a Bruker FT-IR Spectrometer Vector 22, using an aluminum crucible (open or with a microhole), under a nitrogen atmosphere, and e.g., at a heating rate of 10° C./min over the range of 25° C. to 350° C. As is understood by the ordinary skilled artisan, the parameters and instrumentation for TG-FITR may be modified depending on the instrument, the solid state EAPI and goal(s) of the analysis.

Characterization/Analysis of EAPI can also be performed using Differential Scanning Calorimetry ("DSC"). For example, DSC can be performed with a Perkin Elmer Differential Scanning Calorimeter, using closed gold crucibles, a heating rate of 10° C. $min^{-1}$ or 20° C. $min^{-1}$ over a range from 0° C. to 250° C. (or e.g., over a range from 5° C. to 150° C.). See e.g., Example 3. As is understood by the ordinary skilled artisan, the parameters and instrumentation for DSC may be modified depending on the instrument, the solid state EAPI and goal(s) of the analysis.

Thus, in yet another embodiment, a solid state EAPI, e.g., (17-β)-3-Oxoandrost-4-en-17-yl undecanoate, (17-β)-3-

Oxoandrost-4-en-17-yl dodecanoate, (17-β)-3-Oxoandrost-4-en-17-yl tridecanoate, or (17-β)-3-Oxoandrost-4-en-17-yl tetradecanoate, is provided which has a melting point in the range of about 20 to 150° C., as determined by DSC. In a more specific embodiment, a solid state EAPI is provided which has a melting point in the range of about 55 to 80° C., as determined by DSC. In another specific embodiment, a solid state EAPI is provided which has a melting point in the range of about 65 to 75° C., as determined by DSC. In one aspect of this embodiment, the melting point of the solid state EAPI is characteristic of a single physical form of EAPI e.g., a single crystalline form or amorphous EAPI.

In yet another embodiment, a pharmaceutical composition or unit dosage form having a solid state EAPI (e.g., (17-β)-3-Oxoandrost-4-en-17-yl undecanoate, (17-β)-3-Oxoandrost-4-en-17-yl dodecanoate, (17-β)-3-Oxoandrost-4-en-17-yl tridecanoate, or (17-β)-3-Oxoandrost-4-en-17-yl tetradecanoate) is provided where the pharmaceutical composition has a melting point in the range of about 10 to 200° C., as determined by DSC. The pharmaceutical composition of this embodiment, comprises or is prepared from solid state EAPI and one or more pharmaceutically acceptable carriers. In a more specific embodiment, a pharmaceutical composition is provided having or prepared from solid state EAPI where the solid state starting material has a melting point in the range of about 30 to 150° C., as determined by DSC. In a more specific embodiment, a pharmaceutical composition is provided having or prepared from solid state EAPI where the solid state starting material has a melting point in the range of about 60 to 85° C., 62 to 83° C., 64 to 81° C., 64 to 79° C., 66 to 77° C., 68 to 75° C., or 69 to 73° C., as determined by DSC. In a specific embodiment, a pharmaceutical composition is provided having or prepared from solid state which has a melting point of EAPI in the range of about 40 to 90° C., as determined by DSC. In one aspect of this embodiment, the melting point of the pharmaceutical composition or unit dosage form does not have a peak corresponding to the melting point peak of the EAPI from which it was prepared as determined by DSC. For example, the melting point of the starting solid state EAPI is in the range of 69-73° C. and when the melting point of the pharmaceutical composition comprising the EAPI is determined the melting point peak in the range of 69-73° C. disappears is diminished or substantially diminished.

Dynamic Vapor Sorption (DVS) analysis is another technique for characterizing and analyzing EAPI. For example, DVS can be performed with a Surface Measurement Systems DVS-1 water vapor sorption analyzer. The experiments can be run by placing the sample on a quartz holder on top of a microbalance, and allowing the sample to equilibrate at 50% relative humidity (r.h.) before starting the pre-defined humidity program. The program can proceed e.g., in the following steps: 1 hour at 50% r.h.; 50% to 0% r.h. at a rate of 5% r.h. change per hour; 5 hours at 0% r.h; 0% r.h to 96% r.h. at 5% r.h change per hour; 5 hours at 95% r.h.; 95% r.h. to 50% r.h. at a rate of 5% r.h. change per hour, and followed by one hour at 50% r.h. As is understood by the ordinary skilled artisan, the parameters and instrumentation for DVS may be modified depending on the instrument, the solid state EAPI and goal(s) of the analysis.

High performance liquid chromatography (HPLC) is also useful for analyzing or characterizing EAPI. In some of the embodiments, the purity of the amorphous form of (17-β)-3-Oxoandrost-4-en-17-yl tridecanoate as measured by high pressure liquid chromatography (HPLC) is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at a suitable wavelength e.g., about 240 nm or about 242 nm. In some embodiments, the amorphous form of (17-β)-3-Oxoandrost-4-en-17-yl tridecanoate is about 100.0% pure as measured by HPLC as area under the curve as observed at a suitable wavelength, e.g., at a wavelength of from about 200 nm to about 300 nm, e.g., about 240 nm or 242 nm.

In some of the embodiments, the purity of a crystalline form of (17-β)-3-Oxoandrost-4-en-17-yl tridecanoate as measured by HPLC is greater than about 90%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.5%, or about 99.9% total area under the curve as observed at a suitable wavelength e.g., about 240 nm or about 242 nm. In some embodiments of the invention, a crystalline form of (17-β)-3-Oxoandrost-4-en-17-yl tridecanoate is about 100.0% pure as measured by HPLC as area under the curve as observed at a suitable wavelength, e.g., at a wavelength of from about 200 nm to about 300 nm, e.g., about 240 nm or 242 nm.

As is understood by the ordinary skilled artisan, solid state NMR and other techniques can be used to analyze or characterize solid EAPI and forms thereof in view of this disclosure.

Production of Different Sizes of Solid State EAPI

Composition having different particles sizes or distributions of particles sizes can be produced by any suitable method. Micronization techniques can be based on friction to reduce particle size; such methods include milling, bashing and grinding. Another technique of producing different sized EAPI particles involves supercritical fluids where the EAPI is dissolved in a solvent at high temperature and pressure and they sprayed out of a nozzle, causing the formation of EAPI particles of particular sizes or within particular size ranges/distributions. Some basic supercritical fluid techniques are RESS process (Rapid Expansion of Supercritical Solutions), the SAS method (Supercritical Anti-Solvent) and the PGSS method (Particles from Gas Saturated Solutions).

Particle Size and Morphology Analysis

Solid state EAPI particles can be analyzed by a number of techniques. For example, Particle size can be analyzed by photon correlation spectroscopy (PCS) using a Malvern ZetaSizer 2000 HS (Malvern Instruments, Malvern, UK). The measuring mode applied can be e.g., Contin-Auto mode. PCS yields the mean diameter of the bulk population (z-average) and a polydispersity index (PI) ranging from 0 (monodisperse) through 0.10-0.20 (relatively monodisperse) to >0.5 for a broad size distribution. The measuring range of PCS is approximately 3 nm-3 μm. As is understood by the ordinary skilled artisan, the parameters and instrumentation for PCS may be modified depending on the instrument, the solid state EAPI and goal(s) of the analysis.

Solid state EAPI can also be analyzed by electron microscopy. Solid particles are deposited on metallic stubs then placed in liquid nitrogen and dried under vacuum. The freeze-dried particles are coated uniformly with gold. All samples are examined for morphology and surface properties using a scanning electron microscope (e.g., Joel, SEM, JSM-25 SII, Tokyo, Japan). Particle size, polydispersity index and zeta potential were initially measured by a laser particle size analyzer (Submicron Particle Size Analyser 90 plus, Brookhaven Instrument Co., Holtsville, NY, USA). An aliquot of solid state EAPI particles can be diluted with e.g., 3 ml of deionized water. The diluted EAPI samples are loaded into a 4 ml cuvette and the particle size and zeta potential measurement can be conducted at e.g., ambient temperature. As is understood by the ordinary skilled artisan, the parameters and instrumentation for electron microscopy may be modified depending on the instrument, the solid state EAPI and goal(s) of the analysis.

The particle size can also be estimated by PXRD e.g., by applying the Sherrer equation which relates the size particles (e.g., crystal particles or crystallites), in a solid to the broadening of a peak in a diffraction pattern.

Release Profile of Solid State EAPI

In one embodiment, the release profile (e.g., a profile comprising 2, 3, 4, 5, or 6 or more time points each at least 5, 10, or 15 minutes apart or a single time point) of solid state (17-β)-3-oxoandrost-4-en-17-yl tridecanoate EAPI does not change substantially as a function of storage time. In one aspect, the release profile of solid state (17-β)-3-Oxoandrost-4-en-17-yl tridecanoate does not substantially change over a period of 1, 2, 3, 4, 5, 6, 7, 8, 9, 10, 11, 12, 13, 14, 15, or 16 weeks. In one aspect, the release profile of solid state (17-β)-3-Oxoandrost-4-en-17-yl tridecanoate does not substantially change over a period of 1, 2, 3, 4, 5, 6, 7, 8, 9, 10, 11, 12, 13, 14, 15, or 16 months. In one aspect, the release profiles is tested using a USP type 2 apparatus at 100 rpm in about 1000 mL 8% Triton X-100 solution in water at a specific temperature e.g., 20.0, 37.0 or 40.0° C. (+0.5). In one aspect, a release profile that does not substantially change over a period of time refers to a release profile that changes by less than plus/minus 50%, 40%, 30%, 20%, or 10% or less of amount (17-β)-3-Oxoandrost-4-en-17-yl tridecanoate released at one or more specific time point under specific conditions.

Pharmaceutical Compositions Having Solid State EAPI

The pharmaceutical compositions and dosage forms (e.g. capsule or tablet) described herein prepared from or comprising solid (17-β)-3-Oxoandrost-4-en-17-yl tridecanoate EAPI can include a variety of pharmaceutically acceptable carriers known in the art. Non-limiting examples of components that can be included as components of the pharmaceutical carrier include lipophilic surfactants, hydrophilic surfactants, triglycerides, fatty acid (C8 to C22), fatty acid glycerides (mono-, di-, tri-, or a combination thereof), or a combination thereof.

In one embodiment, the pharmaceutical composition or dosage form comprises, or is prepared from, solid (17-β)-3-Oxoandrost-4-en-17-yl tridecanoate EAPI as described herein. In a specific aspect of this embodiment, the solid (17-β)-3-Oxoandrost-4-en-17-yl tridecanoate EAPI of the pharmaceutical composition or dosage form is amorphous or substantially amorphous or amorphous-like. Amorphous-like refers to a physical state of the EAPI in a dosage form or pharmaceutical composition in which a substantial amount of the EAPI is not in a structured crystal state (e.g., dissolved in a solvent). In another specific aspect of this embodiment, the solid (17-β)-3-Oxoandrost-4-en-17-yl tridecanoate EAPI of the pharmaceutical composition or dosage form is amorphous or substantially free of crystalline EAPI. In yet another aspect, the pharmaceutical composition or dosage form is prepared from crystalline solid (17-β)-3-Oxoandrost-4-en-17-yl tridecanoate. In yet another aspect, the pharmaceutical composition or dosage form is prepared from a specific crystal form solid (17-β)-3-Oxoandrost-4-en-17-yl tridecanoate. In yet another aspect, the pharmaceutical composition or dosage form is prepared from the crystal form of solid (17-β)-3-Oxoandrost-4-en-17-yl tridecanoate as characterized in the Examples by XRD and DSC.

In yet another aspect, the pharmaceutical composition or dosage form is prepared from crystalline solid (17-β)-3-Oxoandrost-4-en-17-yl tridecanoate and the pharmaceutical composition comprises amorphous or amorphous-like solid (17-β)-3-Oxoandrost-4-en-17-yl tridecanoate. In yet another aspect, the pharmaceutical composition or dosage form is prepared from crystalline solid (17-β)-3-Oxoandrost-4-en-17-yl tridecanoate substantially free of amorphous (17-β)-3-Oxoandrost-4-en-17-yl tridecanoate. In yet another aspect, the pharmaceutical composition or dosage form is prepared from crystalline solid (17-β)-3-Oxoandrost-4-en-17-yl tridecanoate substantially free of amorphous solid (17-β)-3-Oxoandrost-4-en-17-yl tridecanoate and the pharmaceutical composition comprises amorphous or amorphous-like solid (17-β)-3-Oxoandrost-4-en-17-yl tridecanoate substantially free of crystalline solid (17-β)-3-Oxoandrost-4-en-17-yl tridecanoate. In yet another aspect, the pharmaceutical composition or dosage form is prepared from amorphous solid (17-β)-3-Oxoandrost-4-en-17-yl tridecanoate substantially free of crystalline solid (17-β)-3-Oxoandrost-4-en-17-yl tridecanoate and the pharmaceutical composition comprises amorphous or amorphous-like solid (17-β)-3-Oxoandrost-4-en-17-yl tridecanoate substantially free of crystalline solid (17-β)-3-Oxoandrost-4-en-17-yl tridecanoate.

In one embodiment, the pharmaceutical composition or unit dosage form has improved release properties as compared to solid state EAPI (e.g., from which the composition or dosage form is made) without any carriers or excipients. According to this embodiment, a pharmaceutical composition or unit dosage form having a particular amount of (17-β)-3-Oxoandrost-4-en-17-yl tridecanoate (e.g., 3 mg or more, 4 mg or more, 5 mg or more, 10 mg or more, 15 mg or more, 20 mg or more, 30 mg or more, 40 mg or more, 50 mg or more, 75 mg or more, 100 mg or more, 125 mg or more, 150 mg or more, 175 mg or more, 200 mg or more, 225 mg or more, 250 mg or more, 275 mg or more, or 300 mg or more) releases more (17-β)-3-Oxoandrost-4-en-17-yl tridecanoate than a composition (not a pharmaceutical composition or unit dosage form e.g., bulk EAPI) of crystalline EAPI having an equivalent amount of (17-β)-3-Oxoandrost-4-en-17-yl tridecanoate at a specified time point (e.g., 1 min, 2 min, 3 min, 4 min, 5 min, 6 min, 7 min, 8 min, 9 min, 10 min, 11 min, 12 min, 15 min, 20 min, 25 min, 30 min, 35 min, 45 min, 60 min, 75 min, 90 min, 105 min or 120 min) in a USP Type 2 apparatus in about 1000 mL 8% Triton X100 solution in water at a specific temperature (e.g., 20.0, 37.0 or 40.0° C. (±0.5)) at 100 rpm. Releases more in this context refers to releasing more than 10%, 20%, 30%, 40%, 50%, 60%, 70%, 80%, 90% or 100% or more than the bulk EAPI.

In one embodiment, the pharmaceutical composition or unit dosage form having (or made from) solid state EAPI has a release profile (e.g., single time point or multiple time points) of (17-β)-3-Oxoandrost-4-en-17-yl tridecanoate that does not change substantially as a function of storage time as measured using a USP type 2 apparatus in about 1000 mL 8% Triton X100 solution in water at specific temperature (e.g., 20.0, 37.0 or 40.0° C. (+0.5)) at 100 rpm. In one aspect, the release profile does not substantially change over a period of 1, 2, 3, 4, 5, 6, 7, 8, 9, 10, 11, 12, 13, 14, 15, or 16 weeks. In one aspect, the release profile does not substantially change over a period of 1, 2, 3, 4, 5, 6, 7, 8, 9, 10, 11, 12, 13, 14, 15, or 16 months. In one aspect, a release profile that does not substantially change over a period of time refers to a release profile that changes by less than plus/minus 50%, 40%, 30%, 20%, or 10% or less of amount (17-β)-3-Oxoandrost-4-en-17-yl tridecanoate released at one or more specific time point under specific conditions.

In one embodiment, the unit dosage form or pharmaceutical composition as described herein comprising, or prepared from, solid state (17-β)-3-Oxoandrost-4-en-17-yl tridecanoate and a pharmaceutically acceptable carrier, wherein the dosage form or pharmaceutical composition releases 20% or more (17-β)-3-Oxoandrost-4-en-17-yl tridecanoate as measured with a USP Type 2 apparatus having 1000 mL 8% Triton X100 solution in water at thirty minutes at a specific temperature at 100 RPM than a pharmaceutical composition or dosage form comprising or prepared from an equivalent amount of solid state (17-β)-3-Oxoandrost-4-en-17-yl tridecanoate that does not release more than 1% of (17-β)-3-Oxoandrost-4-en-17-yl tridecanoate as measured with a USP Type 2 apparatus having 1000 mL 8% Triton X100 solution in water at thirty minutes, is provided. In one aspect, the bioavailability (e.g., equivalent total dose single dose administration) of a pharmaceutical composition or unit dosage form releasing greater than 10, 20, 30, 40, or 50% or more at 1 hour; 40, 50, 60, or 70% or more at 2 hours; 50, 60, 70, or 80% or more at 3 hours; 60, 70, 80, or 90% or more at 4 hours; or a combination thereof, is substantially improved over a of a pharmaceutical composition or unit dosage form releasing that release less than 50, 45, 35, 30, 25, 20, or 10% at 1 hour; less than 70, 65, 60, 55, 50, 45, 40, 35, 30, 25 or 25% at 2 hours; less than 80, 70, 60, 50, 40, or 30% at 3 hours; less than 90, 85, 80, 75, 70, 60, 50, or 40 at four hours or a combination thereof. In this context, substantially improved refers to a 1.1, 1.2, 1.3, 1.4, 1.5, 1.6, 1.7, 1.8 or more increase in either $AUC_{1\text{-}inf}$ or $AUC_{0\text{-}t}$.

In another embodiment, the pharmaceutical composition or unit dosage form having or made from solid state EAPI has a release profile (e.g., single or multiple point) of (17-β)-3-Oxoandrost-4-en-17-yl tridecanoate using a USP type 2 apparatus in about 1000 mL 8% Triton X100 solution in water at a specific temperature (e.g., 20.0, 37.0 or 40.0° C. (±0.5)) at 100 rpm that releases at least 10, 20, 30, 40, 50, 60, 70, 75, 80, 85, 90, 95, 96, 97, 98, or 99% at 15, 20, 30, 40, 45, 50, 60, 90, 120, 180, 240, or 300 minutes. In a specific aspect, the pharmaceutical composition or unit dosage form having or made from solid state EAPI has a release profile that releases greater than 85% at 4 hours; greater than 70% at 2 hours; or greater than 60% at 1 hour. In a specific aspect, the pharmaceutical composition or unit dosage form having or made from solid state EAPI has a release profile that releases less than 100% at 15 minutes or less than 100% at 30 minutes.

In one embodiment, the pharmaceutical composition or unit dosage form having EAPI has a release profile of (17-β)-3-Oxoandrost-4-en-17-yl tridecanoate using a USP type 2 apparatus in about 1000 mL 8% Triton X100 solution in water at a specific temperature (e.g., 20.0, 37.0 or 40.0° C. (±0.5)) at 100 rpm that releases less than 10, 20, 30, 40, 50, 60, 70, 75, 80, 85, 90, 95, 96, 97, 98, or 99% at 15, 20, 30, 40, 45, 50, 60, 90, 120, 180, 240, or 300 minutes. In a specific aspect, the pharmaceutical composition or unit dosage form having or made from solid state EAPI has a release profile that releases greater than 85% at 4 hours; greater than 70% at 2 hours; or greater than 60% at 1 hour.

In some embodiments, the pharmaceutically acceptable carrier of the composition can include a lipophilic additive. In some embodiments, the lipophilic additive can comprise at least about 20, 25, 30, 35, 40, 45, 50, 55, 60, 65, 70, 75, 80, 85, 90, or 95 wt % or 100 wt % of the pharmaceutically acceptable carrier. In some embodiments, the lipophilic additive can comprise at least about 20, 25, 30, 35, 40, 45, 50, 55, 60, 65, 70, 75, 80, 85, 90, or 95 wt % or 100 wt % of the pharmaceutically composition or unit dosage form. Non-limiting examples of lipophilic additives can include lipophilic surfactants, triglycerides, tocopherol, tocopherol derivatives and combinations thereof. In one embodiment, the lipophilic additive can include a fatty acid or fatty acid glyceride. In another embodiment, lipophilic additive can include the fatty acid glyceride, and the fatty acid glyceride can be a monoglyceride, a diglyceride, or mixtures thereof. Non-limiting examples of fatty acid glycerides that can be used in the oral pharmaceutical compositions and dosage forms of the present invention include monoglycerides and/or diglycerides derived from sources such as maize oil, poppy seed oil, safflower oil, sunflower oil, borage seed oil, peppermint oil, coconut oil, palm kernel oil, castor oil, and mixtures thereof. In one embodiment, the pharmaceutical composition or dosage form thereof comprises 50%, 40%, 30%, 20%, 15%, 10%, 5% by weight or less of a triglyceride. In a specific embodiment, the pharmaceutical composition or dosage form thereof, comprises less than 50% by weight of castor oil. In another embodiment, the composition includes 10 wt % or less of triglycerides. In a further embodiment, the composition includes 5 wt % or less of triglycerides. In a still a further embodiment, the composition includes about 3 wt % or less of triglycerides. In still a further embodiment, the composition includes about 1 wt % or less of triglycerides. In another embodiment, the composition is free or substantially free of triglycerides. In another embodiment, the composition and dosage forms are free of phytosterols and phytosterol fatty acid esters. In one aspect, the lipophilic additive is a C16-C18 saturated fatty acid (or has 1, 2, or 3 unsaturations), a mono-, di-, or triglyceride thereof (including mixtures), or a combination thereof. In a more specific aspect, the C16-C18 fatty acid is stearic acid, oleic acid. In another specific aspect, the mono-, di-, or triglyceride is a glyceride of palmitic acid, stearic acid, oleic acid, linoleic acid or a combination thereof. For example, glyceryl palmitostearate. In one aspect, the pharmaceutical composition or unit dosage forms comprises a PEG (e.g., from 200 to 20000 average molecular weight). In one aspect, the pharmaceutical composition or unit dosage forms comprises peppermint oil. In one aspect, the pharmaceutical composition or unit dosage forms comprises menthol.

In another embodiment, the lipophilic additive can include a lipophilic surfactant.

As used herein a surfactant is considered to be a lipophilic surfactant when it has an HLB value of 10 or less. Various lipophilic surfactants can be used including, but not limited to mono-, di-glycerides of fatty acids like glyceryl monolinoleate (e.g. Maisine® 35-1), mono- and di glycerides of caprylic, capric acid (e.g. Capmul® MCM), glyceryl monooleate, reaction mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (e.g. Labrafil® M 2125 CS), PEG-6 almond oil (e.g. Labrafil® M 1966 CS), PEG-6 apricot kernel oil (e.g. Labrafil® M 1944 CS), PEG-6 olive oil (e.g. Labrafil® M 1980 CS), PEG-6 peanut oil (e.g. Labrafil® M 1969 CS), PEG-6 hydrogenated palm kernel oil (e.g. Labrafil®. M 2130 BS), PEG-6 palm kernel oil (e.g. Labrafil® M 2130 CS), PEG-6 triolein (e.g. Labrafil® M 2735 CS), PEG-8 corn oil (e.g. Labrafil® WL 2609 BS), PEG-20 corn glycerides (e.g. Crovol® M40), PEG-20 almond glycerides (e.g. Crovol® A40), lipophilic polyoxyethylene-polyoxypropylene block co-polymers (e.g.

Pluronic® L92, L101, L121 etc.); propylene glycol fatty acid esters, such as propylene glycol monolaurate (e.g. Lauroglycol FCC), propylene glycol ricinoleate (e.g. Propymuls), propylene glycol monooleate (e.g. Myverol P-O6), propylene glycol dicaprylate/dicaprate (e.g. Captex® 200), and propylene glycol dioctanoate (e.g. Captex® 800), propylene glycol mono-caprylate (e.g. Capryol@ 90); propylene glycol oleate (e.g. Lutrol OP2000); propylene glycol myristate; propylene glycol mono stearate; propylene glycol hydroxy stearate; propylene glycol ricinoleate; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (e.g. Arlacel® 186); sterol and sterol derivatives such as cholesterol, sitosterol, phytosterol, phytosterol fatty acid esters, PEG-5 soya sterol, PEG-10 soya sterol, PEG-20 soya sterol, and the like; glyceryl palmitostearate, glyceryl stearate, glyceryl distearate, glyceryl monostearate, or a combination thereof, sorbitan fatty acid esters such as sorbitan monolaurate (e.g. Arlacel 20), sorbitan monopalmitate (e.g. Span-40), sorbitan monooleate (e.g. Span-80), sorbitan monostearate, and sorbitan tristearate, sorbitan monolaurate, sorbitan monopalmitate, sorbitan monooleate, sorbitan trioleate, sorbitan sesquioleate, sorbitan tristearate, sorbitan monoisostearate, sorbitan sesquistearate, and the like; fatty acids such as capric acid, caprylic acid, oleic acid, linoleic acid, myristic acid, menthol, menthol derivatives, lecithin, phosphatidyl choline, bile salts, and the like, and mixtures thereof. It is important to note that some lipophilic surfactants may also function as the solubilizer component of the compositions and oral dosage forms.

In one embodiment, the lipophilic surfactant can be selected from the group consisting of glyceryl monolinoleate (e.g. Maisine® 35-1), mono- and di glycerides of caprylic, capric acid (e.g. Capmul® MCM), glyceryl monooleate, propylene glycol mono caprylate, propylene glycol oleate, propylene glycol monostearate, propylene glycol monolaurate, propylene glycol mono-oleate, propylene glycol dicaprylate/dicaprate, sorbitan monooleate, PEG-5 hydrogenated castor oil, PEG-7 hydrogenated castor oil, PEG-9 hydrogenated castor oil, PEG-6 corn oil, PEG-6 almond oil, PEG-6 apricot kernel oil, PEG-6 olive oil, PEG-6 peanut oil, PEG-6 hydrogenated palm kernel oil, sorbitan monolaurate (e.g. Arlacel 20), sorbitan monopalmitate, sorbitan monooleate, sorbitan monostearate, sorbitan tristearate, sorbitan monolaurate, sorbitan monopalmitate, sorbitan monooleate, sorbitan trioleate, sorbitan sesquioleate, sorbitan tristearate, sorbitan monoisostearate, and combinations thereof. In some embodiments, the lipophilic surfactants can comprise at least about 10, 20, 30, 40, 50, 60, 70, 80, or 90 wt % of the total pharmaceutically acceptable carrier. It should be noted that the combinations of two or more lipophilic surfactants from the same or different classes therein are also within the scope of this invention and are together can be referred to as the lipophilic surfactant, unless otherwise stated.

In embodiments of the present invention, the oral pharmaceutical compositions or dosage forms (e.g. capsule or tablet) can include a hydrophilic additive. In one embodiment, hydrophilic additive is a selected from the group consisting of hydrophilic surfactant, celluloses—such as hydroxypropyl celluloses low molecular weight, low viscosity types (e.g. Methocel® E5, E6, E10 E15, LV100 etc. grades) and hydroxypropyl celluloses having higher molecular weight, medium to high viscosity (e.g. Methocel® K4M, K15M, K100M etc.); polyvinylpyrrolidones (e.g. Kollidon k17, K30 etc.); polyvinyl acetates and combinations thereof.

In one embodiment, the hydrophilic additive can be a hydrophilic surfactant. A surfactant is considered to be a hydrophilic surfactant when it has an HLB value of greater than 10. Non-limiting examples of hydrophilic surfactants include non-ionic surfactants, ionic surfactants and zwitterionic surfactants. Specifically the hydrophilic surfactants suitable for the current invention include, but not limited to alcohol-oil transesterification products; polyoxyethylene hydrogenated vegetable oils; polyoxyethylene vegetable oils; alkyl sulphate salts, dioctyl sulfosuccinate salts; polyethylene glycol fatty acids esters; polyethylene glycol fatty acids mono- and di-ester mixtures; polysorbates, polyethylene glycol derivatives of tocopherol and the like It should be noted that the combinations of two or more hydrophilic surfactants from the same or different classes are within the scope of this invention and are together can be referred to as the hydrophilic surfactant unless explicitly specified. In one embodiment, the hydrophilic additive can be a hydrophilic surfactant. Non-limiting examples of hydrophilic surfactants can include PEG-8 caprylic/capric glycerides, lauroyl macrogol-32 glyceride, stearoyl macrogol glyceride, PEG-40 hydrogenated castor oil, PEG-35 castor oil, sodium lauryl sulfate, sodium dioctyl sulfosuccinate, polyethylene glycol fatty acids mono- and di-ester mixtures, polysorbate 80, polysorbate 20, polyethylene glycol 1000 tocopherol succinate, phytosterols, phytosterol fatty acid esters, and mixtures thereof.

In some embodiments, surfactants utilized in the pharmaceutical compositions described herein include sterols and derivatives of sterols. In various embodiments, these surfactants are hydrophilic or lipophilic. Examples of hydrophilic sterol surfactants are lanosterol PEG-24 cholesterol ether (e.g. Solulan C-24, Amerchol), PEG-30 soya sterol (e.g. Nikkol BPS-30, from Nikko), PEG-25 phyto sterol (e.g. Nikkol BPSH-25 from Nikko), PEG-30 cholestanol (e.g. Nikkol DHC, from Nikko). Examples of Lipophilic Sterol Surfactants are Cholesterol, sitosterol, Phytosterol (e.g. GENEROL series from Henkel), PEG-5 soya sterol (e.g. Nikkol BPS-S, from Nikko), PEG-10 soya sterol (e.g. Nikkol BPS-10 from Nikko), PEG-20 soya sterol (e.g. Nikkol BPS-20 from Nikko).

In one embodiment, the pharmaceutical composition or unit dosage form includes an additive as described in the following paragraphs.

Suitable additives utilized in various embodiments described herein include, by way of non-limiting example, adsorbing agents, anti-adherents, anticoagulants, antifoaming agents, antioxidants, anti-caking agents, anti-static agents, binders, bile acids, bufferants, bulking agents, chelating agents, coagulants, colorants, co-solvent, opaquants, congealing agents, coolants, cryoprotectants, diluents, dehumidifying agents, desiccants, desensitizers, disintegrants, dispersing agents, enzyme inhibitors, glidants, fillers, hydrating agent, super disintegrants, gums, mucilages, hydrogen bonding agents, enzymes, flavorants, humectants, humidifying agents, lubricant oils, ion-exchange resins, lubricants, plasticizers, pH modifying agents, preservatives, solidifying agent, solvents, solubilizers, spreading agent sweeteners, stabilizers, surface area enhancing agents, suspending agent, thickeners, viscosity increasing agents, waxes and mixtures thereof.

Some non-limiting examples of the additives suitable for the present disclosure may be: alcohols and/or polyols (e.g., ethanol, isopropanol, butanol, benzyl alcohol, ethylene glycol, propylene glycol, glycerol, sorbitol, mannitol, dimethyl isosorbide, polyethylene glycol, fatty acid alcohol, vinyl alcohol polypropylene glycol, polyvinylalcohol, tocopherols, cellulose cyclodextrins, other derivatives, forms, mixtures thereof, or the like); ethers of polyethylene glycols having an average molecular weight of about 200 to about 20,000 (e.g., tetrahydrofurfuryl alcohol PEG ether, methoxy PEG, or the like); amides (e.g., 2-pyrrolidone, 2-piperidone, 8-caprolactam, N-alkylpyrrolidone, N-hydroxyalkylpyrrolidone, N-alkylpiperidone, N-alkylcaprolactam, dimethylacetamide, polyvinylpyrrolidone and the like.); esters (e.g., ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, 8-caprolactone and isomers thereof, 6-valerolactone and isomers thereof, gamma-butyrolactone and isomers thereof; and other additives known in the art, such as dimethyl acetamide, dimethyl isosorbide, N-methylpyrrolidones, monooctanoin, diethylene glycol monoethyl ether, or the like); amino acids (e.g., p-aminobenzamidine, sodium glycocholate) mesylate; amino acids and modified amino acids (e.g., aminoboronic acid derivatives and n-acetylcysteine; peptides and modified peptides (e.g., bacitracin, phosphinic acid dipeptide derivatives, pepstatin, antipain, leupeptin, chymostatin, elastin, bestatin, phoshporamindon, puromycin, cytochalasin potatocarboxy peptidase inhibitor, amastatin, or the like); polypeptide protease inhibitors; mucoadhesive polymers (e.g., polyacrylate derivatives, chitosan, cellulosics, chitosan-EDTA, chitosan-EDTA-antipain, polyacrylic acid, carboxymethyl cellulose etc.) or the like; or combinations thereof.

Some more examples of suitable additives for compositions and/or dosage forms described herein include, by way of non-limiting example, talc, magnesium stearate, silica (e.g., fumed silica, micronized silica, magnesium aluminum silicate etc.) and/or derivatives, polyethylene glycols, surfactants, waxes, oils, cetyl alcohol, polyvinyl alcohol, stearic acid, stearic acid salts, stearic acid derivatives, starch, hydrogenated vegetable oils, hydrogenated castor oils, sodium benzoate, sodium acetate, leucine, PEG, alkyl sulfate salts; acetylated monoglycerides; long-chain alcohols; silicone derivatives; butylated hydroxy toluene (BHT), butylated hydroxyl anisole (BHA), gallic acid, propyl gallate, ascorbic acid, ascorbyl palmitate, 4-hydroxymethyl-2,6-ditert-butyl phenol, dry starch, dry sugars, polyvinyl pyrrolidones, starch paste, methacrylic copolymers, bentonite, sucrose, polymeric cellulose derivatives, shellac, sugar syrup; corn syrup; polysaccharides, acacia, tragacanth, guar gum, xanthan gums; alginates; gelatin; gelatin hydrolysate; agar; sucrose; dextrose; PEG, vinyl pyrrolidone copolymers, poloxamers; pregelatinized starch, sorbitol, glucose); acetic acid, hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, vinegar, pharmaceutically acceptable bases, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamin; salt of a pharmaceutically acceptable cation and an anion; EDTA and EDTA salts; titanium dioxide, food dyes, lakes, natural vegetable colorants, iron oxides, silicates, sulfates, magnesium hydroxide and aluminum hydroxide; halogenated hydrocarbons, trichloroethane, trichloroethylene, dichloromethane, fluorotrichloromethane, diethylether, trehalose, phosphates, citric acid, tartaric acid, gelatin, dextran and mannitol, lactose, mannitol, sodium chloride, potassium chloride, spray-dried lactose, hydrolyzed starches, directly compressible starch, microcrystalline cellulose, cellulosic derivatives, sorbitol, sucrose, sucrose-based materials, calcium sulfate, dibasic calcium phosphate, dextrose, croscarmellose sodium, starch, starch derivatives, clays, gums, cellulose, cellulose derivatives, alginates, crosslinked polyvinylpyrrolidone, sodium starch glycolate and microcrystalline cellulose, magnesium oxide, magnesium carbonates; desensitizers, spray-dried flavors, essential oils, ethyl vanillin, styrene/divinyl benzene copolymers, quaternary ammonium compounds, polyethylene glycol, citrate esters (such as triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl sebacate, ascorbic acid, boric acid, sorbic acid, benzoic acid, and salts thereof, parabens, phenols, benzyl alcohol, and quaternary ammonium compounds; alcohols, ketones, esters, chlorinated hydrocarbons water; sweeteners (e.g., maltose, sucrose, glucose, sorbitol, glycerin and dextrins, aspartame, saccharine, saccharine salts, glycyrrhizin), viscosity modifiers, sugars, polyvinylpyrrolidone, cellulosics, polymers, gums and/or alginates.

In one embodiment, additives may also be materials such as proteins (e.g., collagen, gelatin, Zein, gluten, mussel protein, lipoprotein); carbohydrates (e.g., alginates, carrageenan, cellulose derivatives, pectin, starch, chitosan); gums (e.g., xanthan gum, gum Arabic); spermaceti; natural or synthetic waxes; camauba wax; fatty acids (e.g., stearic acid, hydroxystearic acid); fatty alcohols; sugars; shellacs, such as those based on sugars (e.g., lactose, sucrose, dextrose) or starches; polysaccharide-based shellacs (e.g., maltodextrin and maltodextrin derivatives, dextrates, cyclodextrin and cyclodextrin derivatives); cellulosic-based polymers (e.g., ethyl cellulose, methyl cellulose, microcrystalline cellulose, sodium carboxymethyl cellulose, hydroxypropylmethyl cellulose, ethyl cellulose, hydroxypropyl cellulose, HPMC acid succinates, cellulose acetate, cellulose nitrate, cellulose acetate butyrate, cellulose acetate trimellitate, carboxymethylethyl cellulose, hydroxypropylmethyl cellulose phthalate), shellacs; inorganics, such as dicalcium phosphate, hydroxyapatite, tricalcium phosphate, talc and titania; polyols, such as mannitol, xylitol and sorbitol; polyethylene glycol esters; and polymers, such as alginates, poly(lactide coglycolide), gelatin, crosslinked gelatin, and agar-agar. Non-limiting examples of compounds (e.g., additives) that can be used as at least a part of the pharmaceutically acceptable carrier include without limitation celluloses; dextrins, gums, carbomers, methacrylates, sugars, lactoses, inorganic carbonates, oxides, chlorides, sulphates and the like; salts of calcium; salts of magnesium; salts of fatty acids; inorganic and organic acids, bases and salts; propylene glycol; glycerols; fatty acids; fatty alcohols; fatty acid esters;

glycerol esters; mono-, di- or triglycerides; edible oils; omega oils; vegetable oils, hydrogenated vegetable oils; partially or fully hydrogenated vegetable oils; glycerol esters of fatty acids; waxes; alcohols; gelatin; polyethylene glycol; polyethylene oxide co-polymers; silicates; antioxidants, tocopherols, sugar stearates, starches, shellac, resins, proteins, acrylates; methyl copolymers; polyvinyl alcohol; starch; phthalates; and combinations thereof.

In one embodiment, the additive may include at least one component selected from celluloses, dextrins, gums, carbomers, methacrylates, inorganic carbonates, salts of calcium, salts of magnesium, fatty acids, fatty acid esters, gelatin, lactoses, polyethylene glycol, polyethylene oxide co-polymers, silicates, partially hydrogenated vegetable oils, fully hydrogenated vegetable oils, waxes, antioxidants, tocopherol, sugar stearates, starches, shellac, resins, proteins, and combinations thereof.

In another embodiment, the additive may include at least one component selected from celluloses, dextrins, gums, carbomers, methacrylates, sugars, lactoses, inorganic carbonates, salts of calcium, salts of magnesium, salts of fatty acids, inorganic and organic acids, bases and salts, propylene glycol, glycerols, fatty acids, fatty alcohols, fatty acid esters, glycerol esters, mono-glycerol esters of fatty acids, di-glycerol esters of fatty acids, mixtures of mono-glycerol and di-gylcerol esters of fatty acids, omega oils, waxes, alcohols, gelatin, polyethylene glycol, polyethylene oxide co-polymers, silicates, antioxidants, tocopherol, sugar stearates, starches, shellac, resins, proteins, acrylates, methyl copolymers, polyvinyl alcohol, starch, phthalates, and combinations thereof.

Non-limiting examples of additives as release modulators that may be used include lipophilic resins; ethyl cellulose (EC), methylethyl cellulose (MEC), carboxymethyl ethylcellulose (CMEC), hydroxyethyl cellulose (HEC), cellulose acetate (CA), cellulose propionate (CPr), cellulose butyrate (CB), cellulose acetate butyrate (CAB), cellulose acetate phthalate (CAP), cellulose acetate trimellitate (CAT), hydroxypropyl methyl cellulose phthalate (HPMCP), hydroxypropyl methyl cellulose acetate succinate (HPMCAS), hydroxypropyl methyl cellulose acetate trimellitate (HPMCAT), ion-exchange resin; poloxamers; and ethylhydroxy ethylcellulose (EHEC) tocopherol; shellac; and combinations thereof. Non-limiting examples of lipidic lipophilic release modulators include fatty acids; mono-, di-, tri-esters of fatty acids with glycerol; sucrose esters with fatty acids; cetyl alcohol; stearic acid; glyceryl monostearate; glyceryl distearate; glyceryl tristearate; glyceryl palmitostearate; hydrogenated castor oil; butyl and glycol esters of fatty acids; oleic acid; cetyl alcohol; stearyl alcohol; cetostearyl alcohol; hydrogenated vegetable oil; waxes; bees wax; lard; omega fatty acid esters; hydrogenated soybean oil; hydrogenated vegetable oil; hydrogenated cottonseed and castor oil; partially hydrogenated soybean oil; partially hydrogenated castor oil; partially soy and cottonseed oil; phospholipids; hydrogenated oils, and their derivatives and combinations thereof.

In one embodiment, the oral pharmaceutical composition or the dosage form comprises or is prepared from solid (17-β)-3-Oxoandrost-4-en-17-yl tridecanoate and a pharmaceutically acceptable carrier, wherein (17-β)-3-Oxoandrost-4-en-17-yl tridecanoate comprises about 0.5 wt % to about 75 wt %, about 5 wt % to about 50 wt %, about 10 wt % to about 40 wt %, about 20 wt % to about 40 wt %, about 25 wt % to about 35 wt %, or about 26% to about 32% of the composition or dosage form. In another embodiment, the compositions or the dosage form of the current invention includes solid (17-β)-3-Oxoandrost-4-en-17-yl tridecanoate and a pharmaceutically acceptable carrier, wherein solid (17-β)-3-Oxoandrost-4-en-17-yl tridecanoate comprises about 5 wt % to about 50 wt % of the composition or dosage form, and wherein the carrier includes at least 50 wt % of the composition or the dosage form and wherein the solid (17-β)-3-Oxoandrost-4-en-17-yl tridecanoate is not solubilized at 30° C., or above 30° C., or at a temperature range above 30° C., including 30° C. to about 40° C. In an additional more specific embodiment, the solid (17-β)-3-Oxoandrost-4-en-17-yl tridecanoate is not fully dissolved in the carrier at human body temperature. In one aspect, the carrier includes a C16-C18 saturated fatty acid (or has 1, 2, or 3 unsaturations), a mono-, di-, or triglyceride thereof (including mixtures), or a combination thereof. In a more specific aspect, the C16-C18 fatty acid is stearic acid, oleic acid. In another specific aspect, the mono-, di-, or triglyceride is a glyceride of palmitic acid, stearic acid, oleic acid, linoleic acid or a combination thereof. For example, glyceryl palmitostearate. In one aspect, the pharmaceutical composition or unit dosage forms comprises a PEG (e.g., from 200 to 20000 average molecular weight). In one aspect, the pharmaceutical composition or unit dosage forms comprises peppermint oil. In one aspect, the pharmaceutical composition or unit dosage forms comprises menthol. In one aspect, the unit dosage form is a hard gel or soft gel capsule or a tablet.

In another embodiment, the compositions or the dosage forms includes or is prepared from solid (17-β)-3-Oxoandrost-4-en-17-yl tridecanoate EAPI and a pharmaceutically acceptable carrier, wherein the (17-β)-3-Oxoandrost-4-en-17-yl tridecanoate comprises about 5 wt % to about 50 wt % of the composition or the dosage form, and wherein the carrier includes about 50 wt % to about 100 wt % of lipophilic surfactant and 0 wt % to about 50 wt % of hydrophilic surfactant. In one aspect, the (17-β)-3-Oxoandrost-4-en-17-yl tridecanoate comprises %, about 20 wt % to about 40 wt %, about 25 wt % to about 35 wt %, or about 26% to about 32% of the composition or dosage form. In a further embodiment, the ester is not solubilized at 30° C., or above 30° C., or at a temperature range above 30° C., including 30° C. to about 40° C. In an additional more specific embodiment, the solid (17-β)-3-Oxoandrost-4-en-17-yl tridecanoate is not fully dissolved in the carrier at human body temperature. In one aspect, the carrier includes a C16-C18 saturated fatty acid (or has 1, 2, or 3 unsaturations), a mono-, di-, or triglyceride thereof (including mixtures), or a combination thereof. In a more specific aspect, the C16-C18 fatty acid is stearic acid, oleic acid. In another specific aspect, the mono-, di-, or triglyceride is a glyceride of palmitic acid, stearic acid, oleic acid, linoleic acid or a combination thereof. For example, glyceryl palmitostearate. In one aspect, the pharmaceutical composition or unit dosage forms comprises a PEG (e.g., from 200 to 20000 average molecular weight). In one aspect, the pharmaceutical composition or unit dosage forms comprises peppermint oil. In one aspect, the pharmaceutical composition or unit dosage forms comprises menthol. In one aspect, the unit dosage form is a hard gel or soft gel capsule or a tablet.

In another specific embodiment, the composition or the dosage form includes or is prepared from solid (17-β)-3-Oxoandrost-4-en-17-yl tridecanoate EAPI and a pharmaceutically acceptable carrier, wherein (17-β)-3-Oxoandrost-4-en-17-yl tridecanoate comprises about 5 wt % to about 50 wt % of the composition or the dosage form, and the carrier includes about 50 wt % to about 95 wt % a lipophilic surfactant and a hydrophilic surfactant 5 wt % to about 30 wt %. In one aspect, the (17-β)-3-Oxoandrost-4-en-17-yl tridecanoate comprises %, about 20 wt % to about 40 wt %, about 25 wt % to about 35 wt %, or about 26% to about 32% of the composition or dosage form. In one aspect, the composition or dosage form comprises less than 25, 20, 15, 10, 8, 5, 4, 3, 2, or 1 wt % hydrophilic surfactant. In a further more specific embodiment, the EAPI is not solubilized at 30° C., or above 30° C., or at a temperature range above 30° C., including 30° C. to about 40° C. In an additional more specific embodiment, the EAPI is not fully dissolved in the carrier at human body temperature. In another more specific embodiment, the composition or the dosage form can optionally contain about less than 10, 9, 8, 7, 6, 5, 4, 3, 2, or 1 wt % ethyl alcohol or has about 0 wt %. In one aspect, the carrier includes a C16-C18 saturated fatty acid (or has 1, 2, or 3 unsaturations), a mono-, di-, or triglyceride thereof (including mixtures), or a combination thereof. In a more specific aspect, the C16-C18 fatty acid is stearic acid, oleic acid. In another specific aspect, the mono-, di-, or triglyceride is a glyceride of palmitic acid, stearic acid, oleic acid, linoleic acid or a combination thereof. For example, glyceryl palmitostearate. In one aspect, the pharmaceutical composition or unit dosage forms comprises a PEG (e.g., from 200 to 20000 average molecular weight). In one aspect, the pharmaceutical composition or unit dosage forms comprises peppermint oil. In one aspect, the pharmaceutical composition or unit dosage forms comprises menthol. In one aspect, the unit dosage form is a hard gel or soft gel capsule or a tablet.

In one embodiment, the hydrophilic surfactant can comprise at least about 20% of the total pharmaceutical carrier. In one aspect, the (17-β)-3-Oxoandrost-4-en-17-yl tridecanoate comprises %, about 20 wt % to about 40 wt %, about 25 wt % to about 35 wt %, or about 26% to about 32% of the composition or dosage form. In another embodiment, the hydrophilic surfactant can comprise at least about 1, 2, 3, 4, 5, 10, 15, or 20 wt % of the carrier. In another embodiment, the hydrophilic surfactant can comprise less than 20, 15, 10, 6, 5, 4, 3, 2, or 1 wt % of the carrier or no hydrophilic surfactant is present in the carrier. In a related aspect, the hydrophilic surfactant can comprise at least about 20% of the total pharmaceutical composition (e.g., EAPI and carrier). In another embodiment, the hydrophilic surfactant can comprise at least about 1, 2, 3, 4, 5, 10, 15, or 20 wt % of the pharmaceutical composition. In another embodiment, the hydrophilic surfactant can comprise less than 20, 15, 10, 6, 5, 4, 3, 2, or 1 wt % of the pharmaceutical composition or no hydrophilic surfactant is present. In one aspect, the carrier includes a C16-C18 saturated fatty acid (or has 1, 2, or 3 unsaturations), a mono-, di-, or triglyceride thereof (including mixtures), or a combination thereof. In a more specific aspect, the C16-C18 fatty acid is stearic acid or oleic acid. In another specific aspect, the mono-, di-, or triglyceride is a glyceride of palmitic acid, stearic acid, oleic acid, linoleic acid or a combination thereof. For example, glyceryl palmitostearate. In one aspect, the pharmaceutical composition or unit dosage forms comprises a PEG (e.g., from 200 to 20000 average molecular weight). In one aspect, the pharmaceutical composition or unit dosage forms comprises peppermint oil. In one aspect, the pharmaceutical composition or unit dosage forms comprises menthol. In one aspect, the unit dosage form is a hard gel or soft gel capsule or a tablet.

In another embodiment, the composition or the dosage form includes or is prepared from solid (17-β)-3-Oxoandrost-4-en-17-yl tridecanoate EAPI, wherein the (17-β)-3-Oxoandrost-4-en-17-yl tridecanoate comprises about 5 wt % to about 50 wt % of the composition or the dosage form, and wherein the composition includes about 50 wt % to about 100 wt % of lipophilic additive and 0 wt % to about 50 wt % of hydrophilic additive. In one aspect, the (17-β)-3-Oxoandrost-4-en-17-yl tridecanoate comprises about 20 wt % to about 40 wt %, about 25 wt % to about 35 wt %, or about 26% to about 32% of the composition or dosage form. In a specific embodiment, the lipophilic additive can be lipophilic surfactant and the hydrophilic additive can be hydrophilic surfactant. In a further embodiment, the ester is not solubilized at 30° C., or above 30° C., or at a temperature range above 30° C., including 30° C. to about 40° C. In an additional more specific embodiment, the EAPI is not fully dissolved in the lipophilic additive or the composition at human body temperature. In one aspect, the carrier includes a C16-C18 saturated fatty acid (or has 1, 2, or 3 unsaturations), a mono-, di-, or triglyceride thereof (including mixtures), or a combination thereof. In a more specific aspect, the C16-C18 fatty acid is stearic acid or oleic acid. In another specific aspect, the mono-, di-, or triglyceride is a glyceride of palmitic acid, stearic acid, oleic acid, linoleic acid or a combination thereof. For example, glyceryl palmitostearate. In one aspect, the pharmaceutical composition or unit dosage forms comprises a PEG (e.g., from 200 to 20000 average molecular weight). In one aspect, the pharmaceutical composition or unit dosage forms comprises peppermint oil. In one aspect, the pharmaceutical composition or unit dosage forms comprises menthol. In one aspect, the unit dosage form is a hard gel or soft gel capsule or a tablet.

In some embodiments, the oral pharmaceutical composition or the dosage form can include both a lipophilic surfactant and hydrophilic surfactant. In one aspect, the (17-β)-3-Oxoandrost-4-en-17-yl tridecanoate comprises about 20 wt % to about 40 wt %, about 25 wt % to about 35 wt %, or about 26 wt % to about 32 wt % of the composition or dosage form. In one embodiment, the lipophilic surfactant and hydrophilic surfactant can be present in amounts such that the ratio of amount (wt %) of lipophilic surfactant to amount (wt %) of hydrophilic surfactant is greater than 2:1. In another embodiment, the lipophilic surfactant and hydrophilic surfactant can be present in amounts such that the ratio of amount (wt %) of lipophilic surfactant to amount (wt %) of hydrophilic surfactant is greater than 2.5:1. In another embodiment, the lipophilic surfactant and hydrophilic surfactant can be present in amounts such that the ratio of amount (wt %) of lipophilic surfactant to amount (wt %) of hydrophilic surfactant is greater than 3.5:1. In still another embodiment, the lipophilic surfactant and hydrophilic surfactant can be present in amounts such that the ratio of amount (wt %) of lipophilic surfactant to amount (wt %) of hydrophilic surfactant is at least 6.5:1.

Methods of Using Solid State EAPI and Products Derived Therefrom

In one embodiment, a pharmaceutical composition prepared by synthesizing (17-β)-3-Oxoandrost-4-en-17-yl tridecanoate to produce crystalline (17-β)-3-Oxoandrost-4-en-17-yl tridecanoate solid and mixing the crystalline (17-β)-3-Oxoandrost-4-en-17-yl tridecanoate with one or more pharmaceutically acceptable carriers to provide a pharmaceutical composition which is substantially free of crystalline (17-β)-3-Oxoandrost-4-en-17-yl tridecanoate. In a related embodiment, a pharmaceutical composition is prepared by providing crystalline (17-β)-3-Oxoandrost-4-en-17-yl tridecanoate solid and mixing the crystalline (17-β)-3-Oxoandrost-4-en-17-yl tridecanoate with one or more pharmaceutically acceptable carriers to provide a pharmaceutical composition which is substantially free of crystalline (17-β)-3-Oxoandrost-4-en-17-yl tridecanoate.

Methods of Use

The solid state EAPI, pharmaceutical compositions comprising or prepared from the solid state EAPI, and unit dosage forms comprising or prepared the solid state EAPI have a number of uses.

Subjects that can be treated by pharmaceutical compositions and unit dosage forms of the present disclosure (e.g., prepared from or comprising solid state (17-β)-3-Oxoandrost-4-en-17-yl tridecanoate) can be any mammal (e.g., a human male or female) in need thereof. In particular, in one embodiment, the human male may be at least 14 years of age. In another embodiment, the human male is an adult of at least age 16, 18, or 20. In another embodiment, the human male is an adult of at least age 21, 23, or 25. In another embodiment, the human male is an adult of at least age 30. In a further embodiment, the subject can be an adult male of at least age 50. In yet a further embodiment, the subject can be an adult male of at least age 60. Subjects that can be treated by pharmaceutical compositions and unit dosage forms of the present disclosure (e.g., prepared from or comprising solid state (17-β)-3-Oxoandrost-4-en-17-yl tridecanoate) can be any human male in need thereof. In particular, in one embodiment, the human female may be at least 14 years of age. In another embodiment, the human female is an adult of at least age 30. In a further embodiment, the subject can be an adult female of at least age 50. In a further embodiment, the subject can be an adult female who has deficient endogenous serum testosterone levels. In a further embodiment, the subject can be an adult female who has undergone unilateral or bilateral oophorectomy. In yet a further embodiment, the subject can be an adult female who has undergone unilateral or bilateral oophorectomy. In yet another embodiment, the subject can be a post-menopausal woman.

As discussed above, the present invention also provides for a method of treating a human subject in need of testosterone therapy is provided. The method can include the steps of administering any of the pharmaceutical compositions or dosage forms (e.g., capsule or tablet) disclosed herein. The pharmaceutical compositions and the dosage forms of the present invention can be used to treat any condition associated with testosterone deficiency, including complete absence, of endogenous testosterone in male or female subjects. Examples of conditions associated with testosterone deficiency that can be treated using the dosage forms (e.g., capsule or tablet) and/or compositions of the present invention include, but are not limited to congenital or acquired primary hypogonadism, hypogonadotropic hypogonadism, cryptorchidism, bilateral torsion, orchitis, vanishing testis syndrome, orchidectomy, Klinefelter's syndrome, post castration, eunuchoidism, hypopituitarism, endocrine impotence, infertility due to spermatogenic disorders, impotence, male sexual dysfunction (MSD) including conditions such as premature ejaculation, erectile dysfunction, decreased libido, and the like, micropenis and constitutional delay, penile enlargement, appetite stimulation, testosterone deficiency associated with chemotherapy, testosterone deficiency associated with toxic damage from alcohol, testosterone deficiency associated with toxic damage from heavy metal, osteoporosis associated with androgen deficiency, and combinations thereof.

Other conditions that can be treated by the compositions and dosage forms disclosed herein include idiopathic gonadotropin, LHRH deficiency, or pituitary hypothalamic injury from tumors, trauma, or radiation. Typically, these subjects have low serum testosterone levels but have gonadotropins in the normal or low range. In one embodiment, the compositions or oral dosage forms may be used to stimulate puberty in carefully selected males with clearly delayed puberty not secondary to a pathological disorder. In another embodiment, the compositions and oral dosage forms may be used in female-to-male transsexuals in order to maintain or restore male physical and sexual characteristics including body muscle mass, muscle tone, bone density, body mass index (BMI), enhanced energy, motivation and endurance, restoring psychosexual activity etc. In some embodiments, pharmaceutical compositions and unit dosage forms of the present disclosure (e.g., prepared from or comprising solid state (17-β)-3-Oxoandrost-4-en-17-yl tridecanoate) can be useful in providing hormonal male contraception. In some embodiments, pharmaceutical compositions and unit dosage forms of the present disclosure (e.g., prepared from or comprising solid state (17-β)-3-Oxoandrost-4-en-17-yl tridecanoate) can be used to provide treatment of one or more symptoms associated with female sexual dysfunction, anorgasmia, osteoarthritis, hormonal male contraception. Additionally, pharmaceutical compositions and unit dosage forms of the present disclosure (e.g., prepared from or comprising solid state (17-β)-3-Oxoandrost-4-en-17-yl tridecanoate) can be used to treat and/or improve the patient related outcomes including the quality of life and wellbeing of the subjects suffering from deficiency of endogenous testosterone. In some embodiments, pharmaceutical compositions and unit dosage forms of the present disclosure (e.g., prepared from or comprising solid state (17-β)-3-Oxoandrost-4-en-17-yl tridecanoate) can be used to treat or improve the symptoms of subjects suffering from conditions such as decreased libido, diminishing memory, anemia due to marrow failure, renal failure, chronic respiratory or cardiac failure, steroid-dependent autoimmune disease, muscle wasting associated with various diseases such as AIDS, preventing attacks of hereditary angioedema or urticaria; andropause, and palliating terminal breast cancer. In some situations, certain biomarkers such as for example, increased SHBG levels, can be used to diagnose a subject who may be in need of testosterone therapy. These biomarkers can be associated with conditions/disease states such as anorexia nervosa, hyperthyroidism, hypogonadism, androgen insensitivity/deficiency, alcoholic hepatic cirrhosis, primary biliary cirrhosis, and the like.

It has been discovered that pharmaceutical compositions (or unit dosage forms) prepared from or comprising specific solid state (17-β)-3-Oxoandrost-4-en-17-yl tridecanoate have a unique daily dose range for which, upon daily administration to each subject in a group (e.g., of at least for example 12 hypogonadal males) for a period of at least 84 days, provides a serum testosterone $C_{avg}$ of 300 ng/dL to 1100 ng/dL in at least 75% of the hypogonadal males in the group, and at least one of the following:

a steady state serum T concentration of <300 ng/dL for no more than 7 hours in a 24-hour period in 50% or less of the subjects.

a steady state serum T concentration of >300 ng/dL for at least 12-24 hours post-dosing in a 24-hour period in majority of the subjects.

a steady state serum T concentration serum T levels of <300 ng/dL for no more than 7 hours in a 24-hour period in 50% or less subjects, 300 ng/dL for at least 12-24 hours post-dosing in a 24-hour period in majority of the subjects.

a serum testosterone $C_{max}$ of less than 1500 ng/dL in at least 85% of the subjects in the group;

a serum testosterone $C_{max}$ of about 1800 ng/dL to about 2500 ng/dL in 5% or less of the subjects in the group; and a serum testosterone $C_{max}$ greater than 2500 ng/dL in about 1% or less of the subjects in the group.

Contrary to expectations based on teachings in the art, it has been found that compositions prepared from or comprising solid state (17-β)-3-Oxoandrost-4-en-17-yl tridecanoate have unexpected lower solubility in most of the commonly desired lipid solvents for (17-β)-3-Oxoandrost-4-en-17-yl tridecanoate oral compositions. Given its unique effective daily dose range it presents a challenge to design compositions leading to patient-friendly dosage form and dosing regimen. It has been found that oral compositions prepared from or comprising solid state (17-β)-3-Oxoandrost-4-en-17-yl tridecanoate need not be dissolved under ambient conditions or at human body temperature, be solubilized or be in solution (e.g. at or above 30° C., or at 30° C. to 40° C. etc.) to provide the mean serum T $C_{avg\ t12\text{-}t24}$ within the desirable effective eugonadal range upon single oral administration, such that serum T levels are sustained in most of the patients at levels >300 ng/dL for a large percentage of the dosing period with a patient-friendly regimen with lower dosing frequency administration in a day and/or with fewer number of dosage units per administration.

Accordingly, it has been discovered that by having a significant not dissolved or not solubilized fraction comprising solid state (17-β)-3-Oxoandrost-4-en-17-vi tridecanoate dose in the composition or dosage form, one can achieve a practical dosing regimen with adequate drug loading in the composition/dosage form that allows for adequate bioavailable testosterone levels restoration with manageable dosage units per dose and thus, an oral therapy for treatment of hypogonadism that is convenient, safe (e.g., $C_{max}$ no more than 1500 ng/dL), effective (e.g., mean $C_{avg\ t0\text{-}t24}$ within the eugonadal range of 300 ng/dL to 1100 ng/dL), and longer lasting (e.g., mean serum T $C_{avg\ t12\text{-}t24}$ at greater than 300 ng/dL upon a single administration).

The compositions and unit dosage forms can be prepared by any suitable method known to the skilled artisan or developed in view of the teachings herein.

In one specific aspect, the carrier(s) and API are brought to or maintained at a temperature at which they are flowable (e.g., above 10° C., 20° C., 25° C., 30° C., 35° C., or 40° C.). In one aspect, the mixture of carrier and API is a clear solution at a specified temperature (e.g., above 10° C., 20° C., 25° C., 30° C., 35° C., or 40° C.). In one aspect, the mixture of carrier and API is a cloudy or hazy solution at a specified temperature (e.g., below 10° C., 20° C., 25° C., 30° C., 35° C., or 40° C.).

In one example, the composition is prepared by weighing all of the components, except the API into a clean stainless steel container and mixed together at ambient temperature or at elevated temperatures e.g., at about 25° C. to about 30° C., at about 30° C. to about 35° C., at about 35° C. to about 40° C., at about 40° C. to about 45° C., at about 45° C. to about 45° C., or 50° C. to about 70° C., using a stirrer. The API is added and stirred into the mixture of other components until the API dissolves. A predetermined quantity of this "liquid fill material" is disposed into a capsule (for example, hard gelatin capsule) to get the required API dose per dosage unit. The capsules are allowed to cool at room temperature, banded (if required) and packaged in a HDPE bottle and tightly closed with an appropriate lid. It is noted that various capsule sizes (e.g., hard gel or soft gel) are available to the skilled artisan and allow for variations in the amount of loading of API in mg per unit dosage form. Typically, soft gel capsules for oral administration have fill volumes of less than 1.5 mL, 1.3 mL or 1.25 mL with numerous incremental fill volumes in these ranges. Similarly, hard gel capsules typically have fill volumes of less than 1.25 mL, 1.10 mL or 1 mL. Due to the nature of some hard gel capsules, the total fill volume may not be useable. There is a practical limit on the temperature at which capsules can be filled—for example temperature above 40° C. typically melt, deform, or otherwise damage soft gel capsules typically employed in the industry. Hard gel capsules are typically less sensitive to temperature and can be filled at higher temperatures e.g., above 40° C.

In certain embodiments, any pharmaceutical composition described herein, e.g., a can be prepared by (i) combining and heating all ingredients until a molten mixture is obtained (e.g., 50-70° C.); and (ii) encapsulating an amount of molten mixture comprising a select dose (e.g., a therapeutically effective amount or a partial dose of a therapeutically effective amount) API to obtain an oral dosage form. In certain instances, the molten mixture is spray-congealed to obtain beads. In some instances, the molten mixture is sprayed onto inert cores (e.g., sugar spheres) to obtain coated cores. In certain embodiments, such beads, cores, or similar forms are encapsulated or otherwise formulated to provide an oral dosage form. In some instances, the molten mixture is admixed, uniformly dispersed, or granulated over a carrier and compressed into a tablet dosage form. In certain embodiments, prior to compression, the molten mixture/carrier composition is further mixed with one or more pharmaceutical aid including, by way of non-limiting example, glidants, lubricants, binders, or the like. In some embodiments, the carrier is a therapeutically inert carrier such as, by way of non-limiting example, microcrystalline cellulose, starch, lactose, or the like.

In various embodiments, pharmaceutical compositions described herein are formulated as oral dosage forms. Oral dosage forms are prepared by any suitable process including one or more steps of, by way of non-limiting example, agglomeration, air suspension chilling, air suspension drying, balling, coacervation, comminution, compression, pelletization, cryopelletization, encapsulation, extrusion, granulation, homogenization, inclusion complexation, lyophilization, nanoencapsulation, melting, mixing, molding, pan coating, solvent dehydration, sonication, spheronization, spray chilling, spray congealing, spray drying, or the like.

In some embodiments, a pharmaceutical composition described herein is formulated with a substrate to form an oral dosage form. In various embodiments, substrates useful for formulating pharmaceutical compositions described herein as oral dosage forms include or comprise, by way of non-limiting example, a powder or a multiparticulate (e.g., one or more granule, one or more pellet, one or more bead, one or more spherule, one or more beadlet, one or more microcapsule, one or more millisphere, one or more mini capsule, one or more microcapsule, one or more nanocapsule, one or more nanosphere, one or more microsphere, one or more minitablet, one or more tablet, one or more capsule, or one or more combinations thereof). In certain instances, a powder constitutes a finely divided (milled, micronized, nanosized, precipitated) form of an active ingredient or additive molecular aggregates or a compound aggregate of multiple components or a physical mixture of aggregates of an active ingredient and/or additives.

The following examples are provided to promote a more clear understanding of certain embodiments of this disclosure and are in no way meant as a limitation thereon.

EXAMPLE 1: Preparation of Solid State EAPI

A non-limiting exemplary synthetic scheme for producing a solid state ester of active pharmaceutical ingredient (EAPI) as disclosed herein is shown in FIG. 1A and is outlined in more detail below. The EAPI can be produced utilizing the generalized scheme set forth below:
1) (17-β)-Hydroxy-4-Androsten-3-one (0.1 mol) is weighed into a 1000 mL 4N RB flask containing a stir bar.
2) Pyridine (160 mL) is added to the flask.
3) The flask is placed in an ice-water bath and fitted with a nitrogen inlet, addition funnel, thermocouple, and stopper. Stirring and nitrogen flow are started.
4) The funnel is charged with a solution of acid chloride (1.56 equiv. e.g., acid chloride of tridecanoic acid) in heptane (160 mL), then fitted with an adapter connected to a bubbler.
5) The contents of the funnel are added dropwise over 30-40 min (Note: the internal temperature increases 5-7° C. during the addition.)
6) When the addition is complete, the bath is removed and stirring is continued.
7) After 1 h, the reaction mixture is transferred to a large separatory funnel and diluted with heptane (1000 mL) (Note: TLC at 1 h indicates a complete reaction).
8) The heptane solution is washed successively with 800 mL portions of: cold water (2×), 0.05 N NaOH, saturated NaHCO$_3$ (2×), water, brine, then dried over anhydrous Na$_2$SO$_4$ (~50 g). Then concentrated to dryness (rotavap/Tbath:S; 30° C.).

EXAMPLE 2: Preparation of Solid State EAPI Crystals

Figure 1B:
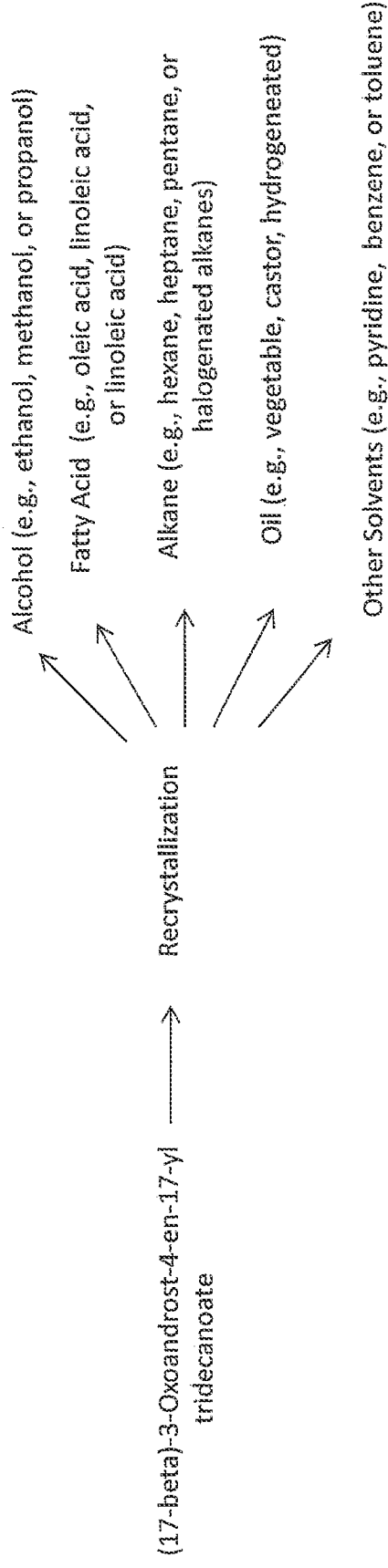
FIG. 1B shows non-limiting examples of methods for crystallizing solid state forms of (17-β)-3-Oxoandrost-4-en-17-yl tridecanoate disclosed herein.

A reaction mixture or product of Example 1 (or material produce by another route) can be transferred to water, ethanol, or methanol (or any other appropriate solvent) and allowed to crystallize. The crystalline mass can be filtered by suction, washed with water, dried over phosphorous pentoxide and re-crystallized from another solvent (although this step is not necessary) e.g., oleic acid, hexane, heptanes, etc. See FIG. 1B

EXAMPLE 3: Differential Scanning Calorimetry of Solid State EAPI

Figure 2:
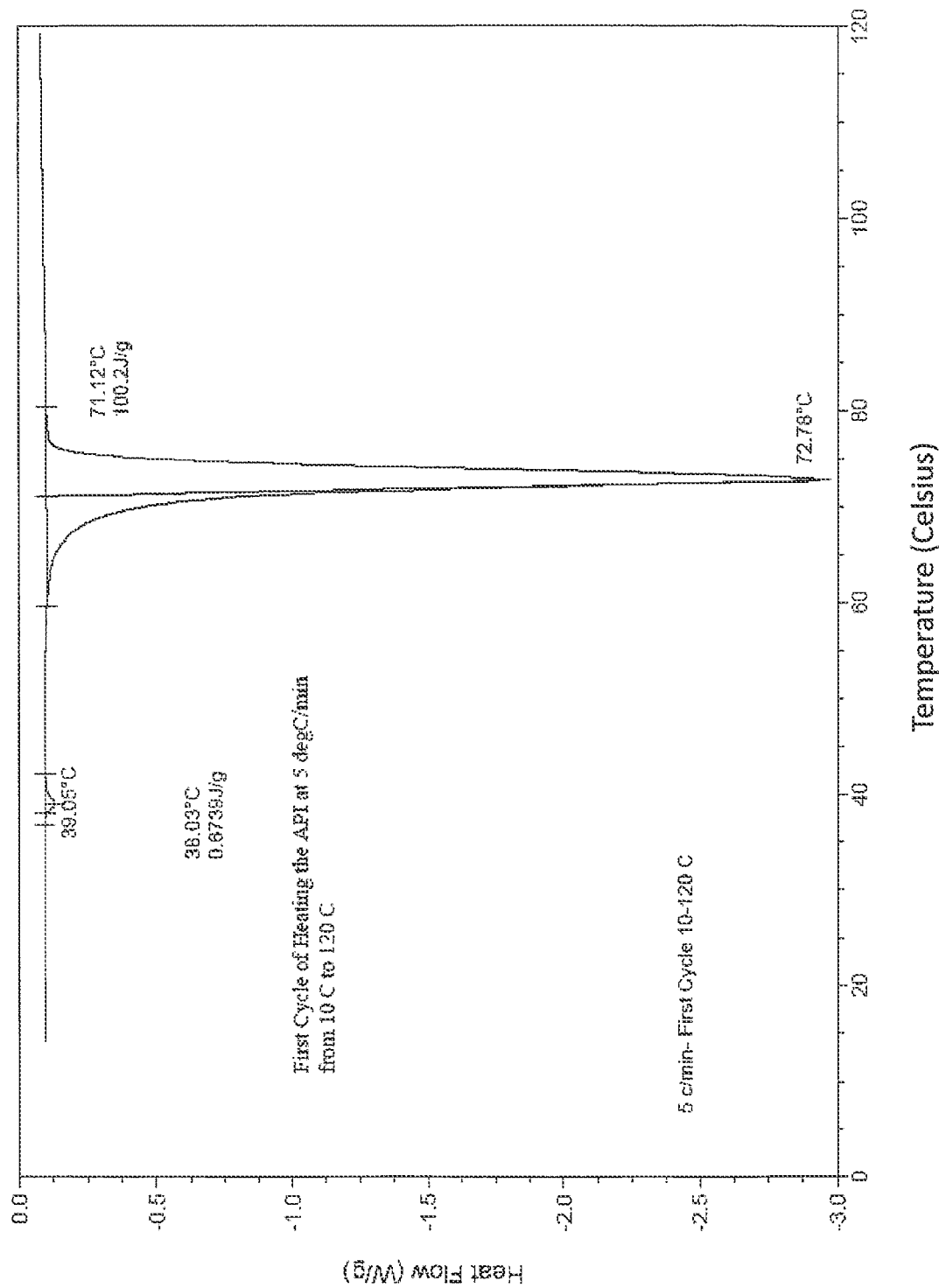
FIG. 2 shows a differential scanning calorimetry first heat cycle plot for a solid state form of (17-β)-3-Oxoandrost-4-en-17-yl tridecanoate as disclosed herein.
Figure 3:
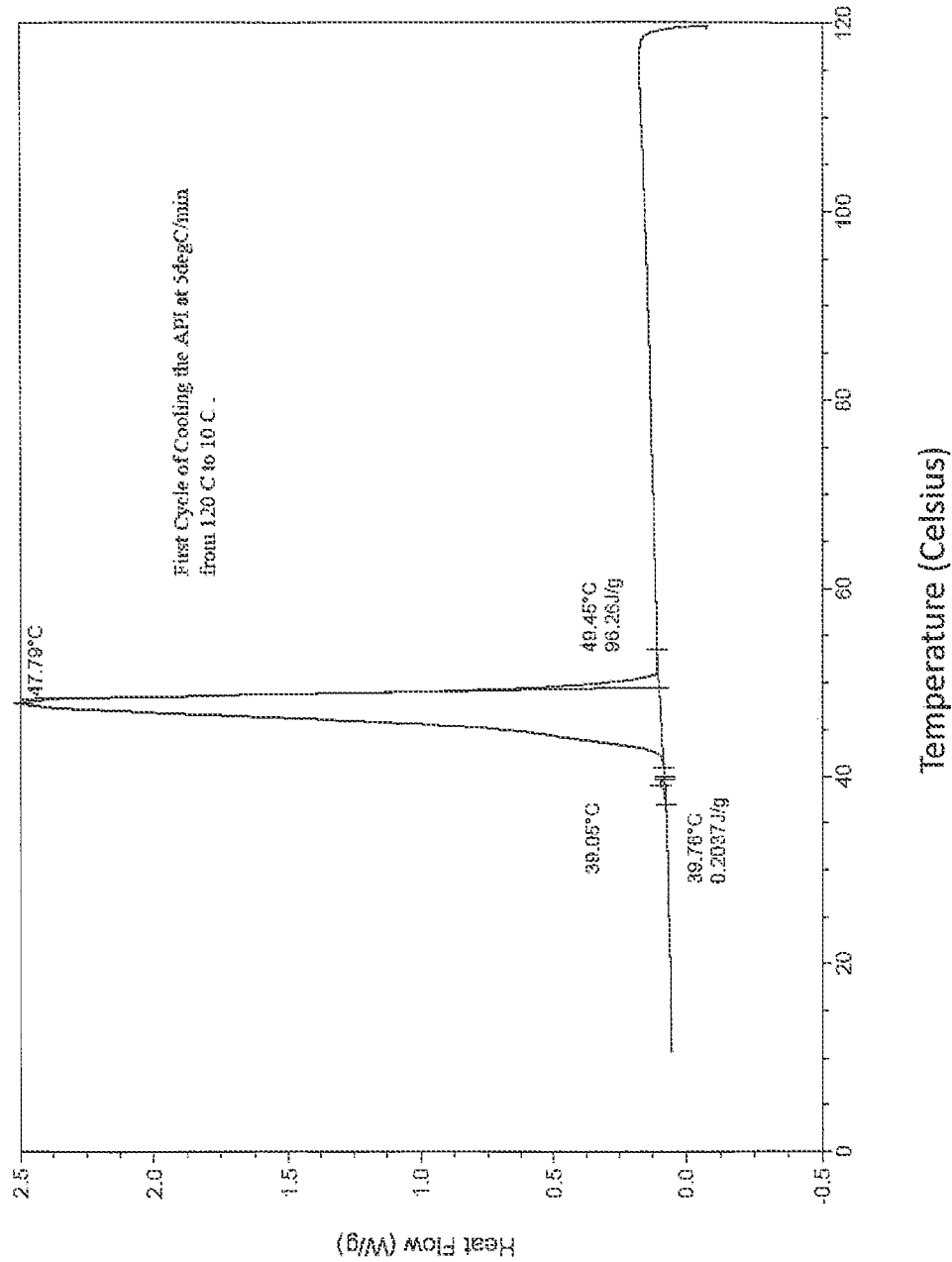
FIG. 3 shows a differential scanning calorimetry first cool cycle plot for a solid state form of (17-β)-3-Oxoandrost-4-en-17-yl tridecanoate as disclosed herein.
Figure 4:
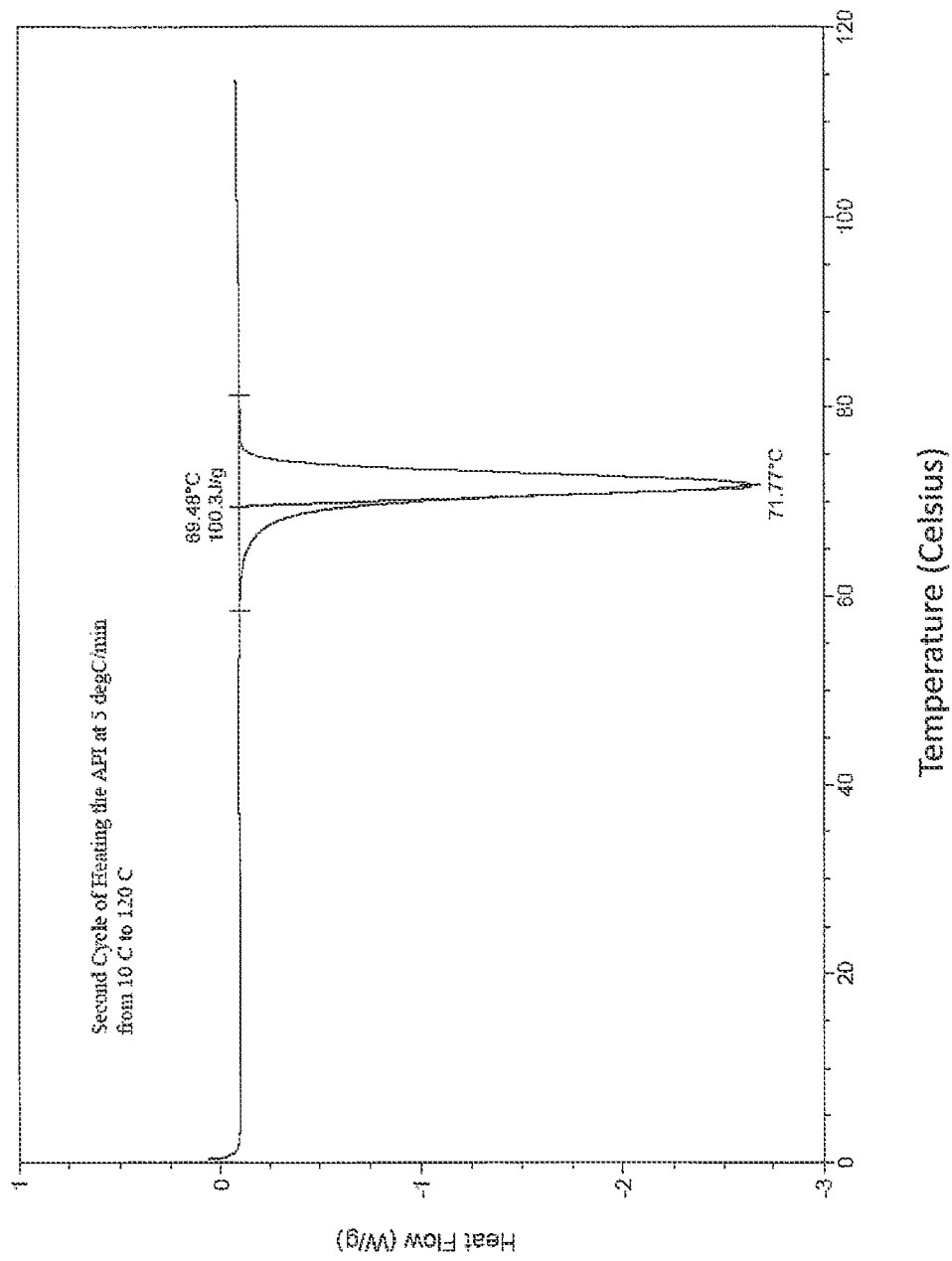
FIG. 4 shows a differential scanning calorimetry second heat cycle plot for a solid state form of (17-β)-3-Oxoandrost-4-en-17-yl tridecanoate as disclosed herein.
Figure 5:
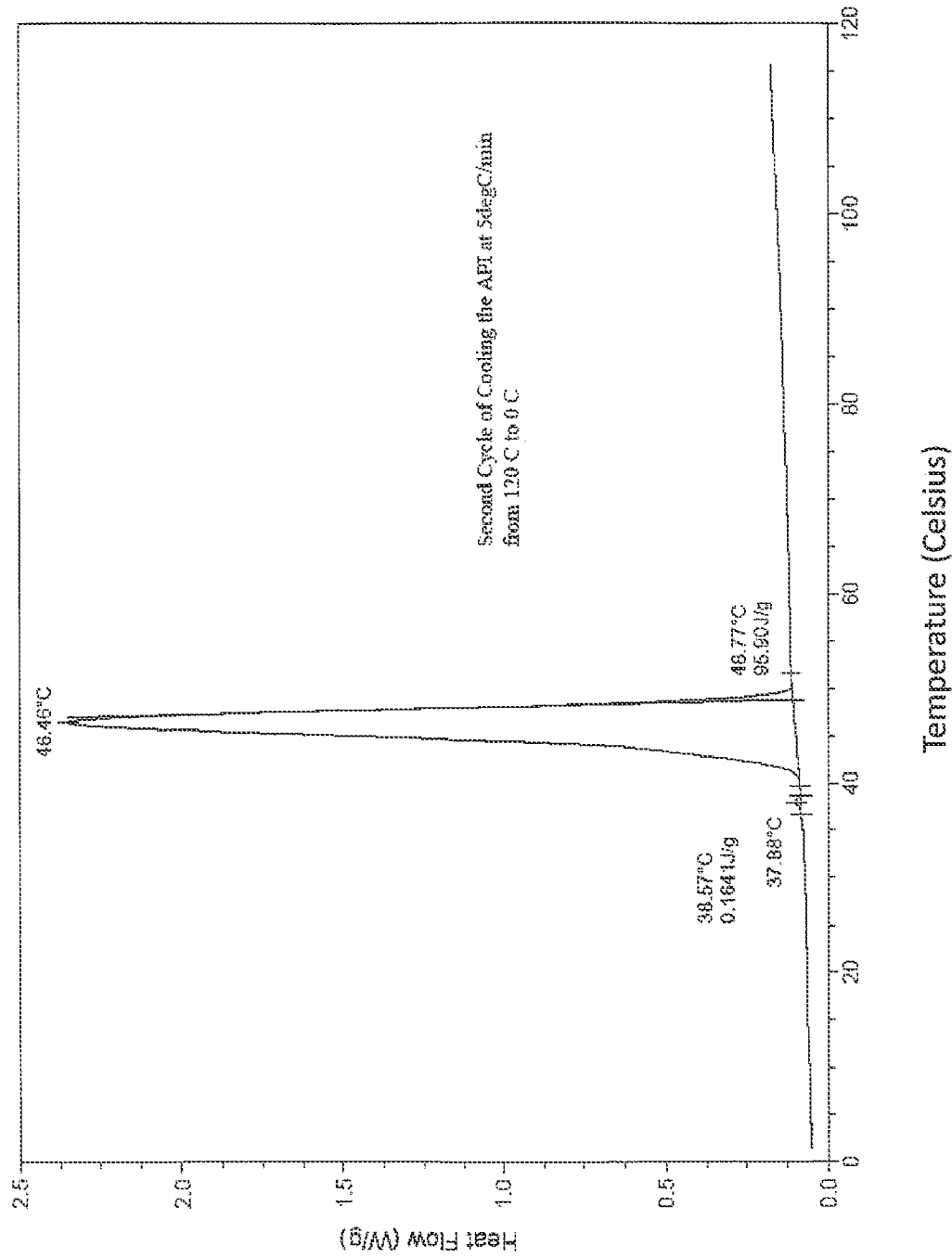
FIG. 5 shows a differential scanning calorimetry second cool cycle plot for a solid state form of (17-β)-3-Oxoandrost-4-en-17-yl tridecanoate as disclosed herein.

This example demonstrates that the solid state EAPI has a distinct melting point as determined using a differential scanning calorimeter. 5.9 mg of solid state EAPI (e.g., (17-β)-3-Oxoandrost-4-en-17-yl tridecanoate) was placed in the chamber of a DSC instrument and was heated from 10 to 120° C. The result is shown in FIG. 2, which shows a single peak at about 72.78° C. FIG. 3 shows the first cooling cycle with a single peak at about 47.79° C. The second heating run of this sample is show in FIG. 4 which shows a single peak at about 71.77° C. FIG. 5 shows the second cooling cycle with a single peak at about 46.46° C.

EXAMPLE 4: Differential Scanning Calorimetry of Pharmaceutical Composition Having a Solid State Ester of Active Pharmaceutical Ingredient Composition This example demonstrates that a pharmaceutical composition has a distinct melting point as determined using a differential scanning calorimeter. 29.1 mg of a pharmaceutical composition having a solid state EAPI (e.g., (17-β)-3-Oxoandrost-4-en-17-yl tridecanoate) and one or more pharmaceutically acceptable carriers was placed in the chamber of a DSC instrument and was heated from 10 to 120° C. The result is shown in FIG. 6, which shows a broad peak at 55.52° C. The first heat cycle was similar to the second heat cycle with no peak corresponding to API. The cooling cycles showed no peaks. The formulation used in this Example was prepared from about 14.5% to about 17% solid state EAPI (e.g., about 15%); about 50% to 75% lipophilic carrier (e.g., about 63% corn glycerides); about 10% to 25% hydrophilic carrier (e.g., about 15%-16% polyoxylated hydrogenated castor oil) and about 2% to 10% solidifying agent (e.g., about 6% PEG 8000).

TABLE 1

Solid state forms of (17-β)-3-Oxoandrost-4-en-17-yl tridecanoate

| Solid form | Apparent Solubility in Lipophilic additive (Oleic acid) % w/w | Apparent solubility in Lipophilic additive (Corn glycerides, Maisine) | % Dissolved in 8% Triton X100 aqueous media at RT at 30 min | % Dissolved in 8% Triton X100 aqueous media at RT at 30 min relative to form A* |
|---|---|---|---|---|
| A | <0.5 | <0.5 | <0.001 | 100 |
| B | >0.5 | >0.5 | >0.001 | >120 |
| C | >0.5 | >0.5 | >0.001 | >120 |
| D | >0.5 | >0.5 | >0.001 | >120 |

*Form A is the form described herein and characterized in the Examples by DSC and XRD.

EXAMPLE 5: Compositions and PK Studies Related to Solid State EAPI (e.g., (17-β)-3-Oxoandrost-4-En-17-Yl Tridecanoate)

Tables 1A, 1B and 1C show the typical components and their relative proportions that can be utilized in the compositions of the present inventions having the (17-β)-3-Oxoandrost-4-en-17-yl tridecanoate set forth above. Any suitable method for preparing the compositions and dosage forms described herein can be used. In some instances, the compositions are prepared by heating one or more of the carrier components to an elevated temperature e.g., above ambient temperature (above 20° C., to about 30° C., from about 30° C. to about 35° C., from about 35° C. to about 40° C., from about 40° C. to about 45° C., from about 45° C. to about 50° C., from about 50° C. to about 60° C., from about 60° C. to about 70° C., or 70° C. or more) to produce a molten carrier and the solid (17-β)-3-Oxoandrost-4-en-17-yl tridecanoate EAPI is added to the molten carrier which together which is flowable (e.g., can be processed to fill soft or hard gel capsules). The mixture of the carrier and EAPI is then formed into a unit dosage form. Typically upon cooling, the composition is a solid, semi-solid, paste, jelly, jelly or the like. In other aspects, the carrier can be liquid at about ambient temperature. In this case the carrier may still be warmed or heated as described above prior to the addition of solid EAPI. Both solid and liquid compositions (and intermediate forms e.g., semi-solid) at e.g., ambient temperature (and dosage forms containing these compositions) are contemplated.

TABLE 1A

| | Composition (weight %) Composition No. | |
|---|---|---|
| Component | 1 | 2 |
| (17-β)-3-Oxoandrost-4-en-17-yl tridecanoate | 10-35 | — |
| Carrier | 50-90 | 50-90 |
| Adjuvant* | q.s. 100 | q.s. 100 |

*Optional

TABLE 1B

Carrier components for compositions 1 and 2 of Table 1

| | Carrier component (weight %) Composition No. | | | | | |
|---|---|---|---|---|---|---|
| Carrier component | 3 | 4 | 5 | 6 | 7 | 8 |
| Lipophilic additive [e.g. Triglyceride, lipophilic surfactant, tocopherol derivative, etc.] | 100 | — | 5-95 | 100 | — | 5-95 |
| Hydrophilic additive [e.g. Hydrophilic surfactant,] | — | 100 | 5-95 | — | 100 | 5-95 |

TABLE 1C

| | Composition (weight %) Composition No. | | |
|---|---|---|---|
| Component | 9 | 10 | 11 |
| (17-β)-3-Oxoandrost-4-en-17-yl tridecanoate | 12-30 | 15-25 | 10-22 |
| Lipophilic surfactant (e.g., Glyceryl monolinoleate) | 55-80 | 50-80 | 55-80 |
| Hydrophilic surfactant (polyoxy) hydrogenated castor oil) | 0-20 | 0-20 | 0-20 |
| Alcohol (e.g., ethanol) | >10 | 0 | <10 |
| Triglyceride (e.g., castor oil) | — | — | <50 |
| Adjuvant* | q.s | q.s. | q.s |

TABLE 2

Dosage Forms of Compositions of Table 1B and Solid Forms of Table 1 and Relative Release Performance these Dosage Forms.

| Dosage form | Composition carrier of table 1B | Solid form of (17-β)-3-Oxoandrost-4-en-17-yl tridecanoate of table 1 | % Release in 8% Triton Aqueous Media at RT in 30 min Relative to Dosage Form 1 | % Bio-availability |
|---|---|---|---|---|
| 1 (not preferred) | 3 | A (not preferred) | — | <1% |
| 2 | 3 | B or C or D | >120 | >1% |
| 3 (not preferred) | 4 | A (not preferred) | 100 | <1% |
| 4 | 4 | B or C or D | >120 | >1% |

EXAMPLE 6: Methods of Use of Solid State EAPI of this Invention Comparative Pharmacokinetic Study Some of the dosage forms of compositions described herein comprising or prepared from (17-β)-3-Oxoandrost-4-en-17-yl tridecanoate were administered to human subjects as a single dose of the esters to subjects. Serial blood samples were drawn at predetermined time (e.g., t=0, 12, 24, etc.) and analyzed for testosterone concentration using a validated HPLC-MS/MS analytical method. The $C_{max}$, $C_{avg\ t1-t2}$, $T_{max}$ and $AUC_{t1t2}$ are calculated for testosterone in the serum of the subjects. Pharmacokinetic and statistical analyses are performed on the data obtained from the subjects. The pharmacokinetic parameters are defined as follows:

$AUC_{t1-t2}$: The area under the serum concentration versus time curve, from time t1 (in hours) to time t2 (in hours) measurable concentration of the administered drug, as calculated by the linear trapezoidal method. For e.g., $AUC_{t0-t24}$ refers to the area under the serum concentration versus time curve, from time 0 (zero) hours to time 24 hours post-administration of dose.

$C_{max}$: The maximum measured serum concentration of the administered drug.

$C_{avg\ t1-t2}$: The average serum concentration of testosterone obtained by dividing the $AUC_{t1-t2}/|t2-t1|$, where in t is time post-administration of dose expressed in hours.

$T_{max}$: The time (in hours) at which the maximum measured plasma concentration of the administered drug is achieved.

Mean: Average value of measured parameter of all individual subjects.

$C_{avg\ t0-t24}$: The average serum concentration of testosterone obtained by dividing the $AUC_{t0-t24}$ value by 24. This represents the average serum testosterone level over a period starting from time 0 (zero) hours to time 24 hours post-administration of dose. It should also be noted that $C_{avg\ t0-t24}$ is also referred to as simply "$C_{avg}$" in this invention.

$C_{avg\ t0-t12}$: The average serum concentration of testosterone obtained by dividing the $AUC_{t0-t12}$ value by 12. This represents the average serum testosterone level over a period starting from time 0 (zero) hours to time 24 hours post-administration of dose.

$C_{avg\ t12-t24}$: The average serum concentration of testosterone obtained by dividing the $AUC_{t12-t24}$ value by 12. This represents the average serum testosterone level over the second half of the 24-hours post-administration of dose period; i.e., from a period starting from time 12 hours to time 24 hours post-administration of dose.

Some of the pharmacokinetic results for the compositions are summarized in the Tables below.

TABLE 3

| | Starting Total mg T Equivalent Dose (±dose adjustment in mg T equivalent)* | | % Responders with $C_{ave\ t0-t24}$ (ng/dL) 300-1140 | % Responders with $C_{max}$ (ng/dL) | | |
|---|---|---|---|---|---|---|
| | | | | 1800- | | |
| | | | | ≤1500 | 2500 | >2500 |
| (17-β)-3-Oxoandrost-4-en-17-yl tridecanoate (12-20% EAPI, 55-70% lipophilic additive (e.g., lipophilic surfactant) | 300 (±50) | QD | 100 | 100 | 0-5 | 0-1 |
| | 350 (±100) | BID | 100 | 100 | 0-5 | 0-1 |
| | 1000 (±200) | QD or BID | 100 | 0 | 20-30 | 60-80 |
| | 100 (±50) | QD or BID | 50-65 | 100 | 0-5 | 0-1 |

TABLE 3-continued

| Starting Total mg T Equivalent Dose (±dose adjustment in mg T equivalent)* | % Responders with $C_{ave\ t0-t24}$ (ng/dL) | % Responders with $C_{max}$ (ng/dL) | | |
|---|---|---|---|---|
| | 300-1140 | ≤1500 | 1800-2500 | >2500 |
| Hydrophilic additive 12-20% (e.g. Hydrophilic surfactant)) | | | | |

TABLE 4

| | Composition No. | | |
|---|---|---|---|
| | 12 | 13 | 14 |
| Components | Composition (weight %) | | |
| (17-β)-3-Oxoandrost-4-en-17-yl tridecanoate | 10-30 | 10-30 | 10-30 |
| Lipophilic additive [e.g. surfactant of HLB < 10 such as mono- or di- or tri- glyceride of fatty acid or fatty acid] | 55-80 | 55-80 | 55-80 |
| Hydrophilic additive (e.g. Surfactant with HLB > 10 such as cremophor RH40) | 0-20 | 0-20 | 0-20 |
| Adjuvant | q.s. | q.s | q.s. |
| PK parameter | Serum T pharmacokinetic results | | |
| Daily dose as mg T Equivalent | 250-400 | 250-500 | 250- 400 |
| % of T-ester not dissolved in lipophilic additive at body temperature | 0 | >12 | >40 |
| % of T-ester not dissolved in lipophilic additive at 20° C. | 0 | >15 | >50 |
| No. of capsules/daily T dose | 4-5 | 3-7 | 1-3 |
| Mean serum T $C_{avg\ t0-t24}$/mg T equivalent [ng/dL/mg] | 1.65 | 1-2-2.2 | 1.86 |

It is also notable that Compositions 12-14 can be formulated as a capsule or tablet dosage form. Further, each of the capsule dosage forms can be formulated to contain from about 50 mg to about 450 mg of the ester (or more or less). For instance, the Compositions 12-14 can be formulated as a capsule or tablet dosage form.

Total daily ester dose administered is 300 to 1500 mg for Compositions 12-14. Specifically, for Compositions 12-14 the total daily (17-β)-3-Oxoandrost-4-en-17-yl dose administered is from about 3000 mg to about 1500. However, it is notable that unlike Composition 12 that has no "not dissolved" ester, Compositions 13 and 14 require fewer dosage units per administration.

Table 4 shows that the higher the fraction of the lipobalanced ester not dissolved or not solubilized, the fewer the number of daily dosage form units (e.g., capsules) that need to be administered to achieve the desirable serum testosterone levels when treating hypogonadism in a male with (17-β)-3-oxoandrost-4-en-17-yl tridecanoate. It should be noted that to provide the total daily dose of about 420 mg-850 mg of the (17-β)-3-Oxoandrost-4-en-17-yl tridecanoate for a hypogonadal subject, no more than four oral dosage form units are required; even more preferred is that no more than two oral dosage form units per day are required for administration.

Compositions 12-14 can be prepared with the lipophilic surfactant and hydrophilic surfactant in amounts such that the ratio of amount (wt %) of lipophilic surfactant to amount (wt %) of hydrophilic surfactant is greater than 2:1. Specifically, the ratio of amount (wt %) of lipophilic surfactant to amount (wt %) of hydrophilic surfactant can be greater than 2.5:1. Further, the ratio of amount (wt %) of lipophilic surfactant to amount (wt %) of hydrophilic surfactant can be greater than 3.5:1. Even further, the ratio of amount (wt %) of lipophilic surfactant to amount (wt %) of hydrophilic surfactant can be greater than 6.5:1.

Compositions 12-14 can be prepared with hydrophilic surfactant present at 20 wt % or more of the total carrier. Compositions 12-14 can be prepared with hydrophilic surfactant present at 5 wt % or less of the total carrier. The lipophilic additives, the hydrophilic additives, and the adjuvant for the representative inventive compositions shown in Table 7 can be similar to those described for compositions in Table 4. The pharmacokinetic (PK) evaluation procedure is given under Example 2. The PK results for the Compositions 13 and 14 or related capsule dosage forms thereof, following oral administration of single dose, two consecutive doses or steady state to a group of subjects, for example, hypogonadal males, along with a meal, are summarized in Table 5A, 5B and 5C.

TABLE 5A

Serum T pharmacokinetics for Compositions 13 and 14 following single administration

| PK parameter | Results |
|---|---|
| Range of mean $C_{max}$/mg of T equivalent dose, [ng/dL/mg] | 1.4 -4.5 |
| Range of mean $C_{avg\ t0-t24}$/mg of T equivalent dose, [ng/dL/mg] | 1.2-2.2 |
| Range of the $C_{avg\ t12-t24}$ as % of the $C_{avg\ t0-t24}$ | 35-70 |
| Duration of post-dosing time with serum T at >300 ng/dL | 12 to 24 hours |

TABLE 5B

Serum T pharmacokinetics for Compositions 13 and 14 following two consecutive dose administration

| PK parameter | Results |
|---|---|
| Time of T concentration below 300 ng/dL following two consecutive administrations 24 hours apart (once daily) within 48 hour time period | 2 to 7 hours |
| Time of T concentration below 300 ng/dL following two consecutive administrations about 12 hours apart (twice daily) within 24 hours | 0.5 to 3.5 hours |

TABLE 5C

Steady state serum T pharmacokinetics for Compositions 13 and 14 following at least 7 days continuous administration to a group of at least 12 subjects

| PK parameter | Results |
|---|---|
| Time of T concentration below 300 ng/dL following once daily administration | 3.5-6.5 hours |
| % of patients with serum T < 300 ng/dL for more than 7 hours following once daily administration | <50 % |
| Time of T concentration below 300 ng/dL following twice daily administration | 0.3 to 3.5 hours |
| % of patients with serum T < 300 ng/dL for more than 7 hours following twice daily administration | <20 % |

It is noteworthy that unlike Composition 12, Compositions 13 and 14 are not fully dissolved nor solubilized in the composition or dosage form thereof. Further, Compositions 13 and 14 provide, upon single administration with a meal to a human subject, a serum T mean $C_{avg\ t0\text{-}t24}$/mg of T equivalent dose administered in a range between the 1.2 to 2.2 ng/dL/mg. Additionally, Compositions 13 and 14 enable a patient-friendly dosing regimen, for instance via fewer dosage units per administration.

EXAMPLE 7: Dissolution Studies

The EAPI, compositions, dosage forms described herein containing (17-β)-3-oxoandrost-4-en-17-yl tridecanoate when subjected to in vitro dissolution testing using USP type 2 apparatus in about 1000 mL aqueous medium, can shows a release profile such that amorphous or amorphous like EAPI e.g., (17-β)-3-oxoandrost-4-en-17-yl tridecanoate releases faster than crystalline EAPI. The (17-β)-3-oxoandrost-4-en-17-yl tridecanoate EAPI, pharmaceutical composition, or dosage form containing the EAPI is subjected to in vitro dissolution testing using USP type 2 apparatus in about e.g., 1000 mL 8% Triton X100 solution in water at a specific temperature at 100 rpm for a specific time (e.g., 1, 2, 3, 4, 5, 10, 15, 30, 45, 60, 75, 90, 120, 180, or 240 minutes).

EXAMPLE 8: XRD Studies

A sample of EAPI or comprising EAPI can be analyzed by XRD. According to this example a sample of EAPI was analyzed by XRD using a Philips X'Pert X-Ray Diffractometer (XRD). A sample (e.g., 75 mg) of EAPI prepared e.g., by the method disclosed in Example 1 was deposited on a glass slide as a powder. A plot of the results obtained from this scan is shown in FIG. 6. The sample was scanned under the following conditions:
Scan Axis Gonio; Start Position [2Th.] 2.0050; End Position [2Th.] 59.9950; Step Size [2Th.] 0.0100; Scan Step Time [s] 0.5000; Scan Type Continuous; Offset [2Th.] 0.0000; Divergence Slit Type Fixed Measurement; Temperature [° C.] 25.00; Anode Material Cu; K-Alpha1 [Å] 1.54060; K-Alpha2 [Å] 1.54443; K-Beta [Å] 1.39225; K-A2/K-A1 Ratio 0.50000; Generator Settings 40 mA, 45 kV; Diffractometer Type 0000000013083126; Diffractometer Number; Goniometer Radius [mm] 200.00; Incident Beam Monochromator No; and Spinning No.

EXAMPLE 9: Dissolution Release Vs. Bioavailability

A clinical trial in humans was conducted with compositions made from or comprising a solid state testosterone ester. Single dose pharmacokinetic parameters were determined for the compositions in which the same mg amount of testosterone ester was dosed but the unit dosage forms had different dissolution/release parameters. Thirty (30) minutes before administration of each study formulation, subjects were served the following standardized high-fat, high calorie breakfast, as recommended in the U.S. Food and Drug Administration (FDA) guidance document "Food-Effect Bioavailability and Bioequivalence Studies. At least 10 subjects were in each group. The subjects were healthy post-menopausal females 45 years of age or greater to minimize effects related to endogenous (17-β)-Hydroxy-4-Androsten-3-one.

(17-β)-Hydroxy-4-Androsten-3-one Ester Unit Dosage Form A set to normal:
$AUC_{0\text{-}t}=1$
$AUC_{0\text{-}\infty}=1$
(17-β)-Hydroxy-4-Androsten-3-one Ester Unit Dosage Form B:
$AUC_{0\text{-}t}$ normalized to Dosage Form A (B/A)=0.73
$AUC_{0\text{-}\infty}$ normalized to Dosage Form A (B/A)=0.73
(17-β)-Hydroxy-4-Androsten-3-one Ester Unit Dosage Form C:
$AUC_{0\text{-}t}$ normalized to Dosage Form A (C/A)=0.46
$AUC_{0\text{-}\infty}$ normalized to Dosage Form A (C/A)=0.46
(17-β)-Hydroxy-4-Androsten-3-one Ester Unit Dosage Form D:
$AUC_{0\text{-}t}$ normalized to Dosage Form A (D/A)=0.40
$AUC_{0\text{-}\infty}$ normalized to Dosage Form A (D/A)=0.40

(17-β)-Hydroxy-4-Androsten-3-one Ester Formulation In Vitro Release Profiles

| Formulation | Time to Release 50% | Time to Release 90% |
| --- | --- | --- |
| Ester Unit Dosage Form A | 0.5 hours | 1 hour |
| Ester Unit Dosage Form B | 1 hour | 3 hours |
| Ester Unit Dosage Form C | 2 hours | 5 hours |
| Ester Unit Dosage Form D | 5.5 hours | 11 hour |

The release profiles were determined in a USP Type Apparatus at 37° C. at 100 rpm in Triton X100 8% in 1000 mL water.

EXAMPLE 10: Release Profile

The compositions, dosage forms described herein containing API can subjected to in vitro dissolution (release) testing using USP type 2 apparatus in about 1000 mL aqueous medium. The composition (e.g., dosage form) is subjected to in vitro dissolution testing using USP type 2 apparatus in about e.g., 1000 mL 8% Triton X100 solution in water at a specific temperature (e.g., 37° C.) at 100 rpm for a specific time (e.g., 1, 2, 3, 4, 5, 10, 15, 30, 45, 60, 75, 90, 120, 180, or 240 minute time point where a sample is withdrawn and analyzed for API content (e.g., via HPLC)).

EXAMPLE 11: Release Profile Stability

Figure 7:
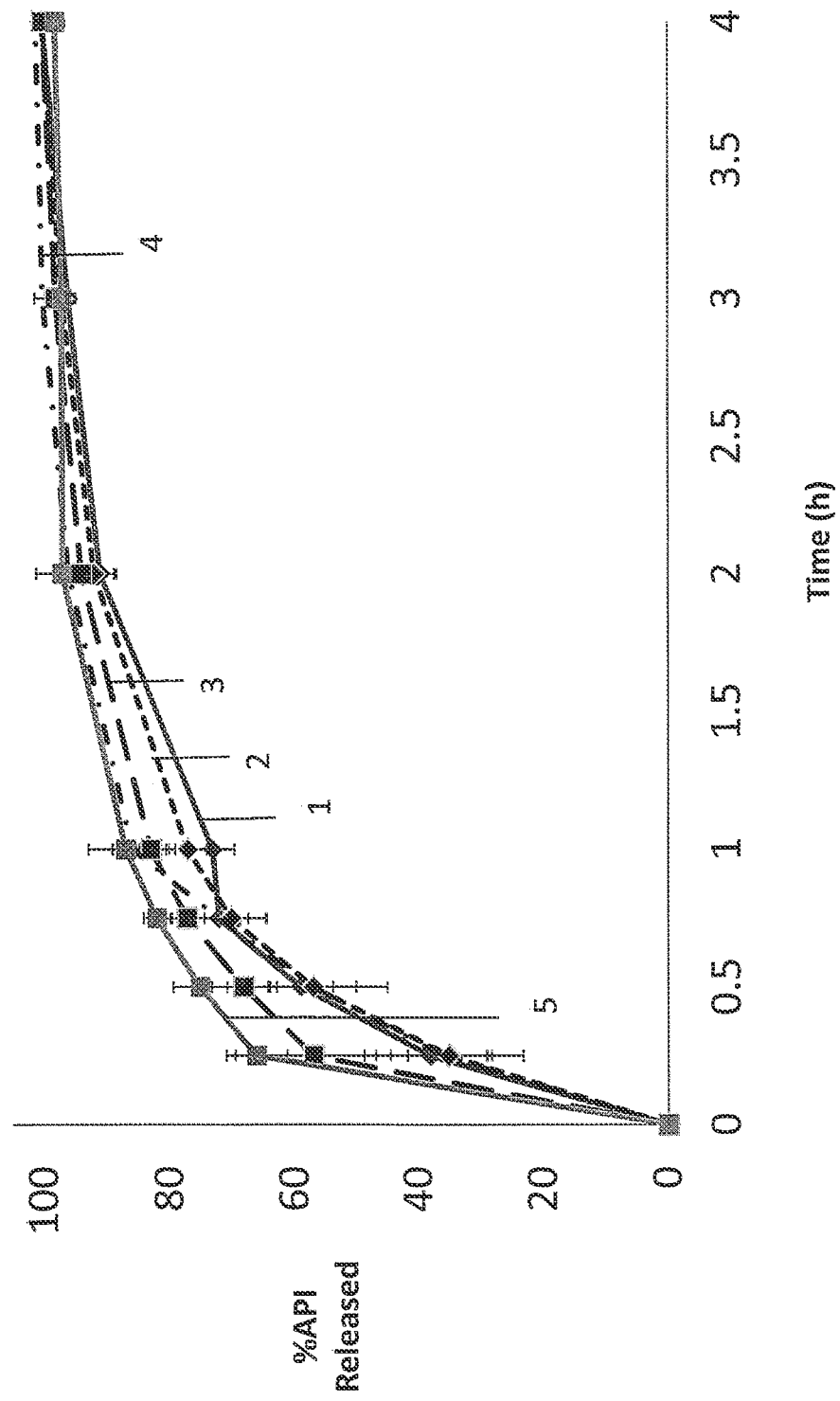
FIG. 7 shows the release profile stability of a pharmaceutical composition having or prepared from (17-β)-3-Oxoandrost-4-en-17-yl tridecanoate. See Example 10.

The compositions, dosage forms described herein containing API can subjected to in vitro dissolution (release) testing using USP type 2 apparatus in about 1000 mL aqueous medium as described in the above example after storage for particular amounts of time under specific conditions. FIG. 7 shows the release profile stability of composition (B) composition (e.g., unit dosage form of composition (B) described herein. The diamonds with solid line labeled 1 represents time point 0; the diamond with dotted line represents 1 month storage at 25° C. and 60% relative humidity (labeled 2); the square with long dashed line represents 1 month storage at 40° C. and 75% relative humidity (labeled 3); the square with dash dot line represents 3 month storage at 25° C. and 60% relative humidity (labeled 4); and the square with lighter solid line represents 3 month storage at 40° C. and 75% relative humidity (labeled 5). The X-axis represents time in hours with measurements made at 15 min, 30 min, 45 min, 1 hour, 2 hours and 4 hours. The Y-axis represents percent API released in 1000 mL 8% Triton X-100 media at 37° C. with a USP Type 2 Apparatus at 100 RPM.

Figure 8:
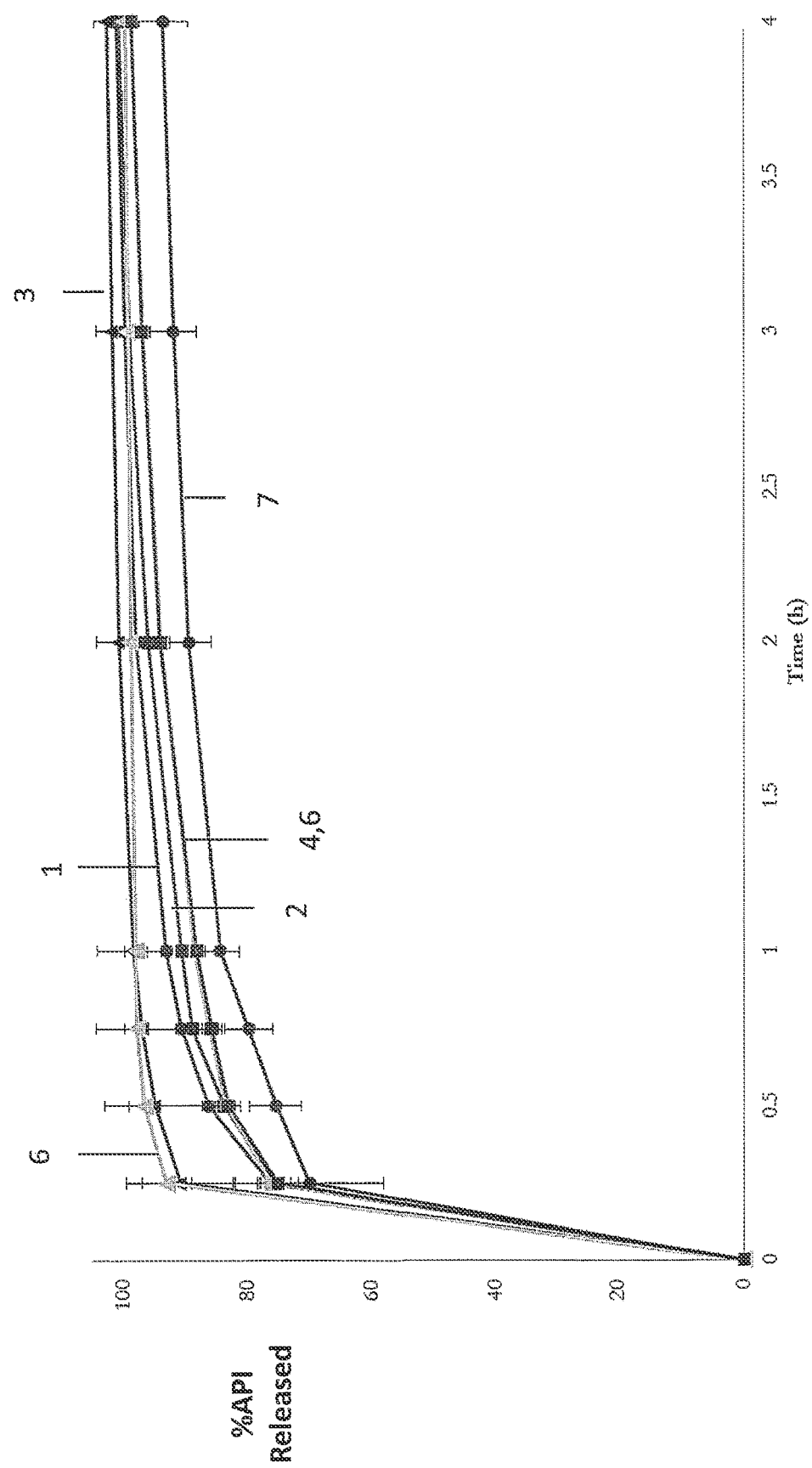
FIG. 8 shows the release profile stability of a pharmaceutical composition having or prepared from (17-β)-3-Oxoandrost-4-en-17-yl tridecanoate. See Example 10.

FIG. 8 shows the release profile stability for composition (A) at time 0 (1), 1 month stored at either 25° C. 60% RH (2) or 40° C. 75% RH (3), 2 months stored at either at either 25° C. 60% RH (4) or 40° C. 75% RH (5), and 3 months stored at either at either 25° C. 60% RH (6) or 40° C. 75% RH (7). RH is relative humidity. The X-axis represents time in hours with measurements made at 15 min, 30 min, 45 min, 1 hour, 2 hours, 3 hours and 4 hours. The Y-axis represents percent API released in 1000 mL 8% Triton X-100 media at 37° C. with a USP Type 2 Apparatus at 100 RPM.

| Composition (A) | | | |
|---|---|---|---|
| Ingredient Name | Weight Percent of Fill Pharmaceutical Composition (±1%) % w/w | Quantity Fill Material per Hard Gel Capsule (±1%) mg | Quantity Fill Material per Soft Gel Capsule (±1%) mg |
| API | 24 | 183 | 300 |
| Oleic Acid, NF | 41 | 308 | 513 |
| Peppermint Oil, NF | 18 | 136 | 225 |
| Polyoxyl 40 Hydrogenated Castor Oil, NF | 4 | 30 | 50 |
| Ascorbyl Palmitate, NF | 0.2 | 1.5 | 2.5 |
| Glyceryl Palmitostearate (Glyceryl Distearate, NF) | 12 | 90 | 150 |
| Total | 100 | 750 | 1241 |

| Composition (B) | | | |
|---|---|---|---|
| Ingredient Name | Weight Percent of Fill Pharmaceutical Composition (±1%) % w/w | Quantity Fill Material per Hard Gel Capsule (±1%) mg | Quantity Fill Material per Soft Gel Capsule (±1%) mg |
| API | 28 | 183 | 350 |
| Oleic Acid, NF | 55 | 365 | 688 |
| Polyoxyl 40 Hydrogenated Castor Oil, NF | 4 | 26 | 50 |
| Stearic Acid, NF | 4 | 26 | 50 |
| Glyceryl Palmitostearate (Glyceryl Distearate, NF; Precirol ATO 5) | 8 | 52 | 100 |
| Ascorbyl Palmitate, NF | 0.2 | 1.3 | 2.5 |
| Total | 100 | 654 | 1241 |

It is understood that the above-described various types of compositions, dosage forms and/or modes of applications are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, but not limited to, variations in size, materials, shape, form, function and manner of operation, assembly and use may be made without departing from the principles and concepts set forth herein.

What is claimed is:

1. A pharmaceutical composition comprising or prepared from a crystalline (17-β)-3-Oxoandrost-4-en-17-yl tridecanoate form having a melting point in the range of 68-75° C. and being fully or partially dissolved in a lipophilic surfactant, wherein said (17-β)-3-Oxoandrost-4-en-17-yl tridecanoate is present in an amount of from 250 mg to about 350 mg.

2. The pharmaceutical composition of claim 1, comprising a crystalline (17-β)-3-Oxoandrost-4-en-17-yl tridecanoate form having a melting point in the range of 68-75° C.

3. The pharmaceutical composition of claim 1, prepared from a crystalline (17-β)-3-Oxoandrost-4-en-17-yl tridecanoate form having a melting point in the range of 68-75° C.

4. The pharmaceutical composition of claim 1, further comprising a pharmaceutically acceptable carrier having a hydrophilic surfactant.

5. The pharmaceutical composition of claim 1, wherein said lipophilic surfactant comprises a fatty acid.

6. The pharmaceutical composition of claim 1, wherein said lipophilic surfactant comprises a monoglyceride.

7. The pharmaceutical composition of claim 1, wherein said lipophilic surfactant comprises a diglyceride.

8. The pharmaceutical composition of claim 5, further comprising a polyethylene glycol.

9. The pharmaceutical composition of claim 6, further comprising a polyethylene glycol.

10. The pharmaceutical composition of claim 1, formulated as a capsule or tablet.

11. The pharmaceutical composition of claim 5, wherein said fatty acid comprises a diglyceride.

12. The pharmaceutical composition of claim 5, wherein said composition releases greater than 70% of said (17-β)-3-Oxoandrost-4-en-17-yl tridecanoate at 2 hours and less than 100% at 30 minutes when tested with a USP type 2 apparatus in about 1000 mL 8% Octoxynol-9 solution in water at 37° C. (±0.5) at 100 rpm.

13. The pharmaceutical composition of claim 6, wherein when tested with a USP type 2 apparatus in about 1000 mL 8% Octoxynol-9 solution in water at 37° C. (±0.5) at 100 rpm said composition releases at least 40% of said (17-β)-3-Oxoandrost-4-en-17-yl tridecanoate at 60 minutes.

14. The pharmaceutical composition of claim 7, wherein said composition releases greater than 70% of said (17-β)-3-Oxoandrost-4-en-17-yl tridecanoate at 2 hours when tested with a USP type 2 apparatus in about 1000 mL 8% Octoxynol-9 solution in water at 37° C. (±0.5) at 100 rpm.

15. The pharmaceutical composition of claim 11, wherein said composition releases less than 100% of said (17-β)-3-Oxoandrost-4-en-17-yl tridecanoate at 30 minutes when tested in a USP type 2 apparatus in about 1000 mL 8% Octoxynol-9 solution in water at 37° C. (±0.5) at 100 rpm.

16. The pharmaceutical composition of claim 7, wherein said composition releases greater than 70% of said (17-β)-3-Oxoandrost-4-en-17-yl tridecanoate at 2 hours and less than 100% at 30 minutes when tested with a USP type 2 apparatus in about 1000 mL 8% Octoxynol-9 solution in water at 37° C. (±0.5) at 100 rpm.

17. The pharmaceutical composition of claim 12, wherein said (17-β)-3-Oxoandrost-4-en-17-yl tridecanoate is present in an amount of 300 mg or more and said composition is formulated as an oral capsule for administration to humans.

18. The pharmaceutical composition of claim 13, wherein said (17-β)-3-Oxoandrost-4-en-17-yl tridecanoate is present in an amount of 300 mg or more of said composition is formulated as an oral capsule for administration to humans.

19. The pharmaceutical composition of claim 14, wherein said (17-β)-3-Oxoandrost-4-en-17-yl tridecanoate is present in an amount of 300 mg or more of said composition is formulated as an oral capsule for administration to humans.

20. The pharmaceutical composition of claim 15, wherein said (17-β)-3-Oxoandrost-4-en-17-yl tridecanoate is present in an amount of 300 mg or more of said composition is formulated as an oral capsule for administration to humans.

* * * * *